US011746323B2

(12) United States Patent
D'Amour et al.

(10) Patent No.: US 11,746,323 B2
(45) Date of Patent: *Sep. 5, 2023

(54) PDX1 POSITIVE FOREGUT ENDODERM CELLS AND METHODS OF PRODUCTION

(71) Applicant: ViaCyte, Inc., San Diego, CA (US)

(72) Inventors: Kevin Allen D'Amour, San Diego, CA (US); Alan D. Agulnick, San Diego, CA (US); Susan Eliazer, Moraga, CA (US); Emmanuel E. Baetge, Encinitas, CA (US)

(73) Assignee: ViaCyte, Inc., San Diego, CA (US)

( * ) Notice: Subject to any disclaimer, the term of this patent is extended or adjusted under 35 U.S.C. 154(b) by 659 days.

This patent is subject to a terminal disclaimer.

(21) Appl. No.: 16/583,135

(22) Filed: Sep. 25, 2019

(65) Prior Publication Data
US 2020/0017824 A1    Jan. 16, 2020

Related U.S. Application Data

(63) Continuation of application No. 16/177,235, filed on Oct. 31, 2018, now Pat. No. 10,465,162, which is a continuation of application No. 14/947,999, filed on Nov. 20, 2015, now abandoned, which is a continuation of application No. 14/146,510, filed on Jan. 2, 2014, now Pat. No. 9,222,069, which is a continuation of application No. 11/587,735, filed as application No. PCT/US2005/014239 on Apr. 26, 2005, now Pat. No. 8,647,873, and a continuation-in-part of application No. 11/021,618, filed on Dec. 23, 2004, now Pat. No. 7,510,876.

(60) Provisional application No. 60/587,942, filed on Jul. 14, 2004, provisional application No. 60/586,566, filed on Jul. 9, 2004, provisional application No. 60/566,293, filed on Apr. 27, 2004.

(51) Int. Cl.
C12N 5/073    (2010.01)
C12N 5/0735    (2010.01)

(52) U.S. Cl.
CPC ......... *C12N 5/0603* (2013.01); *C12N 5/0606* (2013.01); *C12N 2501/115* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/415* (2013.01); *C12N 2502/13* (2013.01); *C12N 2506/02* (2013.01)

(58) Field of Classification Search
CPC .................................................. C12N 5/0603
See application file for complete search history.

(56) References Cited

U.S. PATENT DOCUMENTS

| 4,683,195 A | 7/1987 | Mullis et al. |
| 4,683,202 A | 7/1987 | Mullis |
| 4,816,567 A | 3/1989 | Cabilly et al. |
| 5,453,357 A | 9/1995 | Hogan |
| 5,670,372 A | 9/1997 | Hogan |
| 5,690,926 A | 11/1997 | Hogan |
| 5,817,637 A | 10/1998 | Weiner et al. |
| 5,830,876 A | 11/1998 | Weiner et al. |
| 5,843,780 A | 12/1998 | Thomson |
| 5,866,366 A | 2/1999 | Kallender |
| 5,869,620 A | 2/1999 | Whitlow et al. |
| 6,015,671 A | 1/2000 | Field |
| 6,090,592 A | 7/2000 | Adams et al. |
| 6,090,622 A | 7/2000 | Gearhart et al. |
| 6,117,635 A | 9/2000 | Nazarenko et al. |
| 6,117,986 A | 9/2000 | Nardone et al. |
| 6,165,993 A | 12/2000 | Herrmann et al. |
| 6,200,806 B1 | 3/2001 | Thomson |
| 6,251,671 B1 | 6/2001 | Hogan et al. |
| 6,261,281 B1 | 7/2001 | Mathiesen et al. |
| 6,458,589 B1 | 10/2002 | Rambhatla et al. |
| 6,506,574 B1 | 1/2003 | Rambhatla et al. |
| 6,872,389 B1 | 3/2005 | Faris |
| 6,921,811 B2 | 7/2005 | Zamora et al. |
| 7,033,831 B2 | 4/2006 | Fisk et al. |
| 7,153,684 B1 | 12/2006 | Hogan |
| 7,256,042 B2 | 8/2007 | Rambhatla et al. |

(Continued)

FOREIGN PATENT DOCUMENTS

| CA | 2684022 A1 | 9/2014 |
| EP | 0543942 A1 | 6/1993 |

(Continued)

OTHER PUBLICATIONS

Brewer et al., 1993, J. Neuroscience Res., vol. 35, pp. 567-576 (Year: 1993).*
Johannesson et al., 2009, PLoS One, vol. 4(3), pp. 1-13 (Year: 2009).*
Roberts D. (2000, Developmental Dynamics, vol. 219, pp. 109-120). (Year: 2000).*
Armelin Ha, (1973, PNAS, vol. 70(9), pp. 2702-2706.

(Continued)

Primary Examiner — Anoop K Singh
Assistant Examiner — David A Montanari
(74) Attorney, Agent, or Firm — KLARQUIST SPARKMAN, LLP

(57) ABSTRACT

Disclosed herein are cell cultures comprising PDX1-positive endoderm cells and methods of producing the same. Also disclosed herein are cell populations comprising substantially purified PDX1-positive endoderm cells as well as methods for enriching, isolating and purifying PDX1-positive endoderm cells from other cell types. Methods of identifying differentiation factors capable of promoting the differentiation of endoderm cells, such as PDX1-positive foregut endoderm cells and PDX1-negative definitive endoderm cells, are also disclosed.

8 Claims, 51 Drawing Sheets
Specification includes a Sequence Listing.

(56) References Cited

U.S. PATENT DOCUMENTS

| | | |
|---|---|---|
| 7,326,572 B2 | 2/2008 | Fisk et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 8,586,357 B2 | 11/2013 | D'Amour et al. |
| 8,623,645 B2 | 1/2014 | D'Amour et al. |
| 8,633,024 B2 | 1/2014 | D'Amour et al. |
| 8,647,873 B2 | 2/2014 | D'Amour et al. |
| 8,658,151 B2 | 2/2014 | Kelly et al. |
| 9,222,069 B2 | 12/2015 | D'Amour et al. |
| 9,732,318 B2 | 8/2017 | D'Amour et al. |
| 2002/0072117 A1 | 6/2002 | Xu et al. |
| 2002/0090723 A1 | 7/2002 | Carpenter et al. |
| 2002/0160511 A1 | 10/2002 | Rambhatla et al. |
| 2003/0054437 A1 | 3/2003 | Ingham et al. |
| 2003/0109450 A1 | 6/2003 | Boudreau et al. |
| 2003/0138948 A1 | 7/2003 | Fisk et al. |
| 2003/0138949 A1 | 7/2003 | Bhushan et al. |
| 2003/0175956 A1 | 9/2003 | Bodnar et al. |
| 2003/0190748 A1 | 10/2003 | Thomson et al. |
| 2003/0224411 A1 | 12/2003 | Stanton et al. |
| 2004/0127406 A1 | 7/2004 | Presnell et al. |
| 2004/0229350 A1 | 11/2004 | Strelchenko et al. |
| 2005/0079159 A1 | 4/2005 | Shastri et al. |
| 2005/0158853 A1 | 7/2005 | D Amour et al. |
| 2006/0003446 A1 | 1/2006 | Keller et al. |
| 2006/0019387 A1 | 1/2006 | Faris |
| 2006/0040385 A1 | 2/2006 | Itskovitz-Eldor et al. |
| 2006/0040387 A1 | 2/2006 | Fisk et al. |
| 2006/0128018 A1 | 6/2006 | Zwaka et al. |
| 2006/0148081 A1 | 7/2006 | Kelly et al. |
| 2006/0276420 A1 | 12/2006 | Keller et al. |
| 2007/0154984 A1 | 7/2007 | D Amour et al. |
| 2007/0281355 A1 | 12/2007 | Dalton et al. |
| 2009/0253202 A1 | 10/2009 | D Amour et al. |
| 2010/0151568 A1 | 6/2010 | D Amour et al. |
| 2010/0233755 A1 | 9/2010 | D Amour et al. |
| 2014/0193902 A1 | 7/2014 | D Amour et al. |

FOREIGN PATENT DOCUMENTS

| | | |
|---|---|---|
| EP | 1298201 A1 | 4/2003 |
| EP | 1627912 A1 | 2/2006 |
| EP | 1285961 B1 | 11/2007 |
| JP | H09188630 A | 7/1997 |
| JP | 2004504834 A | 2/2004 |
| JP | 2007516728 A | 6/2007 |
| WO | 9818943 A1 | 5/1998 |
| WO | 9830679 A1 | 7/1998 |
| WO | 9843679 A1 | 10/1998 |
| WO | 9855137 A1 | 12/1998 |
| WO | 9953021 A1 | 1/1999 |
| WO | 9913915 A1 | 3/1999 |
| WO | 9920741 A1 | 4/1999 |
| WO | 0029442 A1 | 5/2000 |
| WO | 0049137 A2 | 8/2000 |
| WO | 0151616 A2 | 7/2001 |
| WO | 0153465 A1 | 7/2001 |
| WO | 0166697 A2 | 9/2001 |
| WO | 0210347 A2 | 2/2002 |
| WO | 0234880 A2 | 5/2002 |
| WO | 02059278 A2 | 8/2002 |
| WO | 02092756 A2 | 11/2002 |
| WO | 02096203 A1 | 12/2002 |
| WO | 02102997 A2 | 12/2002 |
| WO | 03029445 A1 | 4/2003 |
| WO | 03046141 A2 | 6/2003 |
| WO | 03050249 A2 | 6/2003 |
| WO | 03062405 A2 | 7/2003 |
| WO | 03078585 A2 | 9/2003 |
| WO | 03095628 A2 | 11/2003 |
| WO | 03100026 A2 | 12/2003 |
| WO | 2004073633 A2 | 9/2004 |
| WO | 2004098490 A2 | 11/2004 |
| WO | 2005017131 A2 | 2/2005 |
| WO | 2005033294 A2 | 4/2005 |
| WO | 2005045001 A2 | 5/2005 |
| WO | 2005063971 A2 | 7/2005 |
| WO | 2005097977 A2 | 10/2005 |
| WO | 2005097980 A2 | 10/2005 |
| WO | 2005116073 A2 | 12/2005 |
| WO | 2006016999 A1 | 2/2006 |
| WO | 2006017134 A2 | 2/2006 |
| WO | 2006020919 A2 | 2/2006 |
| WO | 2006034873 A1 | 4/2006 |
| WO | 2006083782 A2 | 8/2006 |
| WO | 2007002210 A2 | 1/2007 |
| WO | 2007047509 A2 | 4/2007 |
| WO | 2007047979 A2 | 4/2007 |
| WO | 2007059007 A2 | 5/2007 |
| WO | 2007088372 A2 | 8/2007 |
| WO | 2009154606 A1 | 12/2009 |

OTHER PUBLICATIONS

Assady et al. "Insulin production by human embryonic stem cells" (2001) Diabetes 50(8): 1691-1697.

Bar-Nur, Ori et al., "Epigenetic memory and Preferential Lineage-Specific Differentiation in Induced Pluripotent Stem Dells Derived from Human Pancreatic Islet Beta Cells," Cell Stem Cell, vol. 9:17-23 (2011).

Botton et al., (2000, TIG, vol. 16(3), pp. 124-130.

Brink, T.C., et al., "The Origins of Human Embryonic Stem Cells: A Biological Conundrum," Cell, Tissues, Organs, vol. 188(1-2):9-22 (2008).

Campbell, Frederick Charles, "Gastrointestinal Tract," Handbook of Stem Cells (2004) Elsevier, Inc., vol. 1, Chapter 35, pp. 371-378.

Cell Culture, Combinations of GIBCO Serum-Free Media Improve Growth of Primary Neurons, Facilitating Better Control in Research studies. Connecting with Neuroscience; Spring 2002; pp. 2-0.

Chen, et al., Development, 140:675-686 (2013).

Chen, et al., Two Modes by which Lefty Proteins Inhibit Nodal Signaling; Current Biology, vol. 14, 618-624, Apr. 6, 2004.

Connecting with Neuroscience; Combinations of GIBO Serum-Free Media Improve Growth of Primary Neurons, Facilitating Better Control in Research Studies, Cell Culture, Spring, 2002, Focus 16, No. 1.

D'Amour et al.(e-Published Oct. 28, 2005, Nature Biotechnology, vol. 23(12), pp. 1534-1541).

D'Amour et al., "Efficient differentiation of human embryonic stem cells to definitive endoderm." Nature Biotechnology, Dec. 2005, vol. 23, No. 12, pp. 1534-1541.

D'Amour et al., 2005, Nature Biotechnology, vol. 23(12), pp. 1534-1541.

D'Amour et al., 2006, Nature Biotechnology, vol. 24(11), pp. 1392-1401.

Dignass, et al., Functional Relevance of Activin A in the Intestinal Epithelium, Scandinavian Journal of Gastroenterology, vol. 37, Issue 8, pp. 936-943.

Douguchi, Hiroshi, "Veterinary Embryology Lecture," Department of Vet. Anatomy, NVAU, 1998; Japanese; with English translation.

Evans, M.J. et al., "Establishment in culture of pluripotential cells from mouse embryos," Nature, vol. 292:154-156 (1981).

Fayet et al., (2002, Thyroid, vol. 12(7), pp. 539-546).

Gavrilov, S. et al., "Derivation of Two New Human Embryonic Stem Cell Likes from Nonviable Human Embryos," Stem Cells International, 138(37-38):540-549, 2011.

Gavrilov, S. et al., "Non-Viable Human Embryos as a Source of Viable Cells for Embryonic Stem Cell Derivation," Reproductive BioMedicine Online, 18(2):301-308, Feb. 2009.

Grapin-Botton et al. (2000, TIG, vol. 16(3), pp. 124-130).

Grapin-Botton, "Endoderm development: from patterning to organogenesis," Trends Genet. 16:124-30,2000.

Guidato, Sonia, et al., "Somatic Motoneurone Specification in the Hindbrain: the Influence of Somite-Derived Signals, retinoic acid and Hoxa3", Development, (2003) vol. 130, pp. 2981-2996.

Habener, Joel F., "Minireview: Transcriptional Regulation in Pancreatic Development", Endocrinology, 146(3): pp. 1025-1034.

Hannan et al. (2013, Stem Cell Reports, vol. 1, pp. 293-306).

(56) References Cited

OTHER PUBLICATIONS

Hebrok, Matthias, Hedgehog signaling in pancreas development, Mechanisms of Development 120 (2003) 45.47.
Hooper et al., HPRT-deficient (Lesch-Nyhan) mouse embryos derived from germline colonization by cultured cells; Nature, vol. 326, Mar. 19, 1987.
Hoshi et al., (2007, Endocrinology, vol. 148(9), pp. 4251-4258.
Houle, Martin, Retinoic Acid regulation of Cdx1: an Indirect Mechanism for Retinoids and Vertebral specification, Molecular and Cellular Biology, Sep. 2000, vol. 20, No. 17, p. 6579-6586.
Ireland KA., Visualizing Human Biology, 3rd Ed., Wiley and Sons Inc., 2008,3 pages total.
Ireland, K.A., Visualizing Human Biology, 3rd. Ed., Wiley and Sons Inc., 3 pages total, 2008.
Jacquemin, Patrick, et al., Transcription Factor Hepatocyte Nuclear Factor 6 Regulates Pancreatic Endocrine Cell Differentiation and Controls Expression of the Proendocrine Gene ngn3, Milecular and Cellular Biology, Jun. 2000, vol. 20. No. 12, pp. 4415-4454.
Jaramillo, Maria et al., "Potential for Pancreatic Maturation of Differentiating Human Embryonic Stem Cells is Sensitive to the Specific Pathway of Definitive Endoderm Commitment," PLOS One, vol. 9, Issue 4, Apr. 2014, pp. 1-14.
Jiang et al. Generation of insulin-producing islet-like clusters from human embryonic stem cells, Stem Cells, 25(8):1940-53, 2007.
Kahan, B.W., et al. "Pancreatic Precursors and Differentiated Islet Cell Types from Murine Embryonic Stem Cells: An in Vitro Model to Study Islet Differentiation." Diabetes. Aug. 2003, vol. 52, No. 8, pp. 2016-2024.
Kaufman, D., et al., Cell Contact and Cytokine Requirements for Hematopoietic Differentiation of Human ES Cells, Blood, 2002,vol. 100, p. 151b.
Kaufman, D.S. et al. (Sep. 11, 2001, e=published Sep. 4, 2001). "Hematopoietic colony-forming cells derived from human embryonic stem cells," Proc Natl Acad Sci USA 98(19):10716-10721.
Keller, Gordon, et al., Hematopoitic Commitment During Embryonic Stem Cell Differentiation in Culture, Moleclar and Cellular Biology, Jan. 1993, p. 473-486.
Kispert, Andreas et al., "The Brachyury gene encodes a novel DNA binding protein," The EMBO Journal, vol. 12, No. 8, pp. 3211-3220, 1993.
Kubo et al. (e-Pub Mar. 3, 2004, Development, vol. 131(7), pp. 1651-1662).
Kubo, et al., "Development of definitive endoderm from embryonic stem cells in culture", Development, 131 (2004) p. 1651-1662.
Levenberg, et al., Differentiation of human embryonic stem cells on three-dimensional polymer scaffolds, PNAS, Oct. 28, 2003, vol. 100, No. 22, 12741-12746.
Lister, Ryan et al., "Hotspots of aberrant epigenomic reprogramming in human induced pluripotent stem cells," Nature, Vo 47 (7336):68-73 (2011).
Liu, WeiQiang et al., "Higher Copy Number Variation and Diverse X Chromosome Inactivation in Parthenote-derived Human Embryonic Stem Cells," Journal of Reproduction and Development, vol. 58(6):642-648 (2012).
Loebel, et al., Lineage choice and differentiation in mouse embryos and embryonic stem cells, Developmental Biology, vol. 264, Issue 1,Dec. 1, 20032, pp. 1-14.
Mavillio, Fulvio, Activation of four homeobox gene clusters in human embryonal carcinoma cells induced to differentiate by retinoic acid, Differentiatin, Springer-Verlag 1988 37: 73-79.
Meyer, Barbara, et al., "Mouse Cdz-1 Expression During Gastrulation." Development, (1993) vol. 117, pp. 191-203.
Miyanishi, Masanori et al., Due Pluripotent Stem Cells Exist in Adult Mice as Very Small Embryonic Stem Cells?, Stem Cell Reports, vol. 1 198-208; Aug. 6, 2013.
Mohamed, et al., "B-Catenin Signaling Marks the Prospective Site of Primitive Streak Formation in the Mouse Embryo" Dev. Dynamics 231:416-424 (2004).
Muller, Franz-Josef et al., "A bioinformatics assay for pluripotency in human cells," Nat. Methods, vol. 8(4): 315-317 (2011).

Munoz-Sanjuan et al., Neural Induction, The Default Model and Embryonic Stem Cells., Nature Reviews, Neuroscience, vol. 3, Apr. 2002 271-280.
Offield et al., "PDX-1 is Required for Pancreatic Outgrowth and Differentiation of the Rostral Duodenum" Development (1996) 122: 983-995.
Pauklin et al., Activin/Nodal signaling in stem cells, The Company of Biologists, Development; 2015, 142, 607-619.
Reijo et al., (2009, Differentiation, vol. 78, pp. 18-23).
Reijo et al., Gene expression profiles of human inner cell mass cells and embryonic stem cells, Differentiation, (2009) vol. 78, pp. 18-23.
Reubinoff et al., (2000, Nature Biotechnology, vol. 18, pp. 399-404).
Reubinoff et al., "Embryonic stem cell lines from human blastocysts: somatic differentiation in vitro", (2000) Nat Biotechnol 18:399-404.
Revazova, E.S. et al., "Patient-Specific Stem Cell Lines Derived From Human Parthenogenetic Blastocysts," Cloning and Stem Cells, 9(3):432-449, 2007.
Rodaway et al. "Mesendoderm: An Ancient Germ Layer?" Cell, vol. 105, Apr. 2001, pp. 169-172.
Rodaway, et al., "Induction of the mesendoderm in the zebrafish germ ring by yolk cell-derived TGF-B family signals and discrimination of mesoderm and endoderm by FGF", Development, 1266, 1999.
Ryan, J., et al., Unraveling the Pluripotency Paradox in Fetal and Placental Mesenchymal Stem Cells: Oct-4 Expression and the Case of the Emperor's new clothes; Stem Cell Rev. and Rep. (2013) 9:408-421.
Schuldiner et al., Effects of eight growth factors on the differentiation of cells derived from human embryonic stem cells, PNAS, Oct. 10, 2000, vol. 97, No. 21.
Scott, Matthew P., "Letter to the Editor—Vertebrate Homeobox Gene Nomenclature," Cell, vol. 71; Nov. 13, 1992; pp. 55.
Serls, et al., (Jan. 2005, Development, vol. 132, pp. 35-47).
Shimozaki, Koji et al., Involvement of Oct3/4 in the enhancement of neuronal differentiation of ES cells in neurogenesis-inducing cultures; Development, 130, 2505-2512.
Sigma-Aldrich Product Information for all-trans retinoic acid (Oct. 8, 1996).
Slager, H.G., et al., "Secretion of Transforming Growth Factor-B Isoforms by Embyonic Stem Cells: Isoform and Latency are Dependent on Direction of Differentiation", Journal of Cellular Physiology, 1993.
Smolich et al., (1993, Mol. Biol. Cell, vol. 4 pp. 1267-1275).
Soubeyran, Philippe, et al., "Cdx1 Promotes Differentiation in a Rat Intestinal Epithelial Cell Line," Gastroenterology (1999) vol. 117, pp. 1326-1338.
Stafford. D. and Prince, V., (2001) Pancreatic Development, Proliferation and Stem Cells. Meeting Abstract, Oct. 18-19. National Institute of Health.
Thermofisher Scientific Technical Resources, N-2 Supplement (100X) liquid.
Tiedemann et al., Pluripotent cells (stem cells) and their determination and differentiation in early vertebrate embryogenesis, vol. 43, Issue 5, Oct. 2001, pp. 469-502.
Tremblay KD et al.,Formation of the definitive endoderm in mouse is a Smad2-dependent process.Development. Jul. 2000;127(14):3079-90.Abstract, 1-25.
Tulachan et al., "All-Trans retinoic acid induces differentiation of ducts and endocrine cells by mesenchymal/epithelial interactions in embryonic pancreas," Diabetes, 2003, 52:70-84.
Turnpenny, L, et al., "Evaluating Human Embryonic Germ Cells: Concord and Conflict as Pluripotent Stem Cells," Stem Cells, 2006:24:212-220.
Turovets, N. et al., "Human parthenogenetic stem cells produce enriched populations of definitive endoderm cells after trichostatin A pretreatment," Differentiation, 81(5):292-298, Feb. 8, 2011.
U.S. Appl. Nos. 601587,942, U.S. Appl. No. 60/586,566 and U.S. Appl. No. 60/532,004.
Vale et al., "Purification and characterization of an FSH releasing protein from porcine ovarian follicular fluid," Nature, (1986) 321(6072):776-9.

(56) References Cited

OTHER PUBLICATIONS

Vallier et al. "Activin/Nodal and FGF Pathways Cooperate to Maintain Pluripotency of Human Embryonic Stem Cells" (2005) J Cell Sci. 118:4495-509.
Vallier et al. "Nodal Inhibits Differentiation of Human Embryonic Stem Cells Along the Neuroectodermal Default Pathway" (2004) Developmental Biology 275, 403-421.
Vallier et al., Human Embryonic Stem Cells, An In Vitro Model to Study Mechanisms controlling Pluripotency in Early Mammalian Development, Stem Cell Reviews, vol. 1, pp. 119-130.
Vallier, L., Reynolds, D. & Pedersen, R.A. Nodal inhibits differentiation of human embryonic stem cells along the neuroectodermal default pathway. Dev Biol 275, 403-421 (2004).
Van Den Wijngaard et al., (1995, Genomics, vol. 27, pp. 559-560).
Ware et al. (2014, PNAS, vol. 111(12), pp. 4484-4489).
Wiles, Michael et al., Embryonic Stem Cell Development in a Chemically Defined Medium, Experimental Cell Research, 247, 241-248 (1999).
Wilson, Valerie et al., "Chimeric analysis of T (Brachyury) gene function", Development, 117, 1993.
Yamaguchi, Current Biology 2001, II:R713-R724.
Yelon et al. (2002, Current Biology, vol. 12, R707-R709).
Zambidis, Elias T., et al, Efficient Stromal-Free Generation of Primitive Human Hematopoietic Progenitors from Human Embryonic Stem Cells, Kimmel Comprehensive Cancer Center, Johns Hopkins School of Medicine, Baltimore, MD, USA, Abstract #584.
Ciani et al., WNTs in the vertebrate nervous system: from patterning to neuronal connectivity, Nat Rev Neurosci. 6(5):351-62, 2005.
Takahashi et al., Cell, (2007), vol. 131, pp. 861-872.
Valdimarsdottir G., et al, Functions of the TGFB Superfamily in Human Embryonic Stem Cells, ARMIS, 113, 773-89, 2005.
Skoudy et al., "Transforming growth factor (TGF)ß, fibroblast growth factor (FGF) and retinoid signalling pathways promote pancreatic exocrine gene expression in mouse embryonic stem cells," *Biochem J.*, 379:749-756, 2004.

\* cited by examiner

FIG. 6A
FIG. 6B
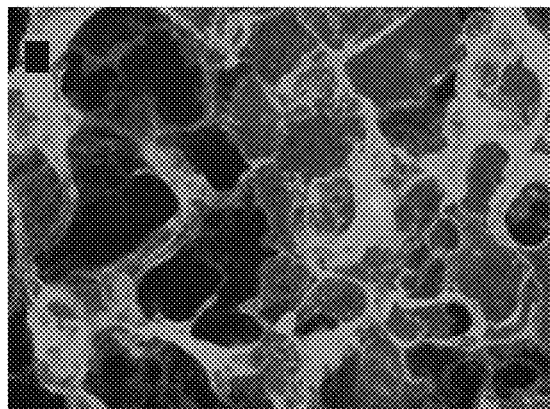
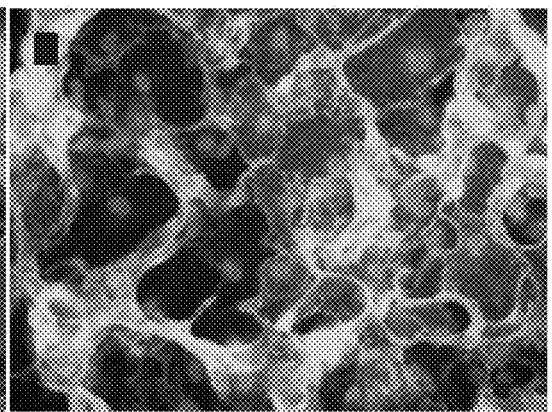
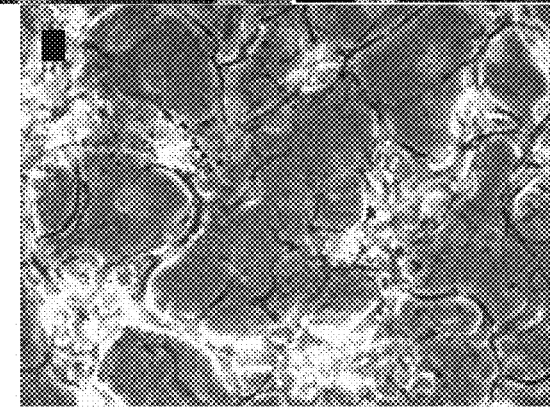
FIG. 6C (+) Activin A 6.8-fold difference (−) Activin A

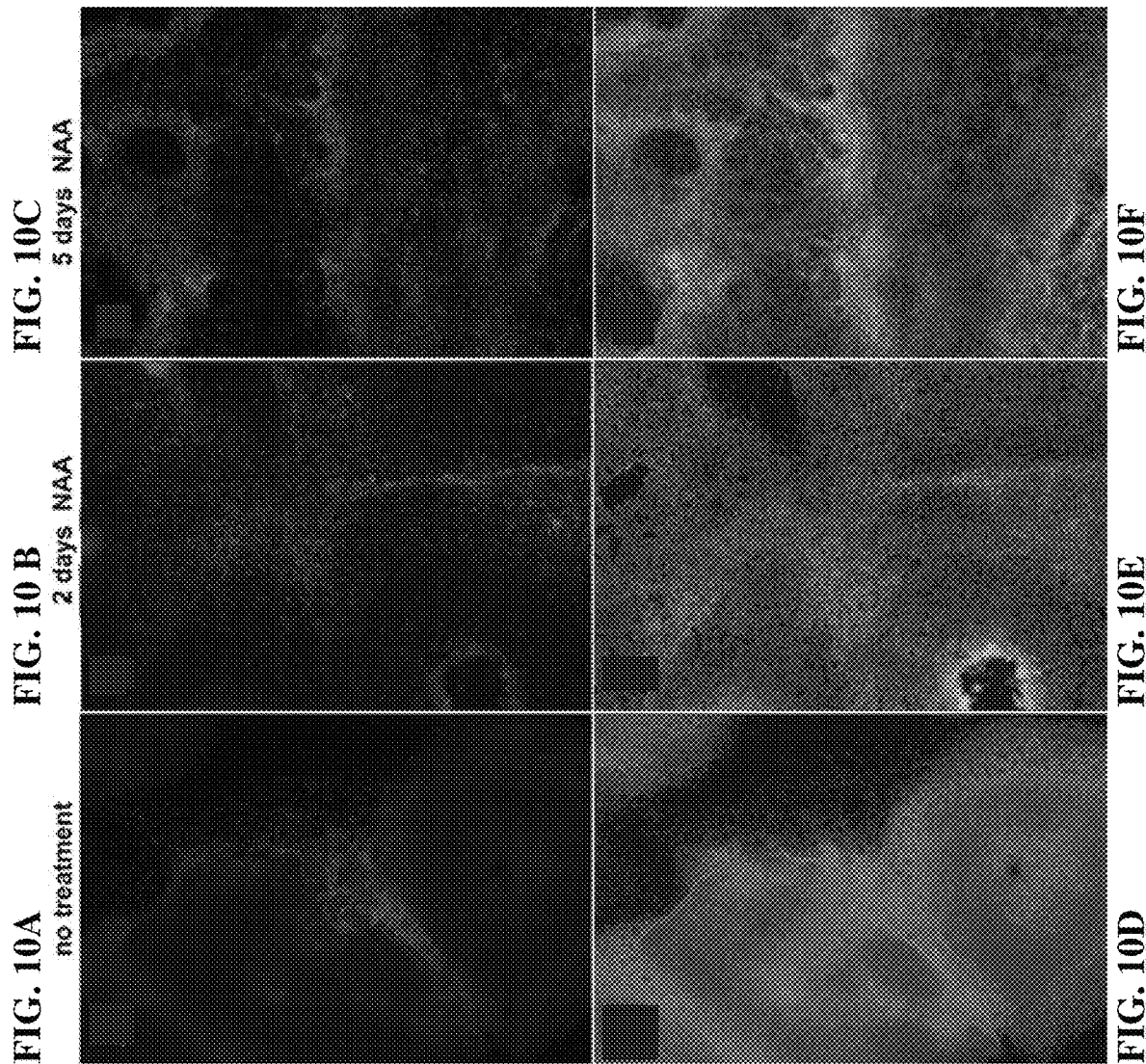

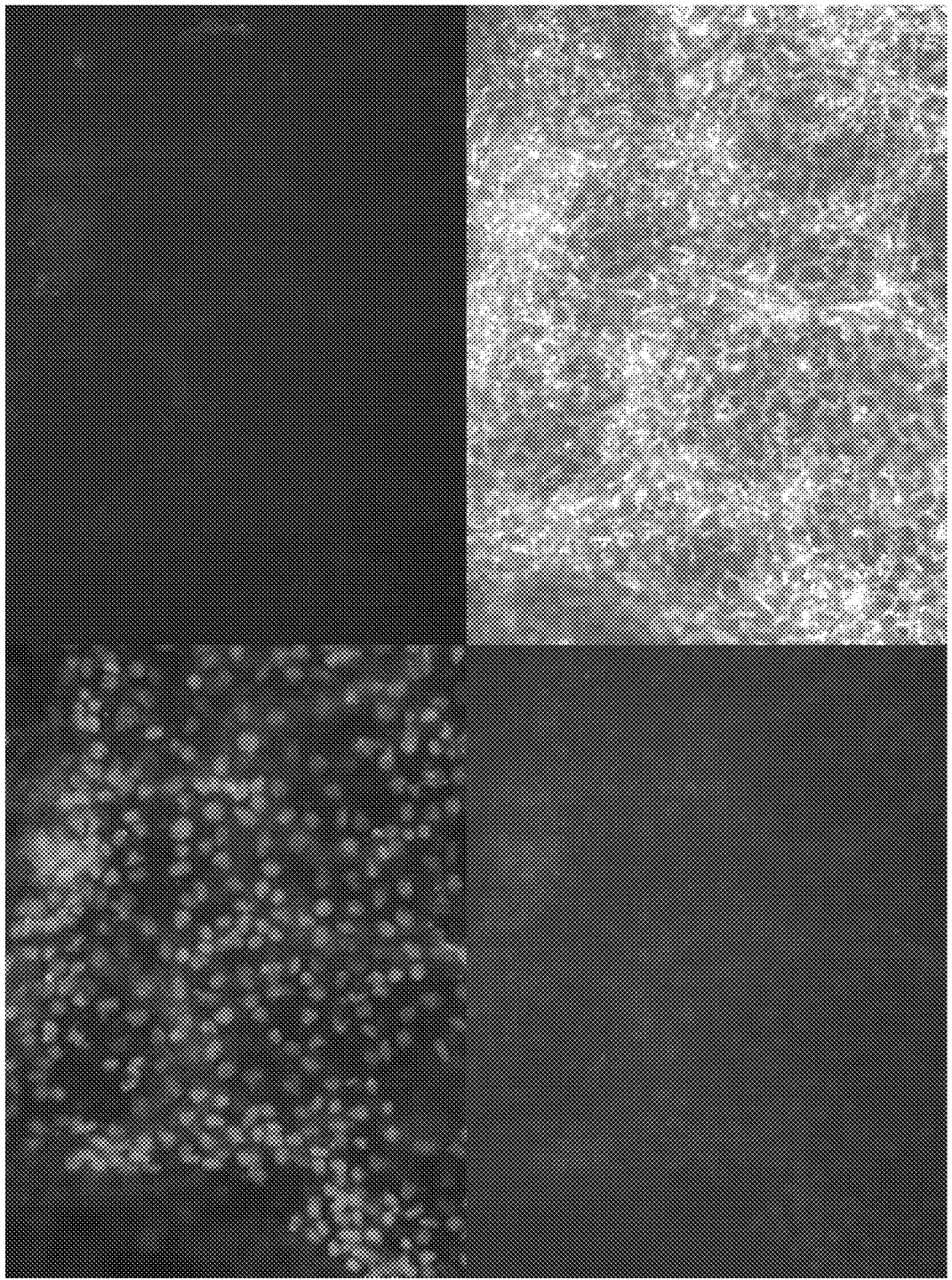

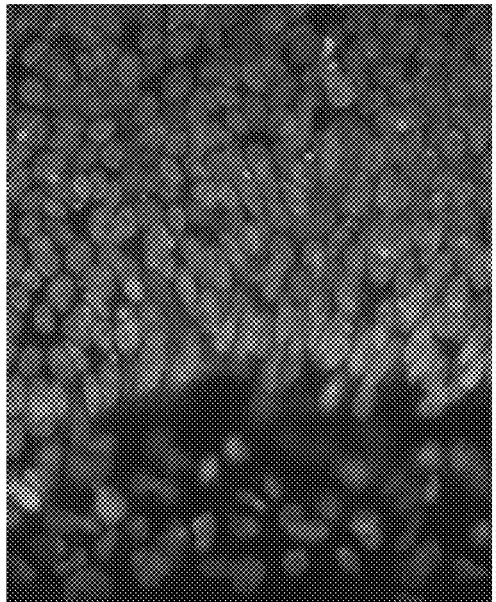
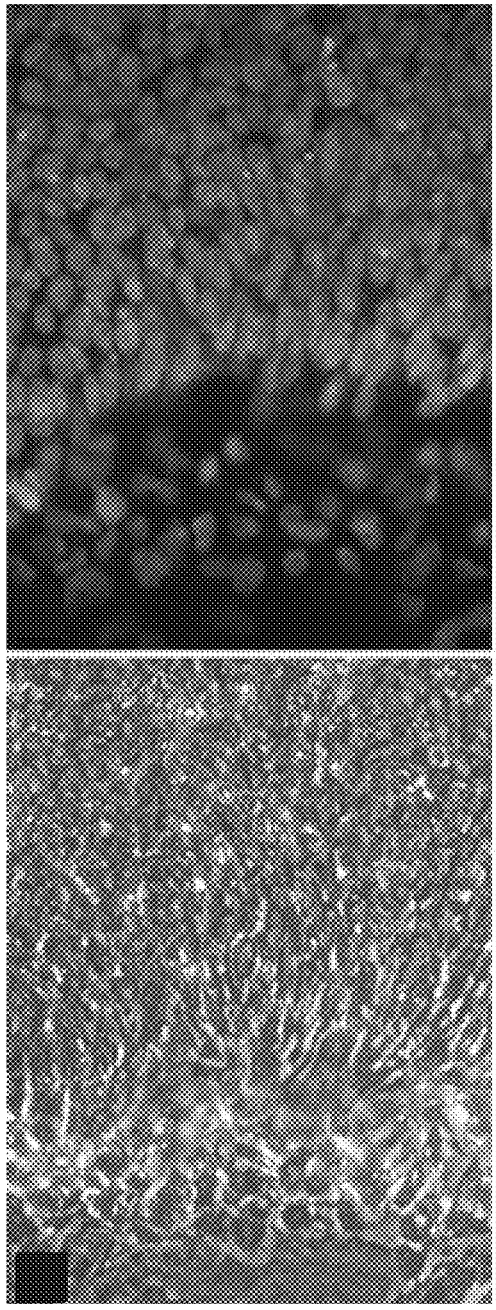
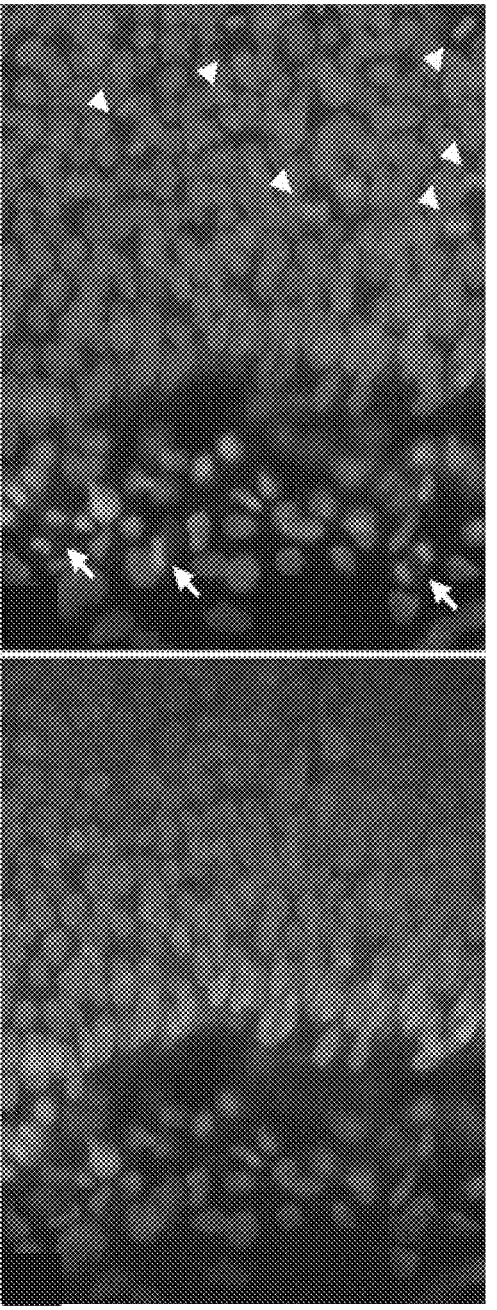
FIG. 25A
FIG. 25B
FIG. 25C
FIG. 25D

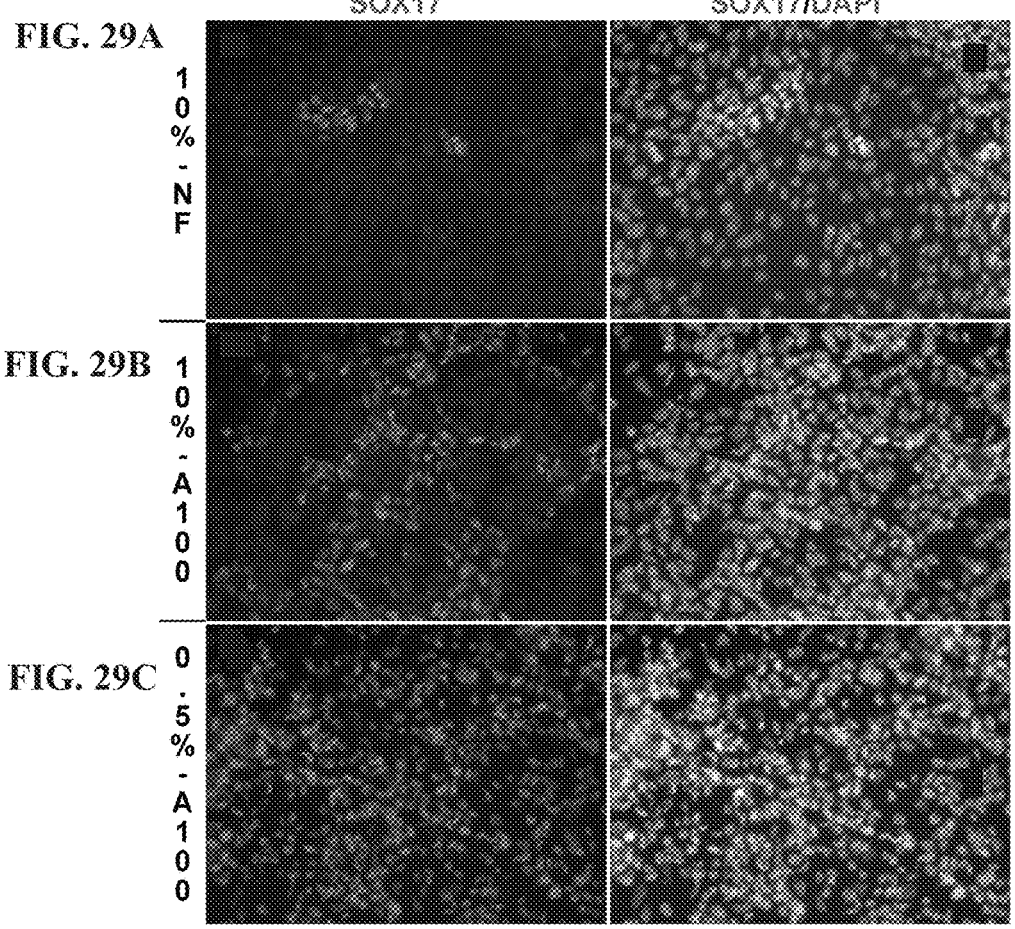

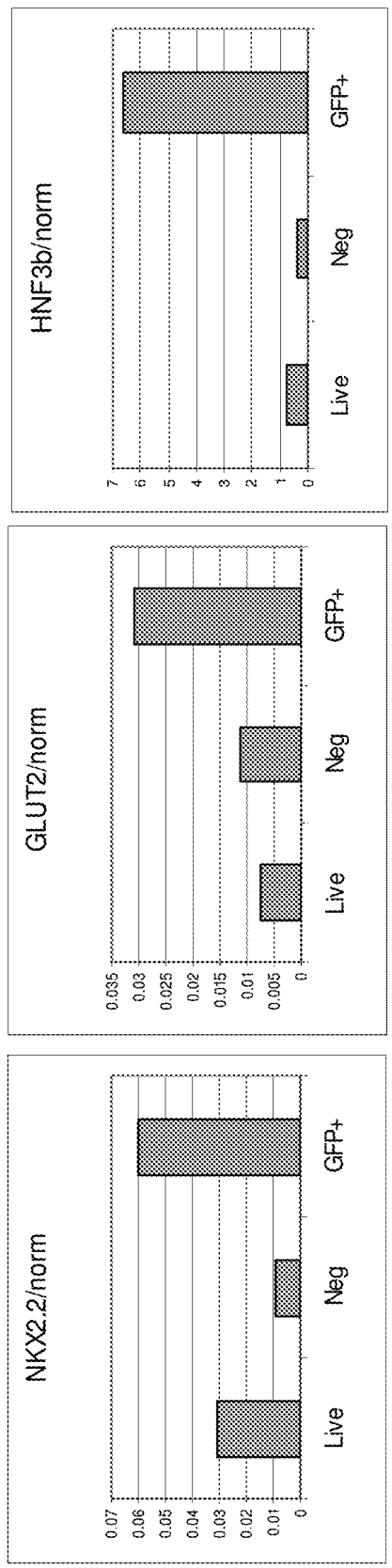
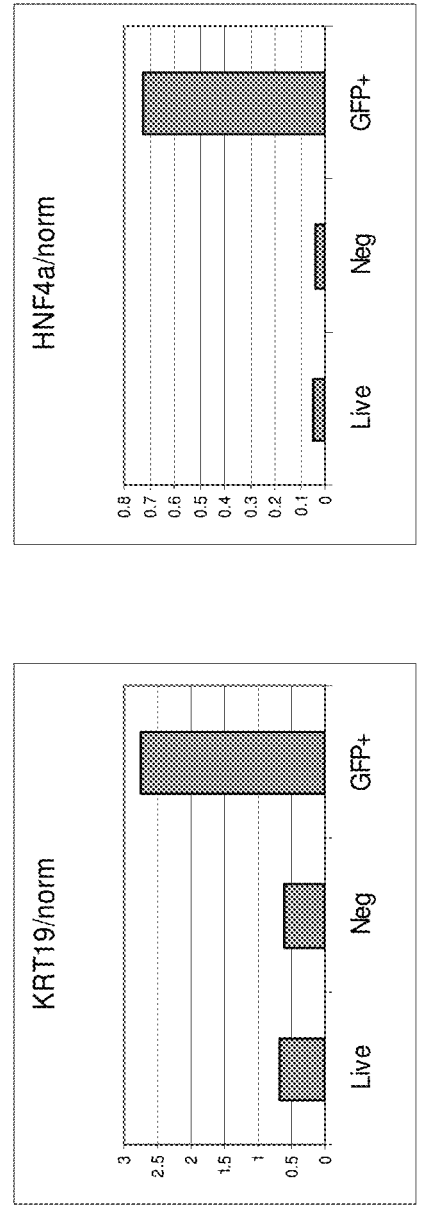
FIG. 48A
FIG. 48B
FIG. 48C
FIG. 48D
FIG. 48E

PDX1 POSITIVE FOREGUT ENDODERM CELLS AND METHODS OF PRODUCTION

CROSS REFERENCE TO RELATED APPLICATIONS

This application is a continuation of U.S. patent application Ser. No. 16/177,235, filed on Oct. 31, 2018, which is a continuation of U.S. patent application Ser. No. 14/947,999, filed on Nov. 20, 2015, which is a continuation of U.S. patent application Ser. No. 14/146,510, filed on Jan. 2, 2014, issued as U.S. Pat. No. 9,222,069, which is a continuation of U.S. patent application Ser. No. 11/587,735, filed on Aug. 29, 2008, issued as U.S. Pat. No. 8,647,873, which is the § 371 U.S. national stage of International Application No. PCT/US2005/014239, filed Apr. 26, 2005, which was published in English under PCT Article 21(2). U.S. patent application Ser. No. 11/587,735 is a continuation-in-part of U.S. patent application Ser. No. 11/021,618, filed Dec. 23, 2004, issued as U.S. Pat. No. 7,510,876. International Application No. PCT/US2005/014239 also claims the benefit of the following three provisional patent applications: U.S. Provisional Patent Application No. 60/566,293, filed Apr. 27, 2004; U.S. Provisional Patent Application No. 60/587,942, filed Jul. 14, 2004; and U.S. Provisional Patent Application No. 60/586,566, filed Jul. 9, 2004.

FIELD OF THE INVENTION

The present invention relates to the fields of medicine and cell biology. In particular, the present invention relates to compositions comprising mammalian PDX1-positive endoderm cells and methods of making, isolating and using such cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases for the treatment of diabetes. However, presently it is not known how to generate an insulin-producing β-cell from hESCs. As such, current cell therapy treatments for diabetes mellitus, which utilize islet cells from donor pancreases, are limited by the scarcity of high quality islet cells needed for transplant. Cell therapy for a single Type I diabetic patient requires a transplant of approximately $8 \times 10^8$ pancreatic islet cells. (Shapiro et al., 2000; Shapiro et al., 2001a; Shapiro et al., 2001b). As such, at least two healthy donor organs are required to obtain sufficient islet cells for a successful transplant. Human embryonic stem cells offer a source of starting material from which to develop substantial quantities of high quality differentiated cells for human cell therapies.

Two properties that make hESCs uniquely suited to cell therapy applications are pluripotence and the ability to maintain these cells in culture for prolonged periods. Pluripotency is defined by the ability of hESCs to differentiate to derivatives of all 3 primary germ layers (endoderm, mesoderm, ectoderm) which, in turn, form all somatic cell types of the mature organism in addition to extraembryonic tissues (e.g. placenta) and germ cells. Although pluripotency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies. Additionally, success in evaluating production of any given cell type depends critically on defining appropriate markers. Achieving efficient, directed differentiation is of great importance for therapeutic application of hESCs.

In order to use hESCs as a starting material to generate cells that are useful in cell therapy applications, it would be advantageous to overcome the foregoing problems. For example, in order to achieve the level of cellular material required for islet cell transplantation therapy, it would be advantageous to efficiently direct hESCs toward the pancreatic islet/β-cell lineage at the very earliest stages of differentiation.

In addition to efficient direction of the differentiation process, it would also be beneficial to isolate and characterize intermediate cell types along the differentiation pathway towards the pancreatic islet/β-cell lineage and to use such cells as appropriate lineage precursors for further steps in the differentiation.

SUMMARY OF THE INVENTION

Embodiments of the present invention relate to compositions comprising PDX1-expressing (PDX1-positive) endoderm cells as well as methods for producing the same. Additional embodiments relate to cell populations enriched in PDX1-positive endoderm and methods for the production of such cell populations. Other embodiments relate to methods of increasing the expression of PDX1 in endoderm cells as well as identifying factors useful for further differentiating PDX1-negative and/or PDX1-positive endoderm. In some embodiments of the compositions and methods described throughout this application, the PDX1-positive endoderm cells are PDX1-positive foregut/midgut endoderm cells. In certain preferred embodiments of the compositions and methods described throughout this application, the PDX1-positive endoderm cells are PDX1-positive foregut endoderm cells. In other preferred embodiments, the PDX1-positive endoderm cells are PDX1-positive endoderm cells of the posterior portion of the foregut.

Some embodiments of the present invention relate to cell cultures comprising PDX1-positive foregut endoderm cells, wherein the PDX1-positive foregut endoderm cells are multipotent cells that can differentiate into cells, tissues or organs derived from the anterior portion of the gut tube. In some embodiments, the cell cultures comprise human cells. In such human cell cultures, PDX1-positive foregut endoderm can comprise at least about 2%, at least about 5%, at least about 10% or at least about 25% of the human cells in the culture. In some embodiments, the at least about 2%, the at least about 5%, the at least about 10% or the at least about 25% is calculated without respect to any feeder cells present in said culture. The PDX1-positive foregut endoderm cells in certain embodiments of the cell cultures described herein can express a marker selected from the group consisting of the homeobox A13 (HOXA13) gene, the homeobox C6 (HOXC6) gene and SOX17. In other embodiments, cell cultures comprising PDX1-positive foregut endoderm cells are substantially free of visceral endoderm cells, parietal endoderm cells and/or neural cells. In some embodiments, the cell cultures further comprise one of more of the following: a retinoid compound, such as retinoic acid (RA), FGF-10 or B27.

Additional embodiments of the present invention relate to enriched, isolated or substantially purified PDX1-positive foregut endoderm cell populations, wherein the PDX1-positive foregut endoderm cells are multipotent cells that can differentiate into cells, tissues or organs derived from the anterior portion of the gut tube. In some embodiments, the PDX1-positive foregut endoderm cells are derived from pluripotent cells, such as human embryonic stem cells. Other embodiments of the present invention, relate to a cell population which comprises cells, wherein at least about 90% of the cells are PDX1-positive foregut endoderm cells, and wherein the PDX1-positive foregut endoderm cells are multipotent cells that can differentiate into cells, tissues or organs derived from the anterior portion of the gut tube. In preferred embodiments, the PDX-1 positive foregut endoderm cells comprise at least about 95% of the cells in the cell population. In even more preferred embodiments, the PDX1-positive foregut endoderm cells comprise at least about 98% of the cells in the cell population.

Further embodiments described herein relate to methods of producing PDX1-positive foregut endoderm cells by providing a cell culture or cell population comprising definitive endoderm cells which do not substantially express PDX1 (PDX1-negative definitive endoderm cells) with a foregut differentiation factor, such as a retinoid. The retinoid, for example RA, can be supplied in a concentration ranging from about 0.01 µM to about 50 µM. In some embodiments, the differentiation of PDX1-negative definitive endoderm to PDX1 positive foregut endoderm is increased by providing the cell culture or cell population with FGF-10 and/or B27. FGF-10 can be supplied in a concentration ranging from about 5 ng/ml to about 1000 ng/ml. In some embodiments, B27 is supplied to the cell culture or cell population at a concentration ranging from about 0.1% to about 20%. FGF-10 and/or B27 can be added to the cell culture or cell population at about the same time as the retinoid or each of the factors may be added separately with up to several hours between each addition. In certain embodiments, the retinoid is added to an approximately 4-day-old PDX1-negative definitive endoderm culture. In some embodiments, the retinoid is added to an approximately 5-day-old PDX1-negative definitive endoderm culture.

Still other embodiments relate to methods of using a foregut differentiation factor to further increase the production of PDX1-positive foregut endoderm cells in a cell culture or cell population that has been contacted with a retinoid, such as RA. In such embodiments, the differentiation of PDX1-negative definitive endoderm to PDX1 positive foregut endoderm is increased by providing the cell culture or cell population with activin A and/or activin B. Activin A and/or activin B can be supplied in a concentration ranging from about 5 ng/ml to about 1000 ng/ml. Other embodiments relate to methods of increasing the production of PDX1-positive foregut endoderm cells in a cell culture or cell population by differentiating PDX1-negative cells in a medium comprising a retinoid, wherein the medium has been previously conditioned by the maintenance or growth of certain cell types. Such cell types include, but are not limited to, embryonic stem cells or other pluripotent cells that have been differentiated in medium comprising serum or members of the TGFβ superfamily of growth factors, such as activin A, activin B, Nodal and/or bone morphogenic protein (BMP). In some embodiments, conditioned medium is supplied to the cell culture or cell population at a concentration ranging from about 1% to about 100% of the entire growth medium. TGFβ superfamily growth factors and/or conditioned medium can be added to the cell culture or cell population at about the same time as the retinoid or each of the factors may be added separately with up to several hours between each addition.

Embodiments of the present invention also relate to methods of producing a cell population enriched in PDX1-positive foregut endoderm cells. In certain embodiments, these methods comprise the step of obtaining a population of pluripotent cells, wherein at least one cell of the pluripotent cell population comprises at least one copy of a nucleic acid that is under the control of the PDX1 promoter. In some embodiments, the nucleic acid comprises a sequence encoding green fluorescent protein (GFP) or a biologically active fragment thereof. In other embodiments, additional method steps include, differentiating the pluripotent cells so as to produce PDX1-positive foregut endoderm cells, wherein the PDX1-positive foregut endoderm cells are multipotent cells that can differentiate into cells, tissues or organs derived from the anterior portion of the gut tube, and separating PDX1-positive cells from PDX1-negative cells. In some embodiments of the methods described herein, the differentiation step further comprises providing the pluripotent cell population with at least one growth factor of the TGFβ superfamily in an amount sufficient to promote differentiation of the pluripotent cells to PDX1-negative definitive endoderm cells, and providing the PDX1-negative definitive endoderm cells with a foregut differentiation factor in an amount sufficient to promote differentiation of the PDX1-negative definitive endoderm cells to PDX1-positive endoderm cells of the foregut.

Some embodiments of the present invention relate to a method of increasing the expression of the PDX1 gene product in SOX17-expressing (SOX17-positive) definitive endoderm cells by contacting such cells with a differentiation factor in an amount that is sufficient to increase the expression of the PDX1 gene product. In some embodiments, the differentiation factor is selected from the group consisting of RA, FGF-10 and B27.

Additional embodiments of the present invention relate to a method of identifying a differentiation factor capable of promoting the differentiation of PDX1-negative definitive endoderm cells to PDX1-positive foregut endoderm cells. In such methods, PDX1-negative definitive endoderm cells are contacted with a candidate differentiation factor and it is determined whether PDX1 expression in the cell population after contact with the candidate differentiation factor has increased as compared to PDX1 expression in the cell population before contact with the candidate differentiation factor. An increase in the PDX1 expression in the cell population indicates that the candidate differentiation factor is capable of promoting the differentiation of PDX1-negative definitive endoderm cells to PDX1-positive foregut endoderm cells. In some embodiments, PDX1 expression is determined by quantitative polymerase chain reaction (Q-PCR). Some embodiments of the foregoing method further comprise the step of determining expression of the HOXA13 and/or the HOXC6 gene in the cell population before and after contact with the candidate differentiation factor. In some embodiments, the candidate differentiation factor is a small molecule, for example, a retinoid, such as RA. In others, the candidate differentiation factor is a polypeptide, for example, a growth factor, such as FGF-10.

Still other embodiments of the present invention relate to a method of identifying a differentiation factor capable of promoting the differentiation of PDX1-positive foregut endoderm cells. In such methods, PDX1-positive foregut endoderm cells are contacted with a candidate differentiation factor and it is determined whether expression of a marker in the population is increased or decreased after contact with the candidate differentiation factor as compared to the expression of the same marker in the population before contact with the candidate differentiation factor. An increase or decrease in the expression of the marker indicates that the candidate differentiation factor is capable of promoting the differentiation of PDX1-positive foregut endoderm cells. In some embodiments, marker expression is determined by Q-PCR. In some embodiments, the candidate differentiation factor is a small molecule, for example, a retinoid, such as RA. In others, the candidate differentiation factor is a polypeptide, for example, a growth factor, such as FGF-10.

In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. A cell culture comprising human cells wherein at least about 2% of said human cells are pancreatic-duodenal homoebox factor-1 (PDX1) positive foregut endoderm cells, said PDX1-positive foregut endoderm cells being multipotent cells that can differentiate into cells, tissues or organs derived from the anterior portion of the gut tube.

2. The cell culture of paragraph 1, wherein at least about 5% of said human cells are PDX1-positive foregut endoderm cells.

3. The cell culture of paragraph 1, wherein at least about 10% of said human cells are PDX1-positive foregut endoderm cells.

4. The cell culture of paragraph 1, wherein at least about 25% of said human cells are PDX1-positive foregut endoderm cells.

5. The cell culture of paragraph 1, wherein human feeder cells are present in said culture, and wherein at least about 2% of human cells other than said human feeder cells are PDX1-positive foregut endoderm cells.

6. The cell culture of paragraph 1, wherein said PDX1-positive foregut endoderm cells express the homeobox A13 (HOXA13) gene.

7. The cell culture of paragraph 1, wherein said PDX1-positive foregut endoderm cells express the homeobox C6 (HOXC6) gene.

8. The cell culture of paragraph 1, wherein said PDX1-positive foregut endoderm cells express SOX17.

9. The cell culture of paragraph 1, wherein the expression of PDX1 is greater than the expression of a marker selected from the group consisting of alpha-fetoprotein (AFP), SOX7, SOX1, ZIC1 and NFM in said PDX1-positive foregut endoderm cells.

10. The cell culture of paragraph 1, wherein said cell culture is substantially free of cells selected from the group consisting of visceral endodermal cells, parietal endodermal cells and neural cells.

11. The cell culture of paragraph 1, wherein at least about 1 PDX1-positive foregut endoderm cell is present for about every 10 PDX1-negative definitive endoderm cells in said cell culture.

12. The cell culture of paragraph 1, wherein at least about 1 PDX1-positive foregut endoderm cell is present for about every 5 PDX1-negative definitive endoderm cells in said cell culture.

13. The cell culture of paragraph 1, wherein at least about 1 PDX1-positive foregut endoderm cell is present for about every 4 PDX1-negative definitive endoderm cells in said cell culture.

14. The cell culture of paragraph 1 further comprising an embryonic stem cell.

15. The cell culture of paragraph 14, wherein said embryonic stem cell is derived from a tissue selected from the group consisting of the morula, the inner cell mass (ICM) of an embryo and the gonadal ridges of an embryo.

16. The cell culture of paragraph 1 further comprising a retinoid.

17. The cell culture of paragraph 16, wherein said retinoid is retinoic acid (RA).

18. The cell culture of paragraph 1 further comprising FGF-10.

19. The cell culture of paragraph 1 further comprising B27.

20. The cell culture of paragraph 1 further comprising both RA and FGF-10.

21. The cell culture of paragraph 20 further comprising B27.

22. A cell population comprising cells wherein at least about 90% of said cells are human PDX1-positive foregut endoderm cells, said PDX1-positive foregut endoderm cells being multipotent cells that can differentiate into cells, tissues or organs derived from the anterior portion of the gut tube.

23. The cell population of paragraph 22, wherein at least about 95% of said cells are PDX1-positive foregut endoderm cells.

24. The cell population of paragraph 22, wherein at least about 98% of said cells are PDX1-positive foregut endoderm cells.

25. The cell population of paragraph 22, wherein said PDX1-positive foregut endoderm cells express the HOXA13 gene.

26. The cell population of paragraph 22, wherein said PDX1-positive foregut endoderm cells express the HOXC6 gene.

27. The cell population of paragraph 22, wherein said PDX1-positive foregut endoderm cells express SOX17.

28. The cell population of paragraph 22, wherein the expression of PDX1 is greater than the expression of a marker selected from the group consisting of AFP, SOX7, SOX1, ZIC1 and NFM in said PDX1-positive foregut endoderm cells.

29. A method of producing PDX1-positive foregut endoderm cells, said method comprising the steps of obtaining a cell population comprising PDX1-negative definitive endoderm cells and providing said cell population with a retinoid in an amount sufficient to promote differentiation of at least a portion of said PDX1-negative definitive endoderm cells to PDX1-positive foregut endoderm cells, wherein said PDX1-positive foregut endoderm cells are multipotent cells that can differentiate into cells, tissues or organs derived from the anterior portion of the gut tube.

30. The method of paragraph 29 further comprising the step of allowing sufficient time for PDX1-positive foregut endoderm cells to form, wherein said sufficient time for PDX1-positive foregut endoderm cells to form has been determined by detecting the presence of PDX1-positive foregut endoderm cells in said cell population.

31. The method of paragraph 29, wherein at least about 2% of said PDX1-negative definitive endoderm cells differentiate into PDX1-positive foregut endoderm cells.

32. The method of paragraph 29, wherein at least about 5% of said PDX1-negative definitive endoderm cells differentiate into PDX1-positive foregut endoderm cells.

33. The method of paragraph 29, wherein at least about 10% of said PDX1-negative definitive endoderm cells differentiate into PDX1-positive foregut endoderm cells.

34. The method of paragraph 29, wherein at least about 25% of said PDX1-negative definitive endoderm cells differentiate into PDX1-positive foregut endoderm cells.

35. The method of paragraph 29, wherein detecting the presence of PDX1-positive foregut endoderm cells in said cell population comprises detecting the expression of PDX1.

36. The method of paragraph 35, wherein the expression of PDX1 is greater than the expression of a marker selected from the group consisting of alpha-fetoprotein (AFP), SOX7, SOX1, ZIC1 and NFM in said PDX1-positive foregut endoderm cells.

37. The method of paragraph 35, wherein the expression of said PDX1 is determined by quantitative polymerase chain reaction (Q-PCR).

38. The method of paragraph 35, wherein the expression of PDX1 is determined by immunocytochemistry.

39. The method of paragraph 29, wherein said retinoid is RA.

40. The method of paragraph 39, wherein RA is provided in a concentration ranging from about 0.01 μM to about 50 μM.

41. The method of paragraph 39, wherein RA is provided in a concentration ranging from about 0.04 μM to about 20 μM.

42. The method of paragraph 39, wherein RA is provided in a concentration ranging from about 0.1 μM to about 10 μM.

43. The method of paragraph 39, wherein RA is provided in a concentration ranging from about 0.2 μM to about 2.5 μM.

44. The method of paragraph 39, wherein RA is provided in a concentration ranging from about 0.5 μM to about 1.5 μM.

45. The method of paragraph 39, wherein RA is provided in a concentration of about 1 μM.

46. The method of paragraph 39, wherein RA is provided when said culture is about 4-days-old.

47. The method of paragraph 29 further comprising providing to said culture a factor selected from the group consisting of FGF-10, FGF-4, activin A, activin B, B27, conditioned medium, and combinations of said factors in an amount sufficient to enhance the production of PDX1-positive foregut endoderm cells.

48. The method of paragraph 47, wherein said factor is selected from the group consisting of FGF-10, FGF-4, activin A and activin B.

49. The method of paragraph 48, wherein said factor is provided in a concentration ranging from about 10 ng/ml to about 500 ng/ml.

50. The method of paragraph 48, wherein said factor is provided in a concentration ranging from about 20 ng/ml to about 200 ng/ml.

51. The method of paragraph 48, wherein said factor is provided in a concentration ranging from about 25 ng/ml to about 75 ng/ml.

52. The method of paragraph 48, wherein said factor is provided in a concentration about 50 ng/ml.

53. The method of paragraph 48, wherein said factor is provided at approximately the same time as said retinoid.

54. The method of paragraph 47 wherein said factor is B27.

55. The method of paragraph 54, wherein B27 is provided in a concentration ranging from about 0.1% to about 20% of the total medium.

56. The method of paragraph 54, wherein B27 is provided in a concentration ranging from about 0.2% to about 5% of the total medium.

57. The method of paragraph 54, wherein B27 is provided in a concentration ranging from 0.5% to about 2% of the total medium.

58. The method of paragraph 54, wherein B27 is provided in a concentration of about 1% of the total medium.

59. The method of paragraph 54, wherein B27 is provided at approximately the same time as said retinoid.

60. The method of paragraph 47 wherein said factor is conditioned medium.

61. The method of paragraph 60, wherein conditioned medium is provided in a concentration ranging from about 10% to about 100% of the total medium.

62. The method of paragraph 60, wherein conditioned medium is provided in a concentration ranging from about 20% to about 80% of the total medium.

63. The method of paragraph 60, wherein conditioned medium is provided in a concentration ranging from about 40% to about 60% of the total medium.

64. The method of paragraph 60, wherein conditioned medium is provided in a concentration of about 50% of the total medium.

65. The method of paragraph 60, wherein conditioned medium is provided at approximately the same time as said retinoid.

66. The method of paragraph 60, wherein conditioned medium is prepared by contacting differentiated human embryonic stem cells (hESCs) with a cell culture medium for about 24 hours.

67. The method of paragraph 66, wherein said hESCs are differentiated for about 5 days in a cell culture medium selected from the group consisting of RPMI supplemented with 3% serum, low serum RPMI supplemented with activin A and low serum RPMI supplemented with BMP4.

68. A PDX1-positive foregut endoderm cell produced by the method of paragraph 29.

69. A method of producing a cell population enriched in PDX1-positive foregut endoderm cells, said method comprising the steps of obtaining a population of pluripotent cells, wherein at least one cell of said pluripotent cell population comprises at least one copy of a nucleic acid under the control of the PDX1 promoter, said nucleic acid comprising a sequence encoding green fluorescent protein (GFP) or a biologically active fragment thereof, differentiating said pluripotent cells so as to produce PDX1-positive foregut endoderm cells, said PDX1-positive foregut endoderm cells being multipotent cells that can differentiate into cells, tissues or organs derived from the anterior portion of the gut tube and separating said PDX1-positive foregut endoderm cells from PDX1-negative cells.

70. The method of paragraph 69, wherein said enriched cell population comprises at least about 95% PDX1-positive foregut endoderm cells.

71. The method of paragraph 69, wherein said enriched cell population comprises at least about 98% PDX1-positive foregut endoderm cells.

72. The method of paragraph 69, wherein the differentiating step further comprises, providing said pluripotent cell population with at least one growth factor of the TGFβ superfamily in an amount sufficient to promote differentiation of said pluripotent cells to PDX1-negative definitive endoderm cells, and providing said PDX1-negative definitive endoderm cells with a retinoid in an amount sufficient to promote differentiation of said PDX1-negative definitive endoderm cells to PDX1-positive foregut endoderm cells.

73. The method of paragraph 72, wherein said retinoid is RA.

74. An enriched population of PDX1-positive foregut endoderm cells produced by the method of paragraph 69.

75. A method of increasing the expression of the PDX1 gene product in a SOX17 expressing definitive endoderm cell, said method comprising contacting said definitive endoderm cell with a differentiation factor in an amount sufficient to increase expression of the PDX1 gene product.

76. The method of paragraph 75, wherein said differentiation factor is a retinoid.

77. The method of paragraph 76, wherein said differentiation factor is RA.

78. The method of paragraph 75, wherein said differentiation factor is selected from the group consisting of FGF-10, FGF-4, activin A, activin B, B27, conditioned medium and combinations of said factors.

79. A method of identifying a differentiation factor capable of promoting the differentiation of PDX1-negative definitive endoderm cells to PDX1-positive foregut endoderm cells, said method comprising the steps of obtaining a population comprising PDX1-negative definitive endoderm cells, contacting said population comprising PDX1-negative definitive endoderm cells with a candidate differentiation factor and determining if PDX1 expression in said cell population after contact with said candidate differentiation factor has increased as compared to PDX1 expression in said cell population before contact with said candidate differentiation factor, wherein an increase in said PDX1 expression in said cell population indicates that said candidate differentiation factor is capable of promoting the differentiation of PDX1-negative definitive endoderm cells to PDX1-positive foregut endoderm cells, said PDX1-positive foregut endoderm cells being multipotent cells that can differentiate into cells, tissues or organs derived from the anterior portion of the gut tube.

80. The method of paragraph 79, wherein said PDX1 expression is determined by Q-PCR.

81. The method of paragraph 79 further comprising the step of determining the expression of the HOXA13 gene in said cell population before and after contact with said candidate differentiation factor.

82. The method of paragraph 79 further comprising the step of determining the expression of the HOXC6 gene in said cell population before and after contact with said candidate differentiation factor.

83. The method of paragraph 79, wherein said candidate differentiation factor is a small molecule.

84. The method of paragraph 83, wherein said small molecule is a retinoid.

85. The method of paragraph 84, wherein said retinoid is RA.

86. The method of paragraph 79, wherein said candidate differentiation factor is a polypeptide.

87. The method of paragraph 79, wherein said candidate differentiation factor is a growth factor.

88. The method of paragraph 79, wherein said candidate differentiation factor is FGF-10.

89. A method of identifying a differentiation factor capable of promoting the differentiation of PDX1-positive foregut endoderm cells, said method comprising the steps of obtaining a population comprising PDX1-positive foregut endoderm cells, contacting said population comprising PDX1-positive foregut endoderm cells with a candidate differentiation factor and determining if expression of a marker in said population is increased or decreased after contact with said candidate differentiation factor, as compared to expression of the same marker in said population before contact with said candidate differentiation factor, wherein an increase or decrease in expression of said marker in said population indicates that said candidate differentiation factor is capable of promoting the differentiation of PDX1-positive foregut endoderm cells.

90. The method of paragraph 81, wherein said marker expression is determined by Q-PCR.

91. The method of paragraph 81, wherein said candidate differentiation factor is a small molecule.

92. The method of paragraph 81, wherein said candidate differentiation factor is a polypeptide.

93. The method of paragraph 81, wherein said candidate differentiation factor is a growth factor.

94. A vector comprising a reporter gene operably linked to a PDX1 control region.

95. The vector of paragraph 94, wherein said reporter gene is EGFP.

96. A cell comprising the vector of paragraph 94.

97. A cell comprising a reporter gene operably linked to a PDX1 control region.

98. The cell of paragraph 97, wherein said reporter gene operably linked to said PDX1 control region is integrated into a chromosome.

99. The cell of paragraph 97, wherein said reporter gene is EGFP.

100. The cell of paragraph 97, wherein said cell is pluripotent.

101. The cell of paragraph 100, wherein said cell is a hESC.

102. The cell of paragraph 97, wherein said cell is a definitive endoderm cell.

103. The cell of paragraph 97, wherein said cell is a PDX1-positive foregut endoderm cell.

104. A conditioned medium prepared by the steps of contacting fresh cell culture medium with a population of differentiated hESCs for about 24 hours, wherein said hESCs have been differentiated for about 5 days in a cell culture medium selected from the group consisting of RPMI supplemented with 3% serum, low serum RPMI supplemented with activin A and low serum RPMI supplemented with BMP4 and removing said population of differentiated hESCs from the medium.

105. The conditioned medium of paragraph 104, wherein said fresh cell culture medium is RPMI.

106. The conditioned medium of paragraph 105, wherein said RPMI is low serum RPMI.

107. A method for conditioning medium, said method comprising the steps of contacting fresh cell culture medium with a population of differentiated hESCs for about 24 hours, wherein said hESCs have been differentiated for about 5 days in a cell culture medium selected from the group consisting of RPMI supplemented with 3% serum, low serum RPMI supplemented with activin A and low serum RPMI supplemented with BMP4 and removing said population of differentiated hESCs from the medium.

108. The method of paragraph 107, wherein said fresh cell culture medium is RPMI.

109. The method of paragraph 108, wherein said RPMI is low serum RPMI.

It will be appreciated that the methods and compositions described above relate to cells cultured in vitro. However, the above-described in vitro differentiated cell compositions may be used for in vivo applications.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; and U.S. patent application Ser. No. 11/021,618, entitled DEFINITIVE ENDODERM, filed Dec. 23, 2004, the disclosures of which are incorporated herein by reference in their entireties.

BRIEF DESCRIPTION OF THE DRAWINGS

FIGS. 6A-6C are micrographs showing parietal endoderm and SOX17. Panel A shows immunocytochemistry for human Thrombomodulin (TM) protein located on the cell surface of parietal endoderm cells in randomly differentiated cultures of hES cells. Panel B is the identical field shown in A double-labeled for TM and SOX17. Panel C is the phase contrast image of the same field with DAPI labeled nuclei. Note the complete correlation of DAPI labeled nuclei and SOX17 labeling.

FIGS. 10A-10F are micrographs which show that exposure of hESCs to nodal, activin A and activin B (NAA) yields a striking increase in the number of SOX17$^+$ cells over the period of 5 days (A-C). By comparing to the relative abundance of SOX17$^+$ cells to the total number of cells present in each field, as indicated by DAPI stained nuclei (D-F), it can be seen that approximately 30-50% of all cells are immunoreactive for SOX17 after five days treatment with NAA.

FIGS. 16A-16D are micrographs which show marker expression in response to treatment with activin A and activin B. hESCs were treated for four consecutive days with activin A and activin B and triple labeled with SOX17, AFP and TM antibodies. Panel A—SOX17; Panel B—AFP; Panel C—TM; and Panel D—Phase/DAPI. Notice the numerous SOX17 positive cells (A) associated with the complete absence of AFP (B) and TM (C) immunoreactivity.

FIGS. 25A-25D are micrographs which show $SOX17^+$ cells are dividing in culture. SOX17 immunoreactive cells are present at the differentiating edge of an hESC colony (C, D) and are labeled with proliferating cell nuclear antigen (PCNA) (panel B) yet are not co-labeled with OCT4 (panel C). In addition, clear mitotic figures can be seen by DAPI labeling of nuclei in both $SOX17^+$ cells (arrows) as well as $OCT4^+$, undifferentiated hESCs (arrowheads) (D).

FIGS. 29A-29F are micrographs that show the relative difference in SOX17 immunoreactive cells across three of the media conditions displayed in FIGS. 26-28.

FIGS. 48A-48E are charts showing the relative expression levels normalized to housekeeping genes of five pancreatic endoderm markers in sorted populations of live cells (Live), EGFP-negative cells (Neg) and EGFP-positive cells (GFP+). Panels: A—NKX2.2; B—GLUT2; C—HNF3β; D—KRT19 and E—HNF4α.

SEQUENCE LISTING

Figure 1:
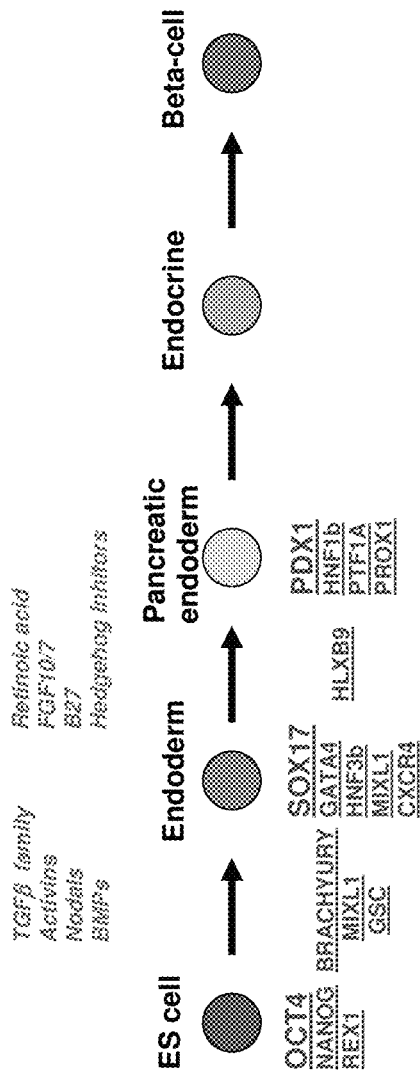
FIG. 1 is a schematic of a proposed differentiation pathway for the production of beta-cells from hESCs. The first step in the pathway commits the ES cell to the definitive endoderm lineage and also represents the first step prior to further differentiation events to pancreatic endoderm, endocrine endoderm, or islet/beta-cells. The second step in the pathway shows the conversion of SOX17-positive/PDX1-negative definitive endoderm to PDX1-positive foregut endoderm. Some factors useful for mediating these transitions are italicized. Relevant markers for defining the target cells are underlined.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand when appropriate. The Sequence Listing is submitted as an ASCII text file [9511-96321-08_Sequence_Listing.txt, Sep. 19, 2019, 5.84 KB], which is incorporated by reference herein.

DETAILED DESCRIPTION

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extra-cellular matrix material of Reichert's membrane. During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

The PDX1 Gene Expression During Development

PDX1 (also called STF-1, IDX-1 and IPF-1) is a transcription factor that is necessary for development of the pancreas and rostral duodenum. PDX1 is first expressed in the pancreatic endoderm, which arises from posterior foregut endoderm and will produce both the exocrine and endocrine cells, starting at E8.5 in the mouse. Later, PDX1 becomes restricted to beta-cells and some delta-cells. This expression pattern is maintained in the adult. PDX1 is also expressed in duodenal endoderm early in development, which is adjacent to the forming pancreas, then in the duodenal enterocytes and enteroendocrine cells, antral stomach and in the common bile, cystic and biliary ducts. This region of expression also becomes limited, at the time that pancreatic expression becomes restricted, to predominantly the rostral duodenum.

PDX1-Positive Cells and Processes Related Thereto

Embodiments of the present invention relate to novel, defined processes for the production of PDX1-positive endoderm cells, wherein the PDX1-positive endoderm cells are multipotent cells that can differentiate into cells, tissues or organs derived from the foregut/midgut region of the gut tube (PDX1-positive foregut/midgut endoderm). As used herein, "multipotent" or "multipotent cell" refers to a cell type that can give rise to a limited number of other particular cell types. As used herein, "foregut/midgut" refers to cells of the anterior portion of the gut tube as well as cells of the middle portion of the gut tube, including cells of the foregut/midgut junction.

Some preferred embodiments of the present invention relate to processes for the production of PDX1-positive foregut endoderm cells. In some embodiments, these PDX1-positive foregut endoderm cells are multipotent cells that can differentiate into cells, tissues or organs derived from the anterior portion of the gut tube (PDX1-positive foregut endoderm).

Additional preferred embodiments relate to processes for the production of PDX1-positive endoderm cells of the posterior portion of the foregut. In some embodiments, these PDX1-positive endoderm cells are multipotent cells that can differentiate into cells, tissues or organs derived from the posterior portion of the foregut region of the gut tube.

The PDX1-positive foregut endoderm cells, such as those produced according to the methods described herein, can be used to produce fully differentiated insulin-producing β-cells. In some embodiments of the present invention, PDX1-positive foregut endoderm cells are produced by differentiating definitive endoderm cells that do not substantially express PDX1 (PDX1-negative definitive endoderm cells; also referred to herein as definitive endoderm) so as to form PDX1-positive foregut endoderm cells. PDX1-negative definitive endoderm cells can be prepared by differentiating pluripotent cells, such as embryonic stem cells, as described herein or by any other known methods. A convenient and highly efficient method for producing PDX1-negative definitive endoderm from pluripotent cells is described in U.S. patent Ser. No. 11/021,618, entitled DEFINITIVE ENDODERM, filed Dec. 23, 2004, the disclosure of which is incorporated herein by reference in its entirety.

Processes of producing PDX1-positive foregut endoderm cells provide a basis for efficient production of pancreatic tissues such as acinar cells, ductal cells and islet cells from pluripotent cells. In certain preferred embodiments, human PDX1-positive foregut endoderm cells are derived from human PDX1-negative definitive endoderm cells, which in turn, are derived from hESCs. These human PDX1-positive foregut endoderm cells can then be used to produce functional insulin-producing β-cells. To obtain useful quantities of insulin-producing β-cells, high efficiency of differentiation is desirable for each of the differentiation steps that occur prior to reaching the pancreatic islet/β-cell fate. Because differentiation of PDX1-negative definitive endoderm cells to PDX1-positive foregut endoderm cells represents an early step towards the production of functional pancreatic islet/β-cells (as shown in FIG. 1), high efficiency of differentiation at this step is particularly desirable.

In view of the desirability of efficient differentiation of PDX1-negative definitive endoderm cells to PDX1-positive foregut endoderm cells, some aspects of the present invention relate to in vitro methodology that results in approximately 2-25% conversion of PDX1-negative definitive endoderm cells to PDX1-positive foregut endoderm cells. Typically, such methods encompass the application of culture and growth factor conditions in a defined and temporally specified fashion. Further enrichment of the cell population for PDX1-positive foregut endoderm cells can be achieved by isolation and/or purification of the PDX1-positive foregut endoderm cells from other cells in the population by using a reagent that specifically binds to the PDX1-positive foregut endoderm cells. As an alternative, PDX1-positive foregut endoderm cells can be labeled with a reporter gene, such as green fluorescent protein (GFP), so as to enable the detection of PDX1 expression. Such fluorescently labeled cells can then be purified by fluorescent activated cell sorting (FACS). Further aspects of the present invention relate to cell cultures and enriched cell populations comprising PDX1-positive foregut endoderm cells as well as methods for identifying factors useful in the differentiation to and from PDX1-positive foregut endoderm.

In order to determine the amount of PDX1-positive foregut endoderm cells in a cell culture or cell population, a method of distinguishing this cell type from the other cells in the culture or in the population is desirable. Accordingly, certain embodiments of the present invention relate to cell markers whose presence, absence and/or relative expression levels are indicative of PDX1-positive foregut endoderm cells as well as methods for detecting and determining the expression of such markers. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule (for example, molecules having a molecular weight of less than 10,000 amu).

In some embodiments of the present invention, the presence, absence and/or level of expression of a marker is determined by quantitative PCR (Q-PCR). For example, the amount of transcript produced by certain genetic markers, such as PDX1, SOX17, SOX7, SOX1, ZIC1, NFM, alpha-fetoprotein (AFP), homeobox A13 (HOXA13), homeobox C6 (HOXC6), and/or other markers described herein is determined by Q-PCR. In other embodiments, immunohistochemistry is used to detect the proteins expressed by the above-mentioned genes. In still other embodiments, Q-PCR and immunohistochemical techniques are both used to identify and determine the amount or relative proportions of such markers.

By using the differentiation and detection methods described herein, it is possible to identify PDX1-positive foregut endoderm cells, as well as determine the proportion of PDX1-positive foregut endoderm cells in a cell culture or cell population. For example, in some embodiments of the present invention, the PDX1-positive foregut endoderm cells or cell populations that are produced express the PDX1 gene at a level of at least about 2 orders of magnitude greater than PDX1-negative cells or cell populations. In other embodiments, the PDX1-positive foregut endoderm cells and cell populations that are produced express the PDX1 gene at a level of more than 2 orders of magnitude greater than PDX1-negative cells or cell populations. In still other embodiments, the PDX1-positive foregut endoderm cells or cell populations that are produced express one or more of the markers selected from the group consisting of PDX1, SOX17, HOXA13 and HOXC6 at a level of about 2 or more than 2 orders of magnitude greater than PDX1-negative definitive endoderm cells or cell populations.

The compositions and methods described herein have several useful features. For example, the cell cultures and cell populations comprising PDX1-positive endoderm, as well as the methods for producing such cell cultures and cell populations, are useful for modeling the early stages of human development. Furthermore, the compositions and methods described herein can also serve for therapeutic intervention in disease states, such as diabetes mellitus. For example, since PDX1-positive foregut endoderm serves as the source for only a limited number of tissues, it can be used in the development of pure tissue or cell types.

Production of PDX1-Negative Definitive Endoderm (Definitive Endoderm) from Pluripotent Cells Cell cultures and/or cell populations comprising PDX1-positive foregut endoderm cells are produced from pluripotent cells by first producing PDX1-negative definitive endoderm (also referred to as "definitive endoderm"). Processes for differentiating pluripotent cells to produce cell cultures and enriched cell populations comprising definitive endoderm is described briefly below and in detail in U.S. patent Ser. No. 11/021,618, entitled DEFINITIVE ENDODERM, filed Dec. 23, 2004, the disclosure of which is incorporated herein by reference in its entirety. In some of these processes, the pluripotent cells used as starting material are stem cells. In certain processes, definitive endoderm cell cultures and enriched cell populations comprising definitive endoderm cells are produced from embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. A preferred method for deriving definitive endoderm cells utilizes human embryonic stem cells as the starting material for definitive endoderm production. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843, 780, 6,200,806 and 6,251,671 the disclosures of which are incorporated herein by reference in their entireties.

In some processes for producing definitive endoderm cells, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes for producing definitive endoderm permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. Additionally, the growth factor Wnt3a and other Wnt family members are useful for the production of definitive endoderm cells. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred processes, the growth factors are removed about four days after their addition.

Cultures of definitive endoderm cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or with serum replacement. In still other processes, definitive endoderm cells are grown in the presence of B27. In such processes, the concentration of B27 supplement can range from about 0.1% v/v to about 20% v/v.

Monitoring the Differentiation of Pluripotent Cells to PDX1-Negative Definitive Endoderm (Definitive Endoderm)

The progression of the hESC culture to definitive endoderm can be monitored by determining the expression of markers characteristic of definitive endoderm. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined.

As described further in the Examples below, a reliable marker of definitive endoderm is the SOX17 gene. As such, the definitive endoderm cells produced by the processes described herein express the SOX17 marker gene, thereby producing the SOX17 gene product. Other markers of definitive endoderm are MIXL1, GATA4, HNF3b, GSC, FGF17, VWF, CALCR, FOXQ1, CMKOR1 and CRIP1. Since definitive endoderm cells express the SOX17 marker gene at a level higher than that of the SOX7 marker gene, which is characteristic of primitive and visceral endoderm (see Table 1), in some processes, the expression of both SOX17 and SOX7 is monitored. In other processes, expression of the both the SOX17 marker gene and the OCT4 marker gene, which is characteristic of hESCs, is monitored. Additionally, because definitive endoderm cells express the SOX17 marker gene at a level higher than that of the AFP, SPARC or Thrombomodulin (TM) marker genes, the expression of these genes can also be monitored.

Another marker of definitive endoderm is the CXCR4 gene. The CXCR4 gene encodes a cell surface chemokine receptor whose ligand is the chemoattractant SDF-1. The principal roles of the CXCR4 receptor-bearing cells in the adult are believed to be the migration of hematopoetic cells to the bone marrow, lymphocyte trafficking and the differentiation of various B cell and macrophage blood cell lineages [Kim, C., and Broxmeyer, H. J. Leukocyte Biol. 65, 6-15 (1999)]. The CXCR4 receptor also functions as a coreceptor for the entry of HIV-1 into T-cells [Feng, Y., et al. Science, 272, 872-877 (1996)]. In an extensive series of studies carried out by [McGrath, K. E. et al. Dev. Biology 213, 442-456 (1999)], the expression of the chemokine receptor CXCR4 and its unique ligand, SDF-1 [Kim, C., and Broxmyer, H., J. Leukocyte Biol. 65, 6-15 (1999)], were delineated during early development and adult life in the mouse. The CXCR4/SDF1 interaction in development became apparent when it was demonstrated that if either gene was disrupted in transgenic mice [Nagasawa et al. Nature, 382, 635-638 (1996)], Ma, Q., et al Immunity, 10, 463-471 (1999)] it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germlayer cells and is expressed on definitive endoderm, mesoderm and extraembryonic mesoderm present at this time. In E7.2-7.8 mouse embryos, CXCR4 and alpha-fetoprotein are mutually exclusive indicating a lack of expression in visceral endoderm [McGrath, K. E. et al. Dev. Biology 213, 442-456 (1999)].

Since definitive endoderm cells produced by differentiating pluripotent cells express the CXCR4 marker gene, expression of CXCR4 can be monitored in order to track the production of definitive endoderm cells. Additionally, definitive endoderm cells produced by the methods described herein express other markers of definitive endoderm including, but not limited to, SOX17, MIXL1, GATA4, HNF3b, GSC, FGF17, VWF, CALCR, FOXQ1, CMKOR1 and CRIP1. Since definitive endoderm cells express the CXCR4 marker gene at a level higher than that of the SOX7 marker gene, the expression of both CXCR4 and SOX7 can be monitored. In other processes, expression of the both the CXCR4 marker gene and the OCT4 marker gene, is monitored. Additionally, because definitive endoderm cells express the CXCR4 marker gene at a level higher than that of the AFP, SPARC or Thrombomodulin (TM) marker genes, the expression of these genes can also be monitored.

It will be appreciated that expression of CXCR4 in endodermal cells does not preclude the expression of SOX17. As such, definitive endoderm cells produced by the processes described herein will substantially express SOX17 and CXCR4 but will not substantially express AFP, TM, SPARC or PDX1.

Enrichment, Isolation and/or Purification of Definitive Endoderm

Definitive endoderm cells produced by any of the above-described processes can be enriched, isolated and/or purified by using an affinity tag that is specific for such cells. Examples of affinity tags specific for definitive endoderm cells are antibodies, ligands or other binding agents that are specific to a marker molecule, such as a polypeptide, that is present on the cell surface of definitive endoderm cells but which is not substantially present on other cell types that would be found in a cell culture produced by the methods described herein. In some processes, an antibody which binds to CXCR4 is used as an affinity tag for the enrichment, isolation or purification of definitive endoderm cells. In other processes, the chemokine SDF-1 or other molecules based on SDF-1 can also be used as affinity tags. Such molecules include, but not limited to, SDF-1 fragments, SDF-1 fusions or SDF-1 mimetics.

Methods for making antibodies and using them for cell isolation are known in the art and such methods can be implemented for use with the antibodies and definitive endoderm cells described herein. In one process, an antibody which binds to CXCR4 is attached to a magnetic bead and then allowed to bind to definitive endoderm cells in a cell culture which has been enzymatically treated to reduce intercellular and substrate adhesion. The cell/antibody/bead complexes are then exposed to a movable magnetic field which is used to separate bead-bound definitive endoderm cells from unbound cells. Once the definitive endoderm cells are physically separated from other cells in culture, the antibody binding is disrupted and the cells are replated in appropriate tissue culture medium.

Additional methods for obtaining enriched, isolated or purified definitive endoderm cell cultures or populations can also be used. For example, in some embodiments, the CXCR4 antibody is incubated with a definitive endoderm-containing cell culture that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). CXCR4-positive cells are collected separately from CXCR4-negative cells, thereby resulting in the isolation of such cell types. If desired, the isolated cell compositions can be further purified by using an alternate affinity-based method or by additional rounds of sorting using the same or different markers that are specific for definitive endoderm.

In still other processes, definitive endoderm cells are enriched, isolated and/or purified using a ligand or other molecule that binds to CXCR4. In some processes, the molecule is SDF-1 or a fragment, fusion or mimetic thereof.

In preferred processes, definitive endoderm cells are enriched, isolated and/or purified from other non-definitive endoderm cells after the stem cell cultures are induced to differentiate towards the definitive endoderm lineage. It will be appreciated that the above-described enrichment, isolation and purification procedures can be used with such cultures at any stage of differentiation.

In addition to the procedures just described, definitive endoderm cells may also be isolated by other techniques for cell isolation. Additionally, definitive endoderm cells may also be enriched or isolated by methods of serial subculture in growth conditions which promote the selective survival or selective expansion of the definitive endoderm cells.

Using the methods described herein, enriched, isolated and/or purified populations of definitive endoderm cells and or tissues can be produced in vitro from pluripotent cell cultures or cell populations, such as stem cell cultures or populations, which have undergone at least some differentiation. In some methods, the cells undergo random differentiation. In a preferred method, however, the cells are directed to differentiate primarily into definitive endoderm. Some preferred enrichment, isolation and/or purification methods relate to the in vitro production of definitive endoderm from human embryonic stem cells. Using the methods described herein, cell populations or cell cultures can be enriched in definitive endoderm content by at least about 2- to about 1000-fold as compared to untreated cell populations or cell cultures.

Compositions Comprising PDX1-Negative Definitive Endoderm (Definitive Endoderm)

Cell compositions produced by the above-described methods include cell cultures comprising definitive endoderm and cell populations enriched in definitive endoderm. For example, cell cultures which comprise definitive endoderm cells, wherein at least about 50-80% of the cells in culture are definitive endoderm cells, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to definitive endoderm. In processes in which isolation of definitive endoderm cells is employed, for example, by using an affinity reagent that binds to the CXCR4 receptor, a substantially pure definitive endoderm cell population can be recovered.

Production of PDX1-Positive Foregut Endoderm from PDX1-Negative Definitive Endoderm The PDX1-positive foregut endoderm cell cultures and populations comprising PDX1-positive foregut endoderm cells that are described herein are produced from PDX1-negative definitive endoderm, which is generated from pluripotent cells as described above. A preferred method utilizes human embryonic stem cells as the starting material. In one embodiment, hESCs are first converted to PDX1-negative definitive endoderm cells, which are then converted to PDX1-positive foregut endoderm cells. It will be appreciated, however, that the starting materials for the production of PDX1-positive foregut endoderm is not limited to definitive endoderm cells produced using pluripotent cell differentiation methods. Rather, any PDX1-negative definitive endoderm cells can be used in the methods described herein regardless of their origin.

In some embodiments of the present invention, cell cultures or cell populations comprising PDX1-negative definitive endoderm cells can be used for further differentiation to cell cultures and/or enriched cell populations comprising PDX1-positive foregut endoderm cells. For example, a cell culture or cell population comprising human PDX1-negative, SOX17-positive definitive endoderm cells can be used. In some embodiments, the cell culture or cell population may also comprise differentiation factors, such as activins, nodals and/or BMPs, remaining from the previous differentiation step (that is, the step of differentiating pluripotent cells to definitive endoderm cells). In other embodiments, factors utilized in the previous differentiation step are removed from the cell culture or cell population prior to the addition of factors used for the differentiation of the PDX1-negative, SOX17-positive definitive endoderm cells to PDX1-positive foregut endoderm cells. In other embodiments, cell populations enriched for PDX1-negative, SOX17-positive definitive endoderm cells are used as a source for the production of PDX1-positive foregut endoderm cells.

PDX1-negative definitive endoderm cells in culture are differentiated to PDX1-positive endoderm cells by providing to a cell culture comprising PDX1-negative, SOX17-positive definitive endoderm cells a differentiation factor that promotes differentiation of the cells to PDX1-positive foregut endoderm cells (foregut differentiation factor). In some embodiments of the present invention, the foregut differentiation factor is retinoid, such as retinoic acid (RA). In some embodiments, the retinoid is used in conjunction with a fibroblast growth factor, such as FGF-4 or FGF-10. In other embodiments, the retinoid is used in conjunction with a member of the TGFβ superfamily of growth factors and/or a conditioned medium.

By "conditioned medium" is meant, a medium that is altered as compared to a base medium. For example, the conditioning of a medium may cause molecules, such as nutrients and/or growth factors, to be added to or depleted from the original levels found in the base medium. In some embodiments, a medium is conditioned by allowing cells of certain types to be grown or maintained in the medium under certain conditions for a certain period of time. For example, a medium can be conditioned by allowing hESCs to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media. In some embodiments of the present invention, a medium is conditioned by allowing differentiated pluripotent cells to be grown or maintained in a medium comprising about 1% to about 20% serum concentration. In other embodiments, a medium is conditioned by allowing differentiated pluripotent cells to be grown or maintained in a medium comprising about 1 ng/ml to about 1000 ng/ml activin A. In still other embodiments, a medium is conditioned allowing differentiated pluripotent cells to be grown or maintained in a medium comprising about 1 ng/ml to about 1000 ng/ml BMP4. In a preferred embodiment, a conditioned medium is prepared by allowing differentiated hESCs to be grown or maintained for 24 hours in a medium, such as RPMI, comprising about 25 ng/ml activin A and about 2 µM RA.

In some embodiments of the present invention, the cells used to condition the medium, which is used to enhance the differentiation of PDX1-negative definitive endoderm to PDX1-positive foregut endoderm, are cells that are differentiated from pluripotent cells, such as hESCs, over about a 5 day time period in a medium such as RPMI comprising about 0% to about 20% serum and/or one or more growth/differentiation factors of the TGFβ superfamily. Differentiation factors, such as activin A and BMP4 are supplied at concentrations ranging from about 1 ng/ml to about 1000 ng/ml. In certain embodiments of the present invention, the cells used to condition the medium are differentiated from hESCs over about a 5 day period in low serum RPMI. According to some embodiments, low serum RPMI refers to a low serum containing medium, wherein the serum concentration is gradually increased over a defined time period. For example, in one embodiment, low serum RPMI comprises a concentration of about 0.2% fetal bovine serum (FBS) on the first day of cell growth, about 0.5% FBS on the second day of cell growth and about 2% FBS on the third through fifth day of cell growth. In another embodiment, low serum RPMI comprises a concentration of about 0% on day one, about 0.2% on day two and about 2% on days 3-6. In certain preferred embodiments, low serum RPMI is supplemented with one or more differentiation factors, such as activin A and BMP4. In addition to its use in preparing cells used to condition media, low serum RPMI can be used as a medium for the differentiation of PDX1-positive foregut endoderm cells from PDX1-negative definitive endoderm cells.

It will be appreciated by those of ordinary skill in the art that conditioned media can be prepared from media other than RPMI provided that such media do not interfere with the growth or maintenance of PDX1-positive foregut endoderm cells. It will also be appreciated that the cells used to condition the medium can be of various types. In embodiments where freshly differentiated cells are used to condition a medium, such cells can be differentiated in a medium other than RPMI provided that the medium does not inhibit the growth or maintenance of such cells. Furthermore, a skilled artisan will appreciate that neither the duration of conditioning nor the duration of preparation of cells used for conditioning is required to be 24 hours or 5 days, respectively, as other time periods will be sufficient to achieve the effects reported herein.

In general, the use of a retinoid in combination with a fibroblast growth factor, a member of the TGFβ superfamily of growth factors, a conditioned medium or a combination of any of these foregut differentiation factors causes greater differentiation of PDX1-negative definitive endoderm to PDX1-positive foregut endoderm than the use of a retinoid alone. In a preferred embodiment, RA and FGF-10 are both provided to the PDX1-negative definitive endoderm cell culture. In another preferred embodiment, PDX1-negative definitive endoderm cells are differentiated in a culture comprising a conditioned medium, activin A, activin B and RA.

With respect to some of the embodiments of differentiation processes described herein, the above-mentioned foregut differentiation factors are provided to the cells so that these factors are present in the cell culture or cell population at concentrations sufficient to promote differentiation of at least a portion of the PDX1-negative definitive endoderm cell culture or cell population to PDX1-positive foregut endoderm cells. When used in connection with cell cultures and/or cell populations, the term "portion" means any non-zero amount of the cell culture or cell population, which ranges from a single cell to the entirety of the cell culture or cells population.

In some embodiments of the present invention, a retinoid is provided to the cells of a cell culture such that it is present at a concentration of at least about 0.01 µM, at least about 0.02 µM, at least about 0.04 µM, at least about 0.08 µM, at least about 0.1 µM, at least about 0.2 µM, at least about 0.3

µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM. As used herein, "retinoid" refers to retinol, retinal or retinoic acid as well as derivatives of any of these compounds. In a preferred embodiment, the retinoid is retinoic acid.

In other embodiments of the present invention, one or more differentiation factors of the fibroblast growth factor family are present in the cell culture. For example, in some embodiments, FGF-4 can be present in the cell culture at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml. In further embodiments of the present invention, FGF-10 is present in the cell culture at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml. In some embodiments, either FGF-4 or FGF-10, but not both, is provided to the cell culture along with RA. In a preferred embodiment, RA is present in the cell culture at 1 µM and FGF-10 is present at a concentration of 50 ng/ml.

In some embodiments of the present invention, growth factors of the TGFβ superfamily and/or a conditioned medium are present in the cell culture. These differentiation factors can be used in combination with RA and/or other mid-foregut differentiation factors including, but not limited to, FGF-4 and FGF-10. For example, in some embodiments, activin A and/or activin B can be present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml. In further embodiments of the present invention, a conditioned medium is present in the cell culture at a concentration of at least about 1%, at least about 5%, at least about 10%, at least about 20%, at least about 30%, at least about 40%, at least about 50%, at least about 60%, at least about 70%, at least about 80%, at least about 90%, or at least about 100% of the total medium. In some embodiments, activin A, activin B and a conditioned medium are provided to the cell culture along with RA. In a preferred embodiment, PDX1-negative definitive endoderm cells are differentiated to PDX1-positive foregut endoderm cells in cultures comprising about 1 µM RA, about 25 ng/ml activin A and low serum RPMI medium that has been conditioned for about 24 hours by differentiated hESCs, wherein the differentiated hESCs have been differentiated for about 5 days in low serum RPMI comprising about 100 ng/ml activin A. In another preferred embodiment, activin B and/or FGF-10 are also present in the culture at 25 ng/ml and 50 ng/ml, respectively.

In certain embodiments of the present invention, the above-mentioned foregut differentiation factors are removed from the cell culture subsequent to their addition. For example, the foregut differentiation factors can be removed within about one day, about two days, about three days, about four days, about five days, about six days, about seven days, about eight days, about nine days or about ten days after their addition.

Cultures of PDX1-positive foregut endoderm cells can be grown in a medium containing reduced serum. Serum concentrations can range from about 0.05% (v/v) to about 20% (v/v). In some embodiments, PDX1-positive foregut endoderm cells are grown with serum replacement. For example, in certain embodiments, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, PDX1-positive foregut endoderm cells are grown without serum. In other embodiments, PDX1-positive foregut endoderm cells are grown with serum replacement.

In still other embodiments, PDX1-positive foregut endoderm cells are grown in the presence of B27. In such embodiments, B27 can be provided to the culture medium in concentrations ranging from about 0.1% (v/v) to about 20% (v/v) or in concentrations greater than about 20% (v/v). In certain embodiments, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50× B27 stock solution to 90 ml of growth medium would produce a growth medium supplemented with 5× B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

Monitoring the Differentiation of PDX1-Negative Definitive Endoderm to PDX1-Positive Endoderm As with the differentiation of definitive endoderm cells from pluripotent cells, the progression of differentiation from PDX1-negative, SOX17-positive definitive endoderm to PDX1-positive foregut endoderm can be monitored by determining the expression of markers characteristic of these cell types. Such monitoring permits one to determine the amount of time that is sufficient for the production of a desired amount of PDX1-positive foregut endoderm under various conditions, for example, one or more differentiation factor concentrations and environmental conditions. In preferred embodiments, the amount of time that is sufficient for the production of a desired amount of PDX1-positive foregut endoderm is determined by detecting the expression of PDX1. In some embodiments of the present invention, the expression of certain markers is determined by detecting the presence or absence of the marker. Alternatively, the expression of certain markers can be determined by measuring the level at which the marker is present in the cells of the cell culture or cell population. In such embodiments, the measurement of marker expression can be qualitative or quantitative. As described above, a preferred method of quantitating the expression markers that are produced by marker genes is through the use of Q-PCR. In particular embodiments, Q-PCR is used to monitor the progression of cells of the PDX1-negative, SOX17-positive definitive endoderm culture to PDX1-positive foregut endoderm cells by quantitating expression of marker genes characteristic of PDX1-positive foregut endoderm and the lack of expression of marker genes characteristic of other cell types. Other methods which are known in the art can also be used to quantitate marker gene expression. For example, the expression of a marker gene product can be detected by using antibodies specific for the marker gene product of interest. In some embodiments of the present invention, the expression of marker genes characteristic of PDX1-positive foregut endoderm as well as the lack of significant expression of marker genes characteristic of PDX1-negative definitive endoderm, hESCs and other cell types is determined.

As described further in the Examples below, PDX1 is a marker gene that is associated with PDX1-positive foregut endoderm. As such, in some embodiments of the present invention, the expression of PDX1 is determined. In other embodiments, the expression of other markers, which are expressed in PDX1-positive foregut endoderm, including, but not limited to, SOX17, HOXA13 and/or HOXC6 is also determined. Since PDX1 can also be expressed by certain other cell types (that is, visceral endoderm and certain neural ectoderm), some embodiments of the present invention relate to demonstrating the absence or substantial absence of marker gene expression that is associated with visceral endoderm and/or neural ectoderm. For example, in some embodiments, the expression of markers, which are expressed in visceral endoderm and/or neural cells, including, but not limited to, SOX7, AFP, SOX1, ZIC1 and/or NFM is determined.

In some embodiments, PDX1-positive foregut endoderm cell cultures produced by the methods described herein are substantially free of cells expressing the SOX7, AFP, SOX1, ZIC1 or NFM marker genes. In certain embodiments, the PDX1-positive foregut endoderm cell cultures produced by the processes described herein are substantially free of visceral endoderm, parietal endoderm and/or neural cells.

Enrichment, Isolation and/or Purification of PDX1-Positive Foregut Endoderm

With respect to additional aspects of the present invention, PDX1-positive foregut endoderm cells can be enriched, isolated and/or purified. In some embodiments of the present invention, cell populations enriched for PDX1-positive foregut endoderm cells are produced by isolating such cells from cell cultures.

In some embodiments of the present invention, PDX1-positive foregut endoderm cells are fluorescently labeled then isolated from non-labeled cells by using a fluorescence activated cell sorter (FACS). In such embodiments, a nucleic acid encoding green fluorescent protein (GFP) or another nucleic acid encoding an expressible fluorescent marker gene is used to label PDX1-positive cells. For example, in some embodiments, at least one copy of a nucleic acid encoding GFP or a biologically active fragment thereof is introduced into a pluripotent cell, preferably a human embryonic stem cell, downstream of the PDX1 promoter such that the expression of the GFP gene product or biologically active fragment thereof is under control of the PDX1 promoter. In some embodiments, the entire coding region of the nucleic acid, which encodes PDX1, is replaced by a nucleic acid encoding GFP or a biologically active fragment thereof. In other embodiments, the nucleic acid encoding GFP or a biologically active fragment thereof is fused in frame with at least a portion of the nucleic acid encoding PDX1, thereby generating a fusion protein. In such embodiments, the fusion protein retains a fluorescent activity similar to GFP.

Fluorescently marked cells, such as the above-described pluripotent cells, are differentiated to definitive endoderm and then to PDX1-positive foregut endoderm as described previously above. Because PDX1-positive foregut endoderm cells express the fluorescent marker gene, whereas PDX1-negative cells do not, these two cell types can be separated. In some embodiments, cell suspensions comprising a mixture of fluorescently-labeled PDX1-positive cells and unlabeled PDX1-negative cells are sorted using a FACS. PDX1-positive cells are collected separately from PDX1-negative cells, thereby resulting in the isolation of such cell types. If desired, the isolated cell compositions can be further purified by additional rounds of sorting using the same or different markers that are specific for PDX1-positive foregut endoderm.

In addition to the procedures just described, PDX1-positive foregut endoderm cells may also be isolated by other techniques for cell isolation. Additionally, PDX1-positive foregut endoderm cells may also be enriched or isolated by methods of serial subculture in growth conditions which promote the selective survival or selective expansion of said PDX1-positive foregut endoderm cells.

It will be appreciated that the above-described enrichment, isolation and purification procedures can be used with such cultures at any stage of differentiation.

Using the methods described herein, enriched, isolated and/or purified populations of PDX1-positive foregut endoderm cells and/or tissues can be produced in vitro from PDX1-negative, SOX17-positive definitive endoderm cell cultures or cell populations which have undergone at least some differentiation. In some embodiments, the cells undergo random differentiation. In a preferred embodiment, however, the cells are directed to differentiate primarily into PDX1-positive foregut endoderm cells. Some preferred enrichment, isolation and/or purification methods relate to the in vitro production of PDX1-positive foregut endoderm cells from human embryonic stem cells.

Using the methods described herein, cell populations or cell cultures can be enriched in PDX1-positive foregut endoderm cell content by at least about 2- to about 1000-fold as compared to untreated cell populations or cell cultures. In some embodiments, PDX1-positive foregut endoderm cells can be enriched by at least about 5- to about 500-fold as compared to untreated cell populations or cell cultures. In other embodiments, PDX1-positive foregut endoderm cells can be enriched from at least about 10- to about 200-fold as compared to untreated cell populations or cell cultures. In still other embodiments, PDX1-positive foregut endoderm cells can be enriched from at least about 20- to about 100-fold as compared to untreated cell populations or cell cultures. In yet other embodiments, PDX1-positive foregut endoderm cells can be enriched from at least about 40- to about 80-fold as compared to untreated cell populations or cell cultures. In certain embodiments, PDX1-positive foregut endoderm cells can be enriched from at least about 2- to about 20-fold as compared to untreated cell populations or cell cultures.

Compositions Comprising PDX1-Positive Foregut Endoderm

Some embodiments of the present invention relate to cell compositions, such as cell cultures or cell populations, comprising PDX1-positive endoderm cells, wherein the PDX1-positive endoderm cells are multipotent cells that can differentiate into cells, tissues or organs derived from the anterior portion of the gut tube (PDX1-positive foregut endoderm). In accordance with certain embodiments, the PDX1-positive foregut endoderm are mammalian cells, and in a preferred embodiment, the definitive endoderm cells are human cells.

Other embodiments of the present invention relate to compositions, such as cell cultures or cell populations, comprising cells of one or more cell types selected from the group consisting of hESCs, PDX1-negative definitive endoderm cells, PDX1-positive foregut endoderm cells and mesoderm cells. In some embodiments, hESCs comprise less than about 5%, less than about 4%, less than about 3%, less than about 2% or less than about 1% of the total cells in the culture. In other embodiments, PDX1-negative definitive endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In yet other embodiments, mesoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Additional embodiments of the present invention relate to compositions, such as cell cultures or cell populations, produced by the processes described herein comprise PDX1-positive foregut endoderm as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 85%, at least about 80%, at least about 75%, at least about 70%, at least about 65%, at least about 60%, at least about 55%, at least about 54%, at least about 53%, at least about 52% or at least about 51% PDX1-positive foregut endoderm cells. In preferred embodiments the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% PDX1-positive foregut endoderm cells. In preferred embodiments, the cells of the cell cultures or cell populations comprise human cells. In some embodiments, the percentage of PDX1-positive foregut endoderm cells in the cell cultures or populations is calculated without regard to the feeder cells remaining in the culture.

Still other embodiments of the present invention relate to compositions, such as cell cultures or cell populations, comprising mixtures of PDX1-positive foregut endoderm cells and PDX1-negative definitive endoderm cells. For example, cell cultures or cell populations comprising at least about 5 PDX1-positive foregut endoderm cells for about every 95 PDX1-negative definitive endoderm cells can be produced. In other embodiments, cell cultures or cell populations comprising at least about 95 PDX1-positive foregut endoderm cells for about every 5 PDX1-negative definitive endoderm cells can be produced. Additionally, cell cultures or cell populations comprising other ratios of PDX1-positive foregut endoderm cells to PDX1-negative definitive endoderm cells are contemplated. For example, compositions comprising at least about 1 PDX1-positive foregut endoderm cell for about every 1,000,000 PDX1-negative definitive endoderm cells, at least about 1 PDX1-positive foregut endoderm cell for about every 100,000 PDX1-negative definitive endoderm cells, at least about 1 PDX1-positive foregut endoderm cell for about every 10,000 PDX1-negative definitive endoderm cells, at least about 1 PDX1-positive foregut endoderm cell for about every 1000 PDX1-negative definitive endoderm cells, at least about 1 PDX1-positive foregut endoderm cell for about every 500 PDX1-negative definitive endoderm cells, at least about 1 PDX1-positive foregut endoderm cell for about every 100 PDX1-negative definitive endoderm cells, at least about 1 PDX1-positive foregut endoderm cell for about every 10 PDX1-negative definitive endoderm cells, at least about 1 PDX1-positive foregut endoderm cell for about every 5 PDX1-negative definitive endoderm cells, at least about 1 PDX1-positive foregut endoderm cell for about every 4 PDX1-negative definitive endoderm cells, at least about 1 PDX1-positive foregut endoderm cell for about every 2 PDX1-negative definitive endoderm cells, at least about 1 PDX-1 positive foregut endoderm cell for about every 1 PDX1-negative definitive endoderm cell, at least about 2 PDX1-positive foregut endoderm cells for about every 1 PDX1-negative definitive endoderm cell, at least about 4 PDX1-positive foregut endoderm cells for about every 1 PDX1-negative definitive endoderm cell, at least about 5 PDX1-positive foregut endoderm cells for about every 1 PDX1- negative definitive endoderm cell, at least about 10 PDX1-positive foregut endoderm cells for about every 1 PDX1-negative definitive endoderm cell, at least about 20 PDX1-positive foregut endoderm cells for about every 1 PDX1-negative definitive endoderm cell, at least about 50 PDX1-positive foregut endoderm cells for about every 1 PDX1-negative definitive endoderm cell, at least about 100 PDX1-positive foregut endoderm cells for about every 1 PDX1-negative definitive endoderm cell, at least about 1000 PDX1-positive foregut endoderm cells for about every 1 PDX1-negative definitive endoderm cell, at least about 10,000 PDX1-positive foregut endoderm cells for about every 1 PDX1-negative definitive endoderm cell, at least about 100,000 PDX1-positive foregut endoderm cells for about every 1 PDX1-negative definitive endoderm cell and at least about 1,000,000 PDX1-positive foregut endoderm cells for about every 1 PDX1-negative definitive endoderm cell are contemplated.

In some embodiments of the present invention, the PDX1-negative definitive endoderm cells from which PDX1-positive foregut endoderm cells are produced are derived from human pluripotent cells, such as human pluripotent stem cells. In certain embodiments, the human pluripotent cells are derived from a morula, the inner cell mass of an embryo or the gonadal ridges of an embryo. In certain other embodiments, the human pluripotent cells are derived from the gondal or germ tissues of a multicellular structure that has developed past the embryonic stage.

Further embodiments of the present invention relate to compositions, such as cell cultures or cell populations, comprising human cells, including human PDX1-positive foregut endoderm, wherein the expression of the PDX1 marker is greater than the expression of the AFP, SOX7, SOX1, ZIC1 and/or NFM marker in at least about 2% of the human cells. In other embodiments, the expression of the PDX1 marker is greater than the expression of the AFP, SOX7, SOX1, ZIC1 and/or NFM marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of PDX1 is greater than the expression of the AFP, SOX7, SOX1, ZIC1 and/or NFM marker, is calculated without regard to feeder cells.

It will be appreciated that some embodiments of the present invention relate to compositions, such as cell cultures or cell populations, comprising human PDX1-positive foregut endoderm cells, wherein the expression of one or more markers selected from the group consisting of SOX17, HOXA13 and HOXC6 is greater than the expression of the AFP, SOX7, SOX1, ZIC1 and/or NFM marker in from at least about 2% to greater than at least about 98% of the human cells. In some embodiments, the expression of one or more markers selected from the group consisting of SOX17, HOXA13 and HOXC6 is greater than the expression of the AFP, SOX7, SOX1, ZIC1 and/or NFM marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of one or more markers selected from the group consisting of SOX17, HOXA13 and HOXC6 is greater than the expression of the AFP, SOX7, SOX1, ZIC1 and/or NFM marker, is calculated without regard to feeder cells.

Additional embodiments of the present invention relate to compositions, such as cell cultures or cell populations, comprising mammalian endoderm cells, such as human endoderm cells, wherein the expression of the PDX1 marker is greater than the expression of the AFP, SOX7, SOX1, ZIC1 and/or NFM marker in at least about 2% of the endodermal cells. In other embodiments, the expression of the PDX1 marker is greater than the expression of the AFP, SOX7, SOX1, ZIC1 and/or NFM marker in at least about 5% of the endodermal cells, in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or in at least about 98% of the endodermal cells.

Still other embodiments of the present invention relate to compositions, such as cell cultures or cell populations, comprising mammalian endodermal cells, such as human endodermal cells, wherein the expression of one or more markers selected from the group consisting of SOX17, HOXA13 and HOXC6 is greater than the expression of the AFP, SOX7, SOX1, ZIC1 and/or NFM marker in at least about 2% of the endodermal cells. In other embodiments, the expression of one or more markers selected from the group consisting of SOX17, HOXA13 and HOXC6 is greater than the expression of the AFP, SOX7, SOX1, ZIC1 and/or NFM marker in at least about 5% of the endodermal cells, in at least about 10% of the endodermal cells, in at least about 15% of the endodermal cells, in at least about 20% of the endodermal cells, in at least about 25% of the endodermal cells, in at least about 30% of the endodermal cells, in at least about 35% of the endodermal cells, in at least about 40% of the endodermal cells, in at least about 45% of the endodermal cells, in at least about 50% of the endodermal cells, in at least about 55% of the endodermal cells, in at least about 60% of the endodermal cells, in at least about 65% of the endodermal cells, in at least about 70% of the endodermal cells, in at least about 75% of the endodermal cells, in at least about 80% of the endodermal cells, in at least about 85% of the endodermal cells, in at least about 90% of the endodermal cells, in at least about 95% of the endodermal cells or at least about 98% of the endodermal cells.

Using the processes described herein, compositions comprising PDX1-positive foregut endoderm cells substantially free of other cell types can be produced. With respect to cells in cell cultures or in cell populations, the term "substantially free of" means that the specified cell type of which the cell culture or cell population is free, is present in an amount of less than about 5% of the total number of cells present in the cell culture or cell population. In some embodiments of the present invention, the PDX1-positive foregut endoderm cell populations or cell cultures produced by the methods described herein are substantially free of cells that significantly express the AFP, SOX7, SOX1, ZIC1 and/or NFM marker genes.

In one embodiment of the present invention, a description of a PDX1-positive foregut endoderm cell based on the expression of marker genes is, PDX1 high, AFP low, SOX7 low, SOX1 low, ZIC1 low and NFM low.

Increasing Expression of PDX1 in a SOX17-Positive Definitive Endoderm Cell

Some aspects of the present invention are related to methods of increasing the expression of the PDX1 gene product in cell cultures or cell populations comprising SOX17-positive definitive endoderm cells. In such embodiments, the SOX17-positive definitive endoderm cells are contacted with a differentiation factor in an amount that is sufficient to increase the expression of the PDX1 gene product. The SOX17-positive definitive endoderm cells that are contacted with the differentiation factor can be either PDX1-negative or PDX1-positive. In some embodiments, the differentiation factor can be a retinoid. In certain embodiments, SOX17-positive definitive endoderm cells are contacted with a retinoid at a concentration ranging from about 0.01 µM to about 50 µM. In a preferred embodiment, the retinoid is RA.

In other embodiments of the present invention, the expression of the PDX1 gene product in cell cultures or cell populations comprising SOX17-positive definitive endoderm cells is increased by contacting the SOX17-positive cells with a differentiation factor of the fibroblast growth factor family Such differentiation factors can either be used alone or in conjunction with RA. In some embodiments, the SOX17-positive definitive endoderm cells are contacted with a fibroblast growth factor at a concentration ranging from about 10 ng/ml to about 1000 ng/ml. In a preferred embodiment, the FGF growth factor is FGF-10.

In some embodiments of the present invention, the expression of the PDX1 gene product in cell cultures or cell populations comprising SOX17-positive definitive endoderm cells is increased by contacting the SOX17-positive cells with B27. This differentiation factor can either be used alone or in conjunction with one or both of retinoid and FGF family differentiation factors. In some embodiments, the SOX17-positive definitive endoderm cells are contacted with B27 at a concentration ranging from about 0.1% (v/v) to about 20% (v/v). In a preferred embodiment, the SOX17-positive definitive endoderm cells are contacted with RA, FGF-10 and B27.

Methods for increasing the expression of the PDX1 gene product in cell cultures or cell populations comprising SOX17-positive definitive endoderm cells can be carried out in growth medium containing reduced or no serum. In some embodiments, serum concentrations range from about 0.05% (v/v) to about 20% (v/v). In some embodiments, the SOX17-positive cells are grown with serum replacement.

Identification of Factors Capable of Promoting the Differentiation of PDX1-Negative Definitive Endoderm Cells to PDX1-Positive Foregut Endoderm Cells Additional aspects of the present invention relate to methods of identifying one or more differentiation factors capable of promoting the differentiation of PDX1-negative definitive endoderm cells to PDX1-positive foregut endoderm cells. In such methods, a cell culture or cell population comprising PDX1-negative definitive endoderm cells is obtained and the expression of PDX1 in the cell culture or cell population is determined. After determining the expression of PDX1, the cells of the cell culture or cell population are contacted with a candidate differentiation factor. In some embodiments, the expression of PDX1 is determined at the time of contacting or shortly after contacting the cells with a candidate differentiation factor. PDX1 expression is then determined at one or more times after contacting the cells with the candidate differentiation factor. If the expression of PDX1 has increased after contact with the candidate differentiation factor as compared to PDX1 expression prior to contact with the candidate differentiation factor, the candidate differentiation factor is identified as capable of promoting the differentiation of PDX1-negative definitive endoderm cells to PDX1-positive foregut endoderm cells.

In some embodiments, the above-described methods of identifying factors capable of promoting the differentiation of PDX1-negative definitive endoderm cells to PDX1-positive foregut endoderm cells also include determining the expression of the HOXA13 gene and/or the HOXC6 gene in the cell culture or cell population. In such embodiments, the expression of HOXA13 and/or HOXC6 is determined both before and after the cells are contacted with the candidate differentiation factor. If the expression of PDX1 and HOXA13 has increased after contact with the candidate differentiation factor as compared to PDX1 and HOXA13 expression prior to contact with the candidate differentiation factor, the candidate differentiation factor is identified as capable of promoting the differentiation of PDX1-negative definitive endoderm cells to PDX1-positive foregut endoderm cells. Similarly, if the expression of PDX1 and HOXC6 has increased after contact with the candidate differentiation factor as compared to PDX1 and HOXC6 expression prior to contact with the candidate differentiation factor, the candidate differentiation factor is identified as capable of promoting the differentiation of PDX1-negative definitive endoderm cells to PDX1-positive foregut endoderm cells. In a preferred embodiment, a candidate differentiation factor is identified as being capable of promoting the differentiation of PDX1-negative definitive endoderm cells to PDX1-positive foregut endoderm cells by determining the expression of PDX1, HOXA13 and HOXC6 both before and after contacting the cells of the cell culture or cell population with the candidate differentiation factor. In preferred embodiments, the expression of PDX1, HOXA13 and/or HOXC6 is determined Q-PCR.

It will be appreciated that in some embodiments, the expression of one or more of PDX1, HOXA13 and HOXC6 can be determined at the time of contacting or shortly after contacting the cells of the cell cultures or cell populations with a candidate differentiation factor rather than prior to contacting the cells with a candidate differentiation factor. In such embodiments, the expression of one or more of PDX1, HOXA13 and HOXC6 at the time of contacting or shortly after contacting the cells with a candidate differentiation factor is compared to the expression of one or more of PDX1, HOXA13 and HOXC6 at one or more times after contacting the cells with a candidate differentiation factor.

In some embodiments of the above-described methods, the one or more times at which PDX1 expression is determined after contacting the cells with the candidate differentiation factor can range from about 1 hour to about 10 days. For example, PDX1 expression can be determined about 1 hour after contacting the cells with the candidate differentiation factor, about 2 hours after contacting the cells with the candidate differentiation factor, about 4 hours after contacting the cells with the candidate differentiation factor, about 6 hours after contacting the cells with the candidate differentiation factor, about 8 hours after contacting the cells with the candidate differentiation factor, about 10 hours after contacting the cells with the candidate differentiation factor, about 12 hours after contacting the cells with the candidate differentiation factor, about 16 hours after contacting the cells with the candidate differentiation factor, about 24 hours after contacting the cells with the candidate differentiation factor, about 2 days after contacting the cells with the candidate differentiation factor, about 3 days after contacting the cells with the candidate differentiation factor, about 4 days after contacting the cells with the candidate differentiation factor, about 5 days after contacting the cells with the candidate differentiation factor, about 6 days after contacting the cells with the candidate differentiation factor, about 7 days after contacting the cells with the candidate differentiation factor, about 8 days after contacting the cells with the candidate differentiation factor, about 9 days after contacting the cells with the candidate differentiation factor, about 10 days after contacting the cells with the candidate differentiation factor or more than 10 days after contacting the cells with the candidate differentiation factor.

Candidate differentiation factors for use in the methods described herein can be selected from compounds, such as polypeptides and small molecules. For example, candidate polypeptides can include, but are not limited to, growth factors, cytokines, chemokines, extracellular matrix proteins, and synthetic peptides. In a preferred embodiment, the growth factor is from the FGF family, for example FGF-10. Candidate small molecules include, but are not limited to, compounds generated from combinatorial chemical synthesis and natural products, such as steroids, isoprenoids, terpenoids, phenylpropanoids, alkaloids and flavinoids. It will be appreciated by those of ordinary skill in the art that thousands of classes of natural and synthetic small molecules are available and that the small molecules contemplated for use in the methods described herein are not limited to the classes exemplified above. Typically, small molecules will have a molecular weight less than 10,000 amu. In a preferred embodiment, the small molecule is a retinoid, for example RA.

Identification of Factors Capable of Promoting the Differentiation of PDX1-Positive Foregut Endoderm Cells Other aspects of the present invention relate to methods of identifying one or more differentiation factors capable of promoting the differentiation of PDX1-positive foregut endoderm cells. In such methods, a cell culture or cell population comprising PDX1-positive foregut endoderm cells is obtained and the expression of a marker in the cell culture or cell population is determined. After determining the expression of the marker, the cells of the cell culture or cell population are contacted with a candidate differentiation factor. In some embodiments, the expression of the marker is determined at the time of contacting or shortly after contacting the cells with a candidate differentiation factor. The expression of the same marker is then determined at one or more times after contacting the cells with the candidate differentiation factor. If the expression of the marker has increased or decreased after contact with the candidate differentiation factor as compared to the marker expression prior to contact with the candidate differentiation factor, the candidate differentiation factor is identified as capable of promoting the differentiation of PDX1-positive foregut endoderm cells. In preferred embodiments, expression of the marker is determined by Q-PCR.

In some embodiments of the above-described methods, the one or more times at which the marker expression is determined after contacting the cells with the candidate differentiation factor can range from about 1 hour to about 10 days. For example, marker expression can be determined about 1 hour after contacting the cells with the candidate differentiation factor, about 2 hours after contacting the cells with the candidate differentiation factor, about 4 hours after contacting the cells with the candidate differentiation factor, about 6 hours after contacting the cells with the candidate differentiation factor, about 8 hours after contacting the cells with the candidate differentiation factor, about 10 hours after contacting the cells with the candidate differentiation factor, about 12 hours after contacting the cells with the candidate differentiation factor, about 16 hours after contacting the cells with the candidate differentiation factor, about 24 hours after contacting the cells with the candidate differentiation factor, about 2 days after contacting the cells with the candidate differentiation factor, about 3 days after contacting the cells with the candidate differentiation factor, about 4 days after contacting the cells with the candidate differentiation factor, about 5 days after contacting the cells with the candidate differentiation factor, about 6 days after contacting the cells with the candidate differentiation factor, about 7 days after contacting the cells with the candidate differentiation factor, about 8 days after contacting the cells with the candidate differentiation factor, about 9 days after contacting the cells with the candidate differentiation factor, about 10 days after contacting the cells with the candidate differentiation factor or more than 10 days after contacting the cells with the candidate differentiation factor.

As described previously, candidate differentiation factors for use in the methods described herein can be selected from compounds such as polypeptides and small molecules.

Although each of the methods disclosed herein have been described with respect to PDX1-positive foregut endoderm cells, it will be appreciated that in certain embodiments, these methods can be used to produce compositions comprising the PDX1-positive foregut/midgut endoderm cells that are described herein and/or the PDX1-positive endoderm cells of the posterior portion of the foregut that are described herein. Furthermore, any of the PDX1-positive endoderm cell types disclosed in this specification can be utilized in the screening methods described herein.

Having generally described this invention, a further understanding can be obtained by reference to certain specific examples which are provided herein for purposes of illustration only, and are not intended to be limiting.

EXAMPLES

Many of the examples below describe the use of pluripotent human cells. Methods of producing pluripotent human cells are well known in the art and have been described numerous scientific publications, including U.S. Pat. Nos. 5,453,357, 5,670,372, 5,690,926, 6,090,622, 6,200,806 and 6,251,671 as well as U.S. Patent Application Publication No. 2004/0229350, the disclosures of which are incorporated herein by reference in their entireties.

Example 1

Human ES Cells

For our studies of endoderm development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, ITS supplement). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-111 tubulin was observed in clusters of elongated cells, characteristic of early neurons. Previously, we treated EBs in suspension with retinoic acid, to induce differentiation of pluripotent stem cells to visceral endoderm (VE), an extraembryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Production of SOX17 Antibody

A primary obstacle to the identification of definitive endoderm in hESC cultures is the lack of appropriate tools. We therefore undertook the production of an antibody raised against human SOX17 protein.

The marker SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. It has now been discovered that SOX17 is an appropriate marker for the definitive endoderm lineage when used in conjunction with markers to exclude extra-embryonic lineages.

As described in detail herein, the SOX17 antibody was utilized to specifically examine effects of various treatments and differentiation procedures aimed at the production of SOX17 positive definitive endoderm cells. Other antibodies reactive to AFP, SPARC and Thrombomodulin were also employed to rule out the production of visceral and parietal endoderm (extra-embryonic endoderm).

Figure 2:
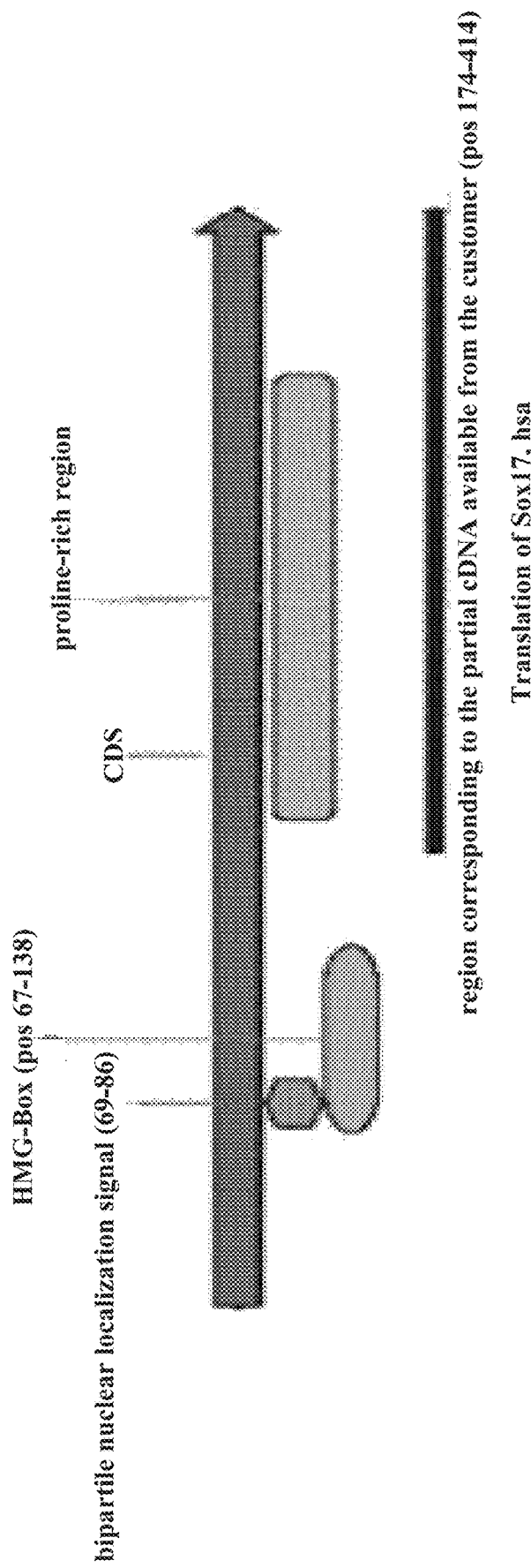
FIG. 2 is a diagram of the human SOX17 cDNA which displays the positions of conserved motifs and highlights the region used for the immunization procedure by GENOVAC.

In order to produce an antibody against SOX17, a portion of the human SOX17 cDNA (SEQ ID NO: 1) corresponding to amino acids 172-414 (SEQ ID NO: 2) in the carboxyterminal end of the SOX17 protein (FIG. 2) was used for genetic immunization in rats at the antibody production company, GENOVAC (Freiberg, Germany), according to procedures developed there. Procedures for genetic immunization can be found in U.S. Pat. Nos. 5,830,876, 5,817, 637, 6,165,993 and 6,261,281 as well as International Patent Application Publication Nos. WO00/29442 and WO99/13915, the disclosures of which are incorporated herein by reference in their entireties.

Other suitable methods for genetic immunization are also described in the non-patent literature. For example, Barry et al. describe the production of monoclonal antibodies by genetic immunization in Biotechniques 16: 616-620, 1994, the disclosure of which is incorporated herein by reference in its entirety. Specific examples of genetic immunization methods to produce antibodies against specific proteins can be found, for example, in Costaglia et al., (1998) Genetic immunization against the human thyrotropin receptor causes thyroiditis and allows production of monoclonal antibodies recognizing the native receptor, *J. Immunol.* 160: 1458-

1465; Kilpatrick et al (1998) Gene gun delivered DNA-based immunizations mediate rapid production of murine monoclonal antibodies to the Flt-3 receptor, Hybridoma 17: 569-576; Schmolke et al., (1998) Identification of hepatitis G virus particles in human serum by E2-specific monoclonal antibodies generated by DNA immunization, *J. Virol.* 72: 4541-4545; Krasemann et al., (1999) Generation of monoclonal antibodies against proteins with an unconventional nucleic acid-based immunization strategy, *J. Biotechnol.* 73: 119-129; and Ulivieri et al., (1996) Generation of a monoclonal antibody to a defined portion of the *Heliobacter pylori* vacuolating cytotoxin by DNA immunization, *J. Biotechnol.* 51: 191-194, the disclosures of which are incorporated herein by reference in their entireties.

Figure 3:
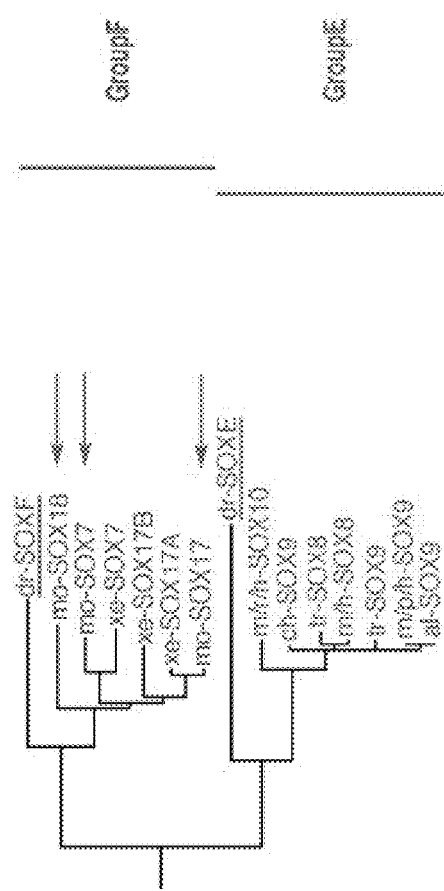
FIG. 3 is a relational dendrogram illustrating that SOX17 is most closely related to SOX7 and somewhat less to SOX18. The SOX17 proteins are more closely related among species homologs than to other members of the SOX group F subfamily within the same species.

SOX7 and SOX18 are the closest Sox family relatives to SOX17 as depicted in the relational dendrogram shown in FIG. 3. We employed the human SOX7 polypeptide as a negative control to demonstrate that the SOX17 antibody produced by genetic immunization is specific for SOX17 and does not react with its closest family member. In particular, SOX7 and other proteins were expressed in human fibroblasts, and then, analyzed for cross reactivity with the SOX17 antibody by Western blot and ICC. For example, the following methods were utilized for the production of the SOX17, SOX7 and EGFP expression vectors, their transfection into human fibroblasts and analysis by Western blot. Expression vectors employed for the production of SOX17, SOX7, and EGFP were pCMV6 (OriGene Technologies, Inc., Rockville, Md.), pCMV-SPORT6 (Invitrogen, Carlsbad, Calif.) and pEGFP-N1 (Clonetech, Palo Alto, Calif.), respectively. For protein production, telomerase immortalized MDX human fibroblasts were transiently transfected with supercoiled DNA in the presence of Lipofectamine 2000 (Invitrogen, Carlsbad, Calif.). Total cellular lysates were collected 36 hours post-transfection in 50 mM TRIS-HCl (pH 8), 150 mM NaCl, 0.1% SDS, 0.5% deoxycholate, containing a cocktail of protease inhibitors (Roche Diagnostics Corporation, Indianapolis, Ind.). Western blot analysis of 100 µg of cellular proteins, separated by SDS-PAGE on NuPAGE (4-12% gradient polyacrylamide, Invitrogen, Carlsbad, Calif.), and transferred by electro-blotting onto PDVF membranes (Hercules, Calif.), were probed with a 1/1000 dilution of the rat SOX17 anti-serum in 10 mM TRIS-HCl (pH 8), 150 mM NaCl, 10% BSA, 0.05% Tween-20 (Sigma, St. Louis, Mo.), followed by Alkaline Phosphatase conjugated anti-rat IgG (Jackson ImmunoResearch Laboratories, West Grove, Pa.), and revealed through Vector Black Alkaline Phosphatase staining (Vector Laboratories, Burlingame, Calif.). The proteins size standard used was wide range color markers (Sigma, St. Louis, Mo.).

Figure 4:
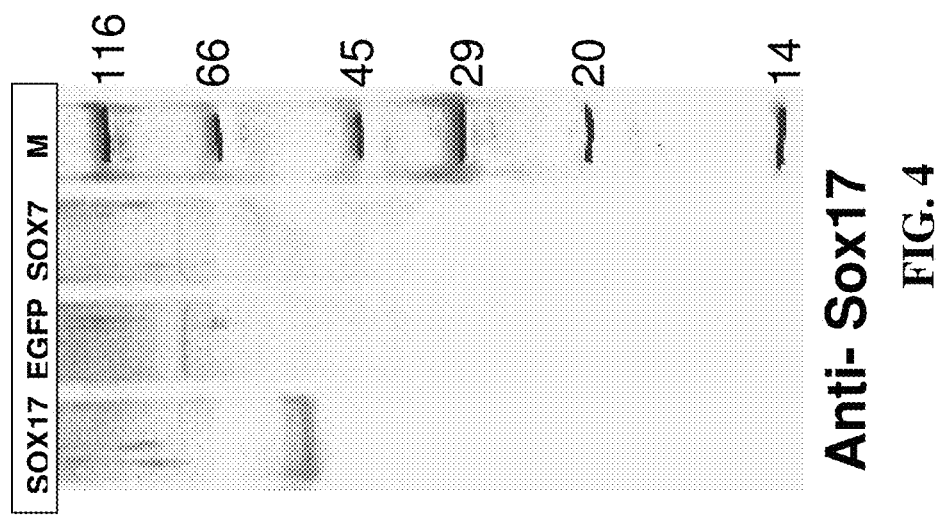
FIG. 4 is a Western blot probed with the rat anti-SOX17 antibody. This blot demonstrates the specificity of this antibody for human SOX17 protein over-expressed in fibroblasts (lane 1) and a lack of immunoreactivity with EGFP (lane 2) or the most closely related SOX family member, SOX7 (lane 3).

In FIG. 4, protein extracts made from human fibroblast cells that were transiently transfected with SOX17, SOX7 or EGFP cDNA's were probed on Western blots with the SOX17 antibody. Only the protein extract from hSOX17 transfected cells produced a band of ~51 Kda which closely matched the predicted 46 Kda molecular weight of the human SOX17 protein. There was no reactivity of the SOX17 antibody to extracts made from either human SOX7 or EGFP transfected cells. Furthermore, the SOX17 antibody clearly labeled the nuclei of human fibroblast cells transfected with the hSOX17 expression construct but did not label cells transfected with EGFP alone. As such, the SOX17 antibody exhibits specificity by ICC.

Example 4

Validation of SOX17 Antibody as a Marker of Definitive Endoderm

Figure 5A:
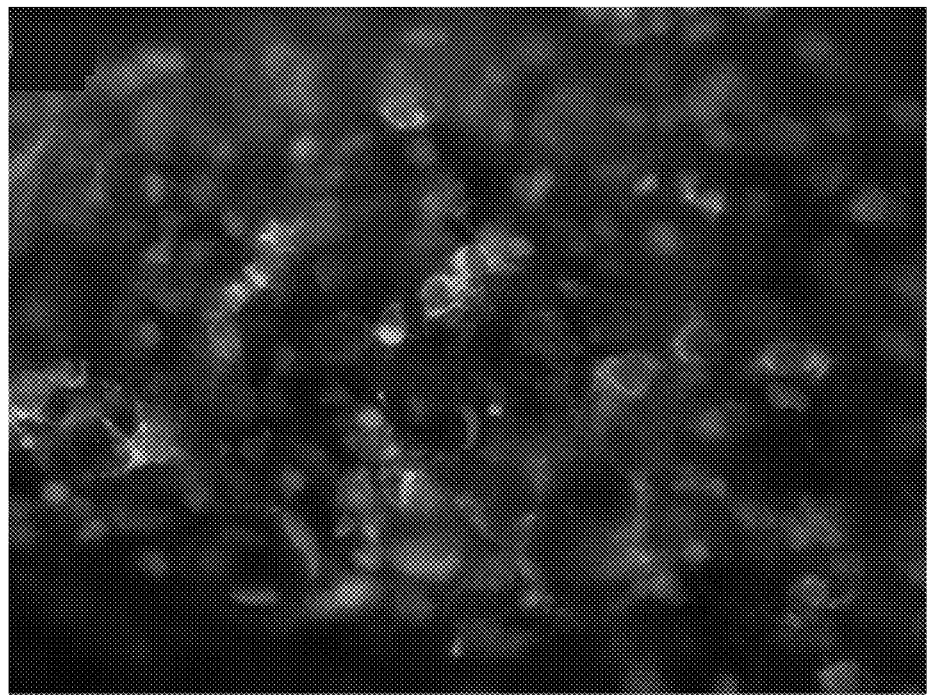
FIGS. 5A-5B are micrographs showing a cluster of SOX17$^+$ cells that display a significant number of AFP co-labeled cells (A). This is in striking contrast to other SOX17$^+$ clusters (B) where little or no AFP cells are observed.
Figure 5B:
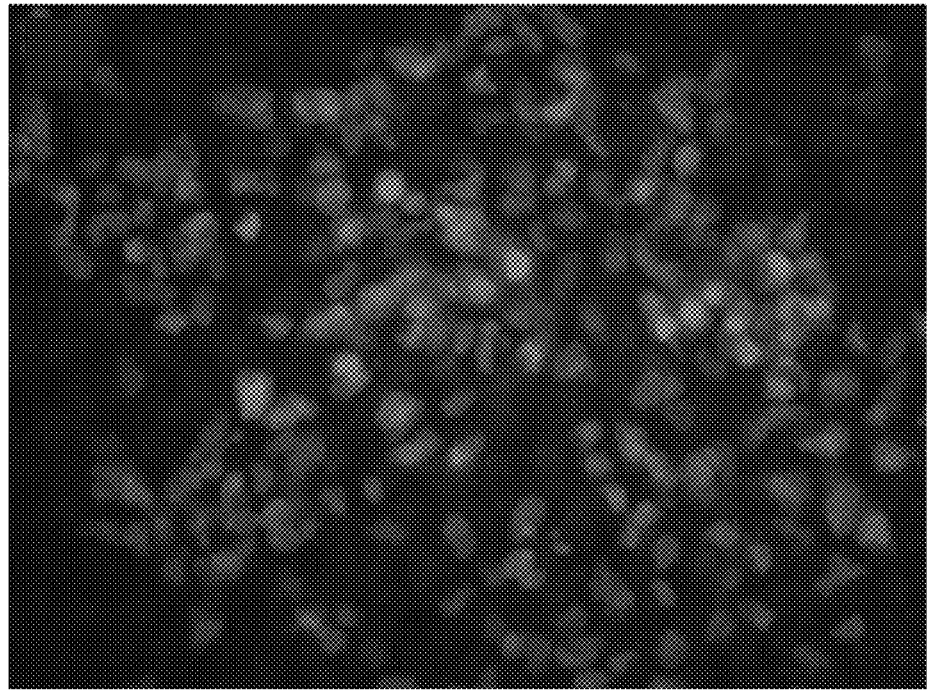

Partially differentiated hESCs were co-labeled with SOX17 and AFP antibodies to demonstrate that the SOX17 antibody is specific for human SOX17 protein and furthermore marks definitive endoderm. It has been demonstrated that SOX17, SOX7 (which is a closely related member of the SOX gene family subgroup F (FIG. 3)) and AFP are each expressed in visceral endoderm. However, AFP and SOX7 are not expressed in definitive endoderm cells at levels detectable by ICC, and thus, they can be employed as negative markers for bonifide definitive endoderm cells. It was shown that SOX17 antibody labels populations of cells that exist as discrete groupings of cells or are intermingled with AFP positive cells. In particular, FIG. 5A shows that small numbers of SOX17 cells were co-labeled with AFP; however, regions were also found where there were little or no AFP cells in the field of SOX17$^+$ cells (FIG. 5B). Similarly, since parietal endoderm has been reported to express SOX17, antibody co-labeling with SOX17 together with the parietal markers SPARC and/or Thrombomodulin (TM) can be used to identify the SOX17$^+$ cells that are parietal endoderm. As shown in FIGS. 6A-6C, Thrombomodulin and SOX17 co-labeled parietal endoderm cells were produced by random differentiation of hES cells.

In view of the above cell labeling experiments, the identity of a definitive endoderm cell can be established by the marker profile SOX17$^{hi}$/AFP$^{lo}$/[TM$^{lo}$ or SPARC$^{lo}$]. In other words, the expression of the SOX17 marker is greater than the expression of the AFP marker, which is characteristic of visceral endoderm, and the TM or SPARC markers, which are characteristic of parietal endoderm. Accordingly, those cells positive for SOX17 but negative for AFP and negative for TM or SPARC are definitive endoderm.

Figure 7A:
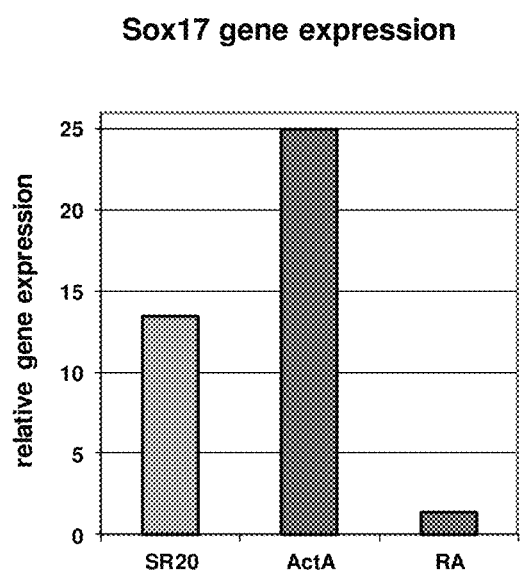
FIGS. 7A-7B are bar charts showing SOX17 gene expression by quantitative PCR (Q-PCR) and anti-SOX17 positive cells by SOX17-specific antibody. Panel A shows that activin A increases SOX17 gene expression while retinoic acid (RA) strongly suppresses SOX17 expression relative to the undifferentiated control media (SR20). Panel B shows the identical pattern as well as a similar magnitude of these changes is reflected in SOX17$^+$ cell number, indicating that Q-PCR measurement of SOX17 gene expression is very reflective of changes at the single cell level.
Figure 7B:
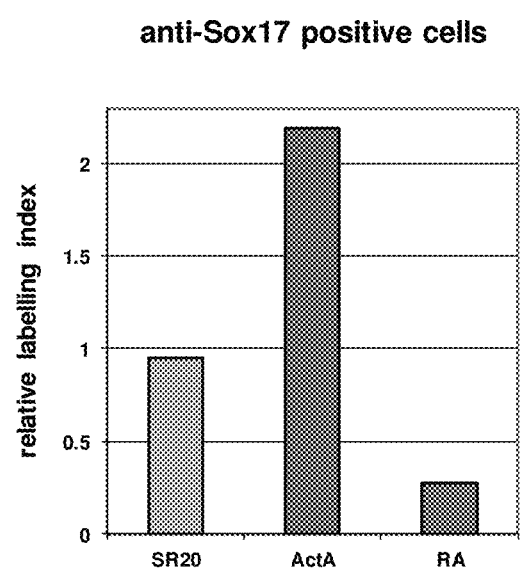
Figure 8B:
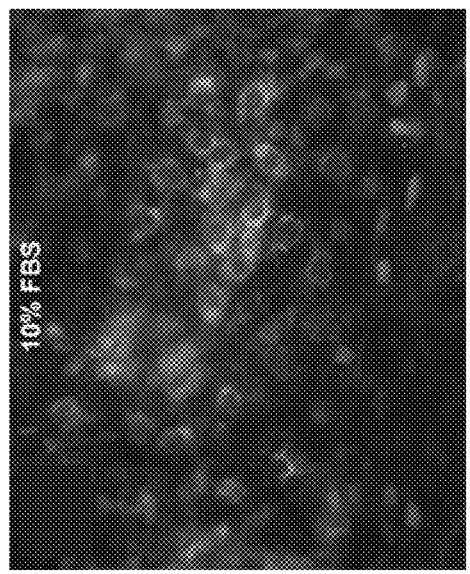
FIGS. 8B-8C are images of two micrographs showing that the suppression of AFP expression by activin A is also evident at the single cell level as indicated by the very rare and small clusters of AFP$^+$ cells observed in activin A treatment conditions (bottom) relative to 10% FBS alone (top).
Figure 8C:
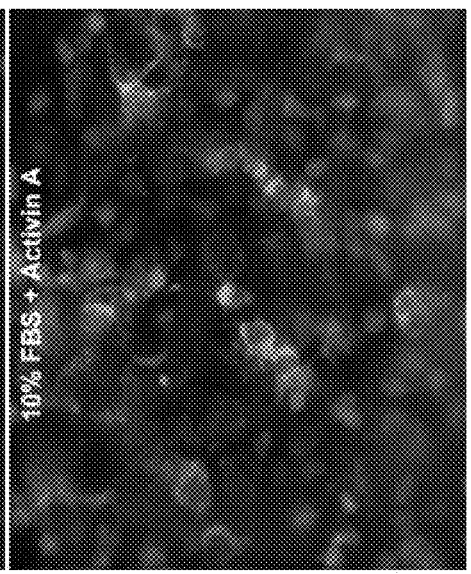
Figure 8A:
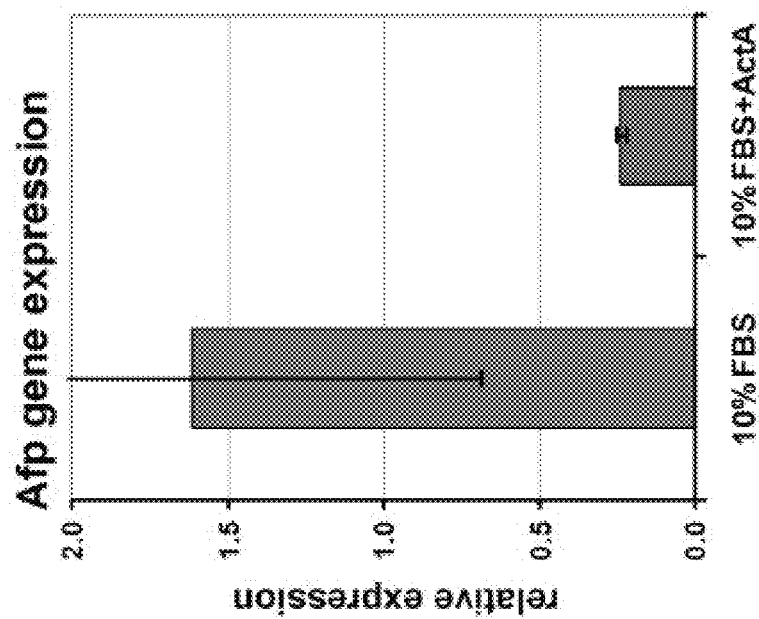
FIG. 8A is a bar chart which shows that a culture of differentiating hESCs in the presence of activin A maintains a low level of AFP gene expression while cells allowed to randomly differentiate in 10% fetal bovine serum (FBS) exhibit a strong upregulation of AFP. The difference in expression levels is approximately 7-fold.
Figure 9B:
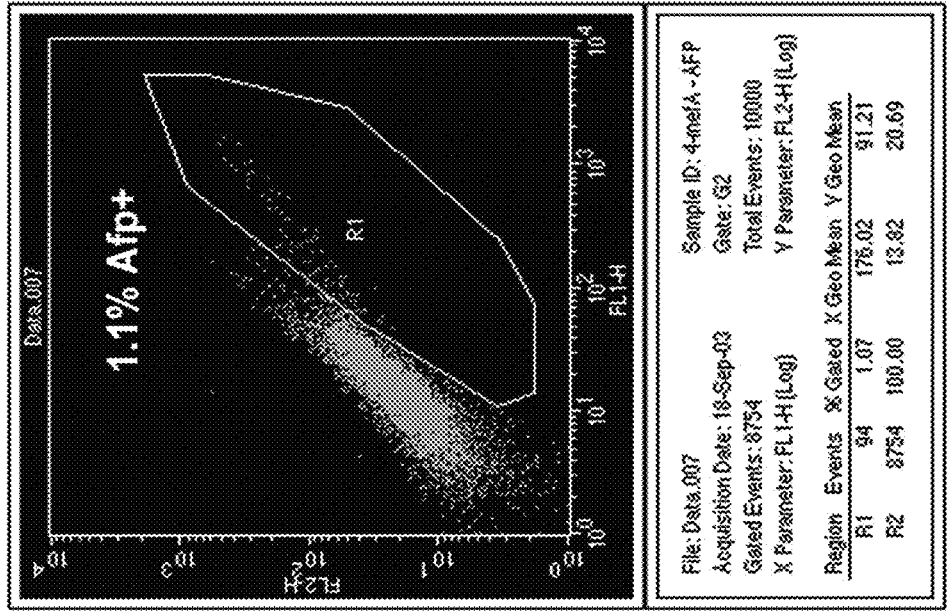
FIGS. 9A-9B are comparative images showing the quantitation of the AFP cell number using flow cytometry. This figure demonstrates that the magnitude of change in AFP gene expression (FIG. 8A) in the presence (right panel) and absence (left panel) of activin A exactly corresponds to the number of AFP cells, further supporting the utility of Q-PCR analyses to indicate changes occurring at the individual cell level.
Figure 9A:
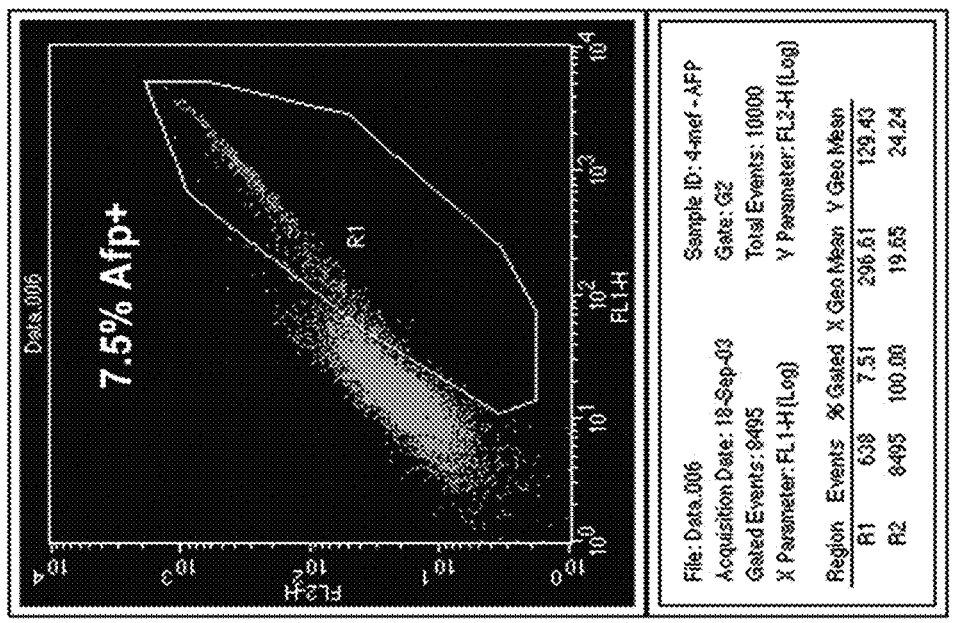
Figure 11:
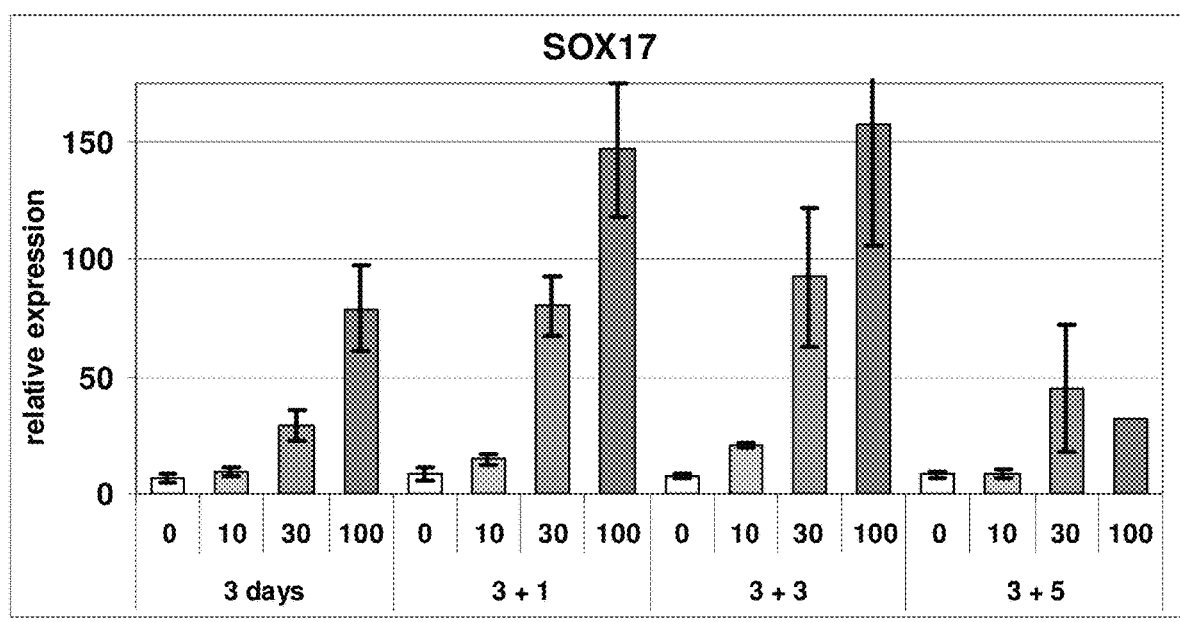
FIG. 11 is a bar chart which demonstrates that activin A (0, 10, 30 or 100 ng/ml) dose-dependently increases SOX17 gene expression in differentiating hESCs. Increased expression is already robust after 3 days of treatment on adherent cultures and continues through subsequent 1, 3 and 5 days of suspension culture as well.
Figure 12A:
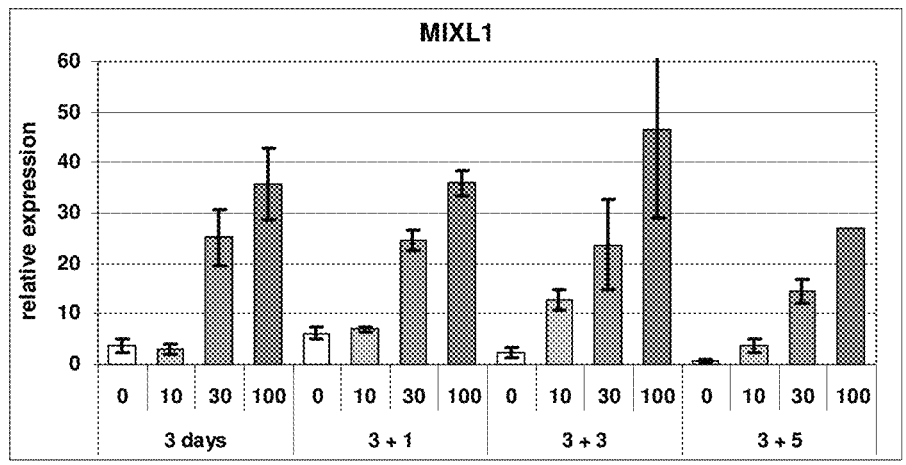
FIGS. 12A-12C are bar charts which demonstrate the effect of activin A on the expression of MIXL1 (panel A), GATA4 (panel B) and HNF3b (panel C). Activin A dose-dependent increases are also observed for three other markers of definitive endoderm; MIXL1, GATA4 and HNF3b. The magnitudes of increased expression in response to activin dose are strikingly similar to those observed for SOX17, strongly indicating that activin A is specifying a population of cells that co-express all four genes (SOX17$^+$, MIXL1$^+$, GATA4$^+$ and HNF3b$^+$).
Figure 12B:
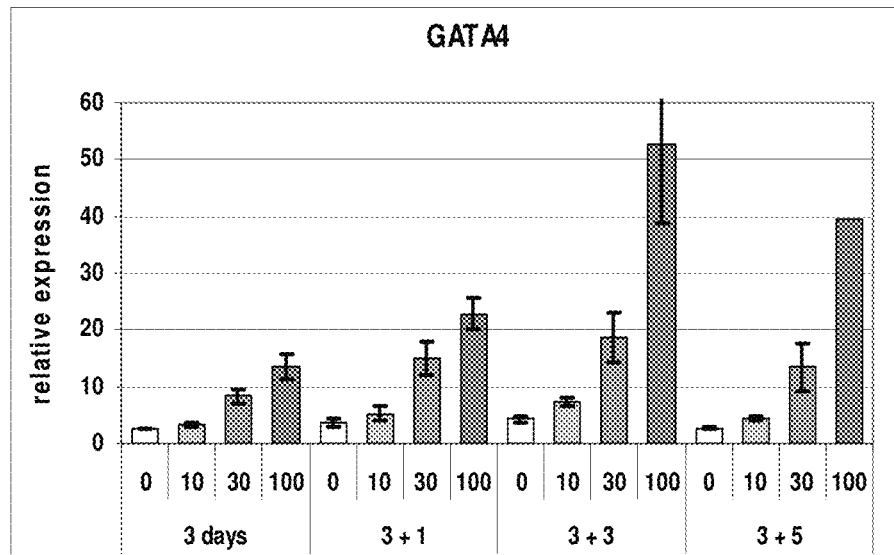
Figure 12C:
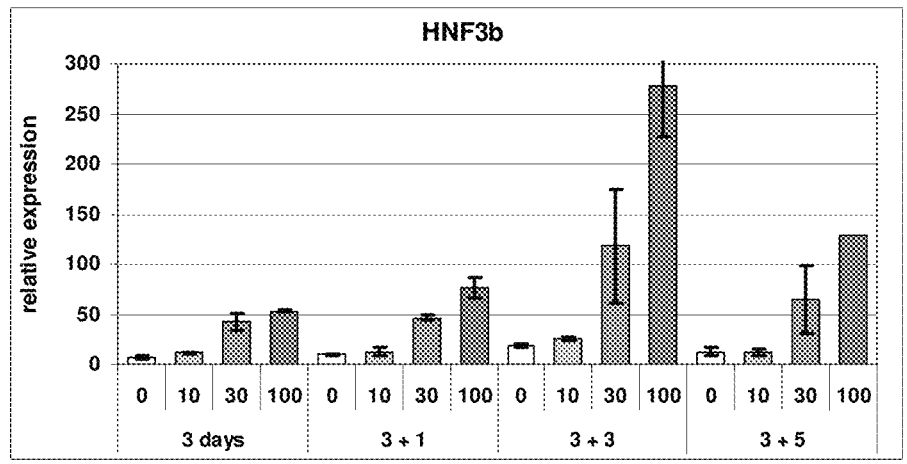
Figure 13A:
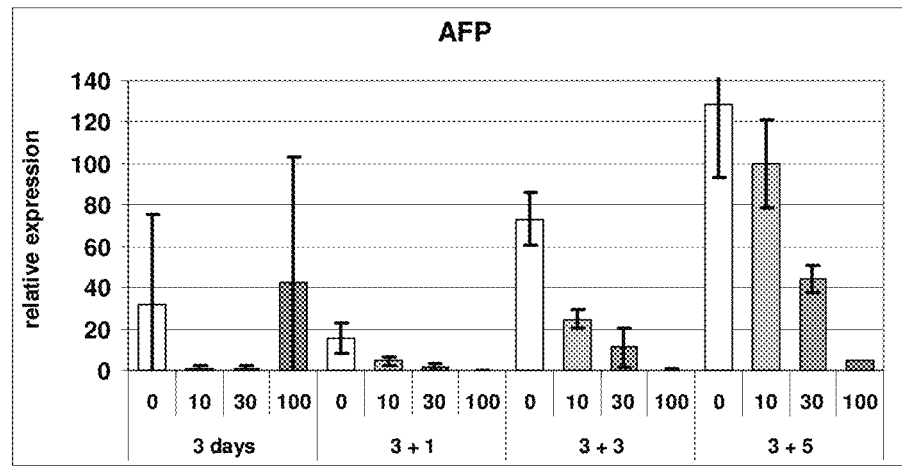
FIGS. 13A-13C are bar charts which demonstrate the effect of activin A on the expression of AFP (panel A), SOX7 (panel B) and SPARC (panel C). There is an activin A dose-dependent decrease in expression of the visceral endoderm marker AFP. Markers of primitive endoderm (SOX7) and parietal endoderm (SPARC) remain either unchanged or exhibit suppression at some time points indicating that activin A does not act to specify these extra-embryonic endoderm cell types. This further supports the fact that the increased expression of SOX17, MIXL1, GATA4, and HNF3b are due to an increase in the number of definitive endoderm cells in response to activin A.
Figure 13B:
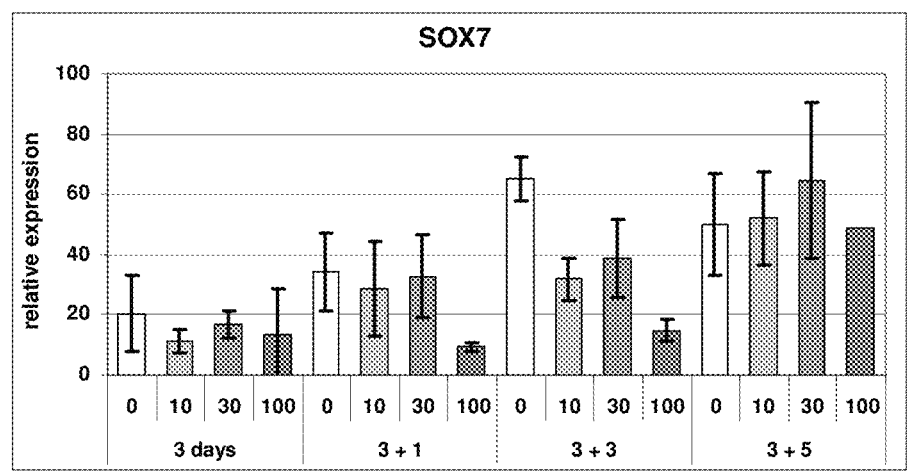
Figure 13C:
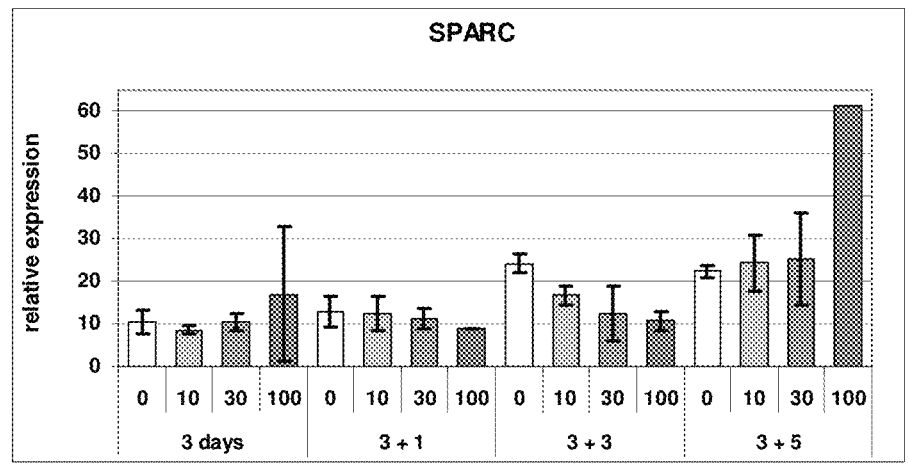
Figure 14A:
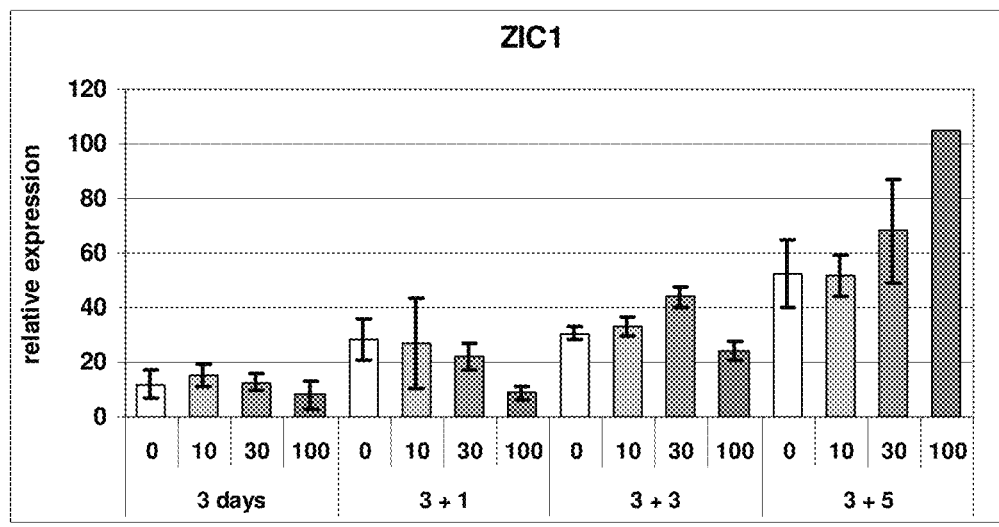
FIGS. 14A-14B are bar charts showing the effect of activin A on ZIC1 (panel A) and Brachyury expression (panel B) Consistent expression of the neural marker ZIC1 demonstrates that there is not a dose-dependent effect of activin A on neural differentiation. There is a notable suppression of mesoderm differentiation mediated by 100 ng/ml of activin A treatment as indicated by the decreased expression of brachyury. This is likely the result of the increased specification of definitive endoderm from the mesendoderm precursors. Lower levels of activin A treatment (10 and 30 ng/ml) maintain the expression of brachyury at later time points of differentiation relative to untreated control cultures.
Figure 14B:
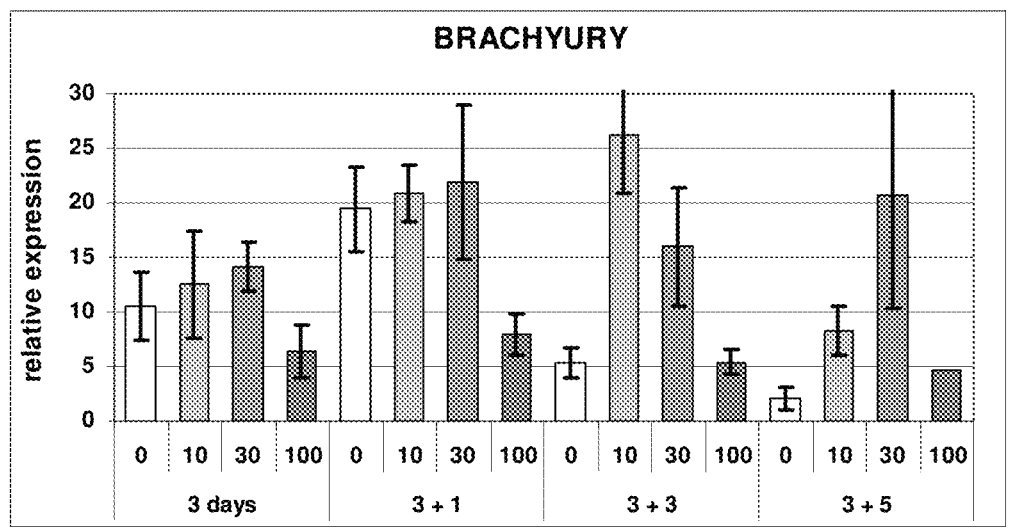

As a further evidence of the specificity of the SOX17$^{hi}$/AFP$^{lo}$/TM$^{lo}$ or SPARC$^{lo}$]. In marker profile as predictive of definitive endoderm, SOX17 and AFP gene expression was quantitatively compared to the relative number of antibody labeled cells. As shown in FIG. 7A, hESCs treated with retinoic acid (visceral endoderm inducer), or activin A (definitive endoderm inducer), resulted in a 10-fold difference in the level of SOX17 mRNA expression. This result mirrored the 10-fold difference in SOX17 antibody-labeled cell number (FIG. 7B). Furthermore, as shown in FIG. 8A, activin A treatment of hESCs suppressed AFP gene expression by 6.8-fold in comparison to no treatment. This was visually reflected by a dramatic decrease in the number of AFP labeled cells in these cultures as shown in FIGS. 8B-8C. To quantify this further, it was demonstrated that this approximately 7-fold decrease in AFP gene expression was the result of a similar 7-fold decrease in AFP antibody-labeled cell number as measured by flow cytometry (FIGS. 9A-9B). This result is extremely significant in that it indicates that quantitative changes in gene expression as seen by Q-PCR mirror changes in cell type specification as observed by antibody staining.

Incubation of hESCs in the presence of Nodal family members (Nodal, activin A and activin B-NAA) resulted in a significant increase in SOX17 antibody-labeled cells over time. By 5 days of continuous activin treatment greater than 50% of the cells were labeled with SOX17 (FIGS. 10A-10F). There were few or no cells labeled with AFP after 5 days of activin treatment.

In summary, the antibody produced against the carboxy-terminal 242 amino acids of the human SOX17 protein identified human SOX17 protein on Western blots but did not recognize SOX7, it's closest Sox family relative. The SOX17 antibody recognized a subset of cells in differentiating hESC cultures that were primarily SOX17$^+$/AFP$^{lo/-}$ (greater than 95% of labeled cells) as well as a small percentage (<5%) of cells that co-label for SOX17 and AFP (visceral endoderm). Treatment of hESC cultures with activins resulted in a marked elevation of SOX17 gene expression as well as SOX17 labeled cells and dramatically suppressed the expression of AFP mRNA and the number of cells labeled with AFP antibody.

Example 5

Q-PCR Gene Expression Assay

In the following experiments, real-time quantitative RT-PCR (Q-PCR) was the primary assay used for screening the effects of various treatments on hESC differentiation. In particular, real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression provides indications for "differentiation bias" within the population. The bias towards a particular differentiation pathway, prior to the overt differentiation of those cellular phenotypes, is unrecognizable using immunocytochemical techniques. For this reason, Q-PCR provides a method of analysis that is at least complementary and potentially much superior to immunocytochemical techniques for screening the success of differentiation treatments. Additionally, Q-PCR provides a mechanism by which to evaluate the success of a differentiation protocol in a quantitative format at semi-high throughput scales of analysis.

The approach taken here was to perform relative quantitation using SYBR Green chemistry on a Rotor Gene 3000 instrument (Corbett Research) and a two-step RT-PCR format. Such an approach allowed for the banking of cDNA samples for analysis of additional marker genes in the future, thus avoiding variability in the reverse transcription efficiency between samples.

Primers were designed to lie over exon-exon boundaries or span introns of at least 800 bp when possible, as this has been empirically determined to eliminate amplification from contaminating genomic DNA. When marker genes were employed that do not contain introns or they possess pseudogenes, DNase I treatment of RNA samples was performed.

We routinely used Q-PCR to measure the gene expression of multiple markers of target and non-target cell types in order to provide a broad profile description of gene expression in cell samples. The markers relevant for the early phases of hESC differentiation (specifically ectoderm, mesoderm, definitive endoderm and extra-embryonic endoderm) and for which validated primer sets are available are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination.

To generate PCR template, total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 µL reaction was subsequently diluted up to 100 µL total volume and 3 µL was used in each 10 µL Q-PCR reaction containing 400 nM forward and reverse primers and 5 µL 2×SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the Tm appropriate for that PCR amplicon. In addition, reactions performed without reverse transcriptase served as the negative control and do not amplify.

A first step in establishing the Q-PCR methodology was validation of appropriate housekeeping genes (HGs) in the experimental system. Since the HG was used to normalize across samples for the RNA input, RNA integrity and RT efficiency, it was of value that the HG exhibited a constant level of expression over time in all sample types in order for the normalization to be meaningful. We measured the expression levels of Cyclophilin G, hypoxanthine phosphoribosyltransferase 1 (HPRT), beta-2-microglobulin, hydroxymethylbiane synthase (HMBS), TATA-binding protein (TBP), and glucuronidase beta (GUS) in differentiating hESCs. Our results indicated that beta-2-microglobulin expression levels increased over the course of differentiation and therefore we excluded the use of this gene for normalization. The other genes exhibited consistent expression levels over time as well as across treatments. We routinely used both Cyclophilin G and GUS to calculate a normalization factor for all samples. The use of multiple HGs simultaneously reduces the variability inherent to the normalization process and increases the reliability of the relative gene expression values.

After obtaining genes for use in normalization, Q-PCR was then utilized to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
| --- | --- | --- |
| Endoderm | SOX17 | definitive, visceral and parietal endoderm |
| | MIXL1 | endoderm and mesoderm |
| | GATA4 | definitive and primitive endoderm |
| | HNF3b | definitive endoderm and primitive endoderm, mesoderm, neural plate |

TABLE 1-continued

| Germ Layer | Gene | Expression Domains |
| --- | --- | --- |
| Extra-embryonic | GSC | endoderm and mesoderm |
| | SOX7 | visceral endoderm |
| | AFP | visceral endoderm, liver |
| | SPARC | parietal endoderm |
| | TM | parietal endoderm/trophectoderm |
| Ectoderm | ZIC1 | neural tube, neural progenitors |
| Mesoderm | BRACH | nascent mesoderm |

Since many genes are expressed in more than one germ layer it is useful to quantitatively compare expression levels of many genes within the same experiment. SOX17 is expressed in definitive endoderm and to a smaller extent in visceral and parietal endoderm. SOX7 and AFP are expressed in visceral endoderm at this early developmental time point. SPARC and TM are expressed in parietal endoderm and Brachyury is expressed in early mesoderm.

Definitive endoderm cells were predicted to express high levels of SOX17 mRNA and low levels of AFP and SOX7 (visceral endoderm), SPARC (parietal endoderm) and Brachyury (mesoderm). In addition, ZIC1 was used here to further rule out induction of early ectoderm. Finally, GATA4 and HNF3b were expressed in both definitive and extra-embryonic endoderm, and thus, correlate with SOX17 expression in definitive endoderm (Table 1). A representative experiment is shown in FIGS. 11-14 which demonstrates how the marker genes described in Table 1 correlate with each other among the various samples, thus highlighting specific patterns of differentiation to definitive endoderm and extra-embryonic endoderm as well as to mesodermal and neural cell types.

In view of the above data it is clear that increasing doses of activin resulted in increasing SOX17 gene expression. Further this SOX17 expression predominantly represented definitive endoderm as opposed to extra-embryonic endoderm. This conclusion stems from the observation that SOX17 gene expression was inversely correlated with AFP, SOX7, and SPARC gene expression.

Example 6

Directed Differentiation of Human ES Cells to Definitive Endoderm

Human ES cell cultures randomly differentiate if cultured under conditions that do not actively maintain their undifferentiated state. This heterogeneous differentiation results in production of extra-embryonic endoderm cells comprised of both parietal and visceral endoderm (AFP, SPARC and SOX7 expression) as well as early ectodermal and mesodermal derivatives as marked by ZIC1 and Nestin (ectoderm) and Brachyury (mesoderm) expression. Definitive endoderm cell appearance has not been examined or specified for lack of specific antibody markers in ES cell cultures. As such, and by default, early definitive endoderm production in ES cell cultures has not been well studied. Since satisfactory antibody reagents for definitive endoderm cells have been unavailable, most of the characterization has focused on ectoderm and extra-embryonic endoderm. Overall, there are significantly greater numbers of extra-embryonic and neurectodermal cell types in comparison to SOX17$^{hi}$ definitive endoderm cells in randomly differentiated ES cell cultures.

As undifferentiated hESC colonies expand on a bed of fibroblast feeders, the cells at the edges of the colony take on alternative morphologies that are distinct from those cells residing within the interior of the colony. Many of these outer edge cells can be distinguished by their less uniform, larger cell body morphology and by the expression of higher levels of OCT4. It has been described that as ES cells begin to differentiate they alter the levels of OCT4 expression up or down relative to undifferentiated ES cells. Alteration of OCT4 levels above or below the undifferentiated threshold may signify the initial stages of differentiation away from the pluripotent state.

When undifferentiated colonies were examined by SOX17 immunocytochemistry, occasionally small 10-15-cell clusters of SOX17-positive cells were detected at random locations on the periphery and at the junctions between undifferentiated hESC colonies. As noted above, these scattered pockets of outer colony edges appeared to be some of the first cells to differentiate away from the classical ES cell morphology as the colony expanded in size and became more crowded. Younger, smaller fully undifferentiated colonies (<1 mm; 4-5 days old) showed no SOX17 positive cells within or at the edges of the colonies while older, larger colonies (1-2 mm diameter, >5 days old) had sporadic isolated patches of SOX17 positive, AFP negative cells at the periphery of some colonies or in regions interior to the edge that did not display the classical hESC morphology described previously. Given that this was the first development of an effective SOX17 antibody, definitive endoderm cells generated in such early "undifferentiated" ES cell cultures have never been previously demonstrated.

Figure 15A:
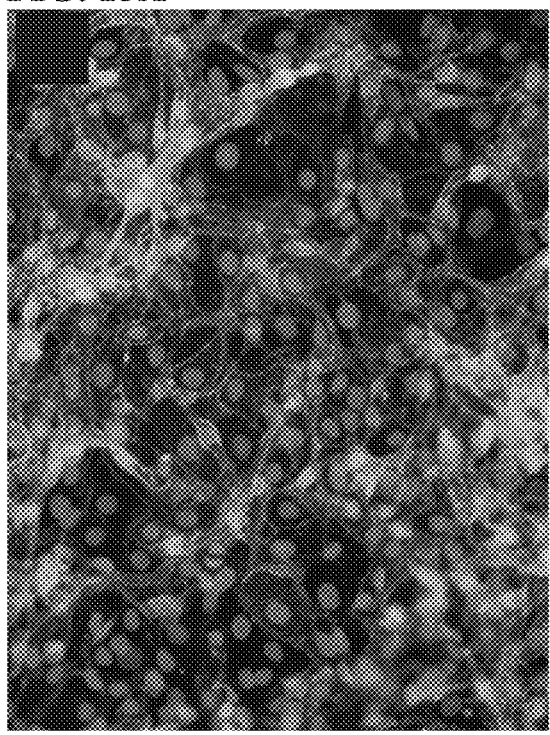
FIGS. 15A-15B are micrographs showing decreased parietal endoderm differentiation in response to treatment with activins. Regions of $TM^{hi}$ parietal endoderm are found through the culture (A) when differentiated in serum alone, while differentiation to $TM^+$ cells is scarce when activins are included (B) and overall intensity of TM immunoreactivity is lower.
Figure 15B:
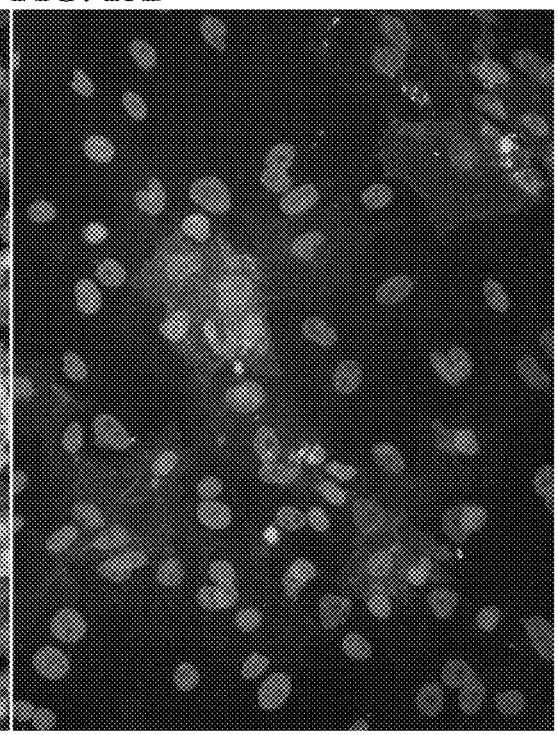
Figure 17:
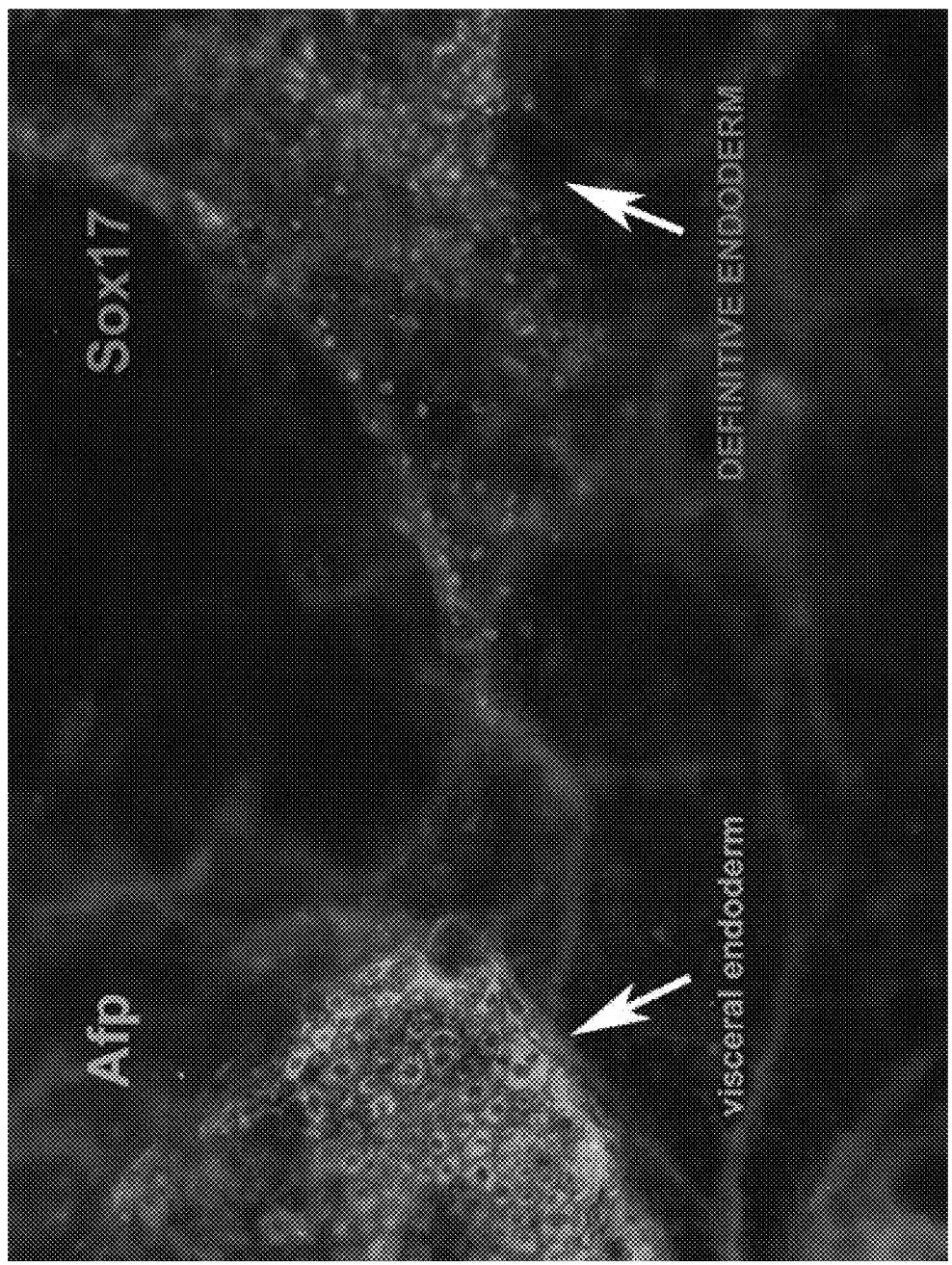
FIG. 17 is a micrograph showing the appearance of definitive endoderm and visceral endoderm in vitro from hESCs. The regions of visceral endoderm are identified by $AFP^{hi}/SOX17^{lo/-}$ while definitive endoderm displays the complete opposite profile, $SOX17^{hi}/AFP^{lo/-}$. This field was selectively chosen due to the proximity of these two regions to each other. However, there are numerous times when $SOX17^{hi}/AFP^{lo/-}$ regions are observed in absolute isolation from any regions of $AFP^{hi}$ cells, suggesting the separate origination of the definitive endoderm cells from visceral endoderm cells.
Figure 18:
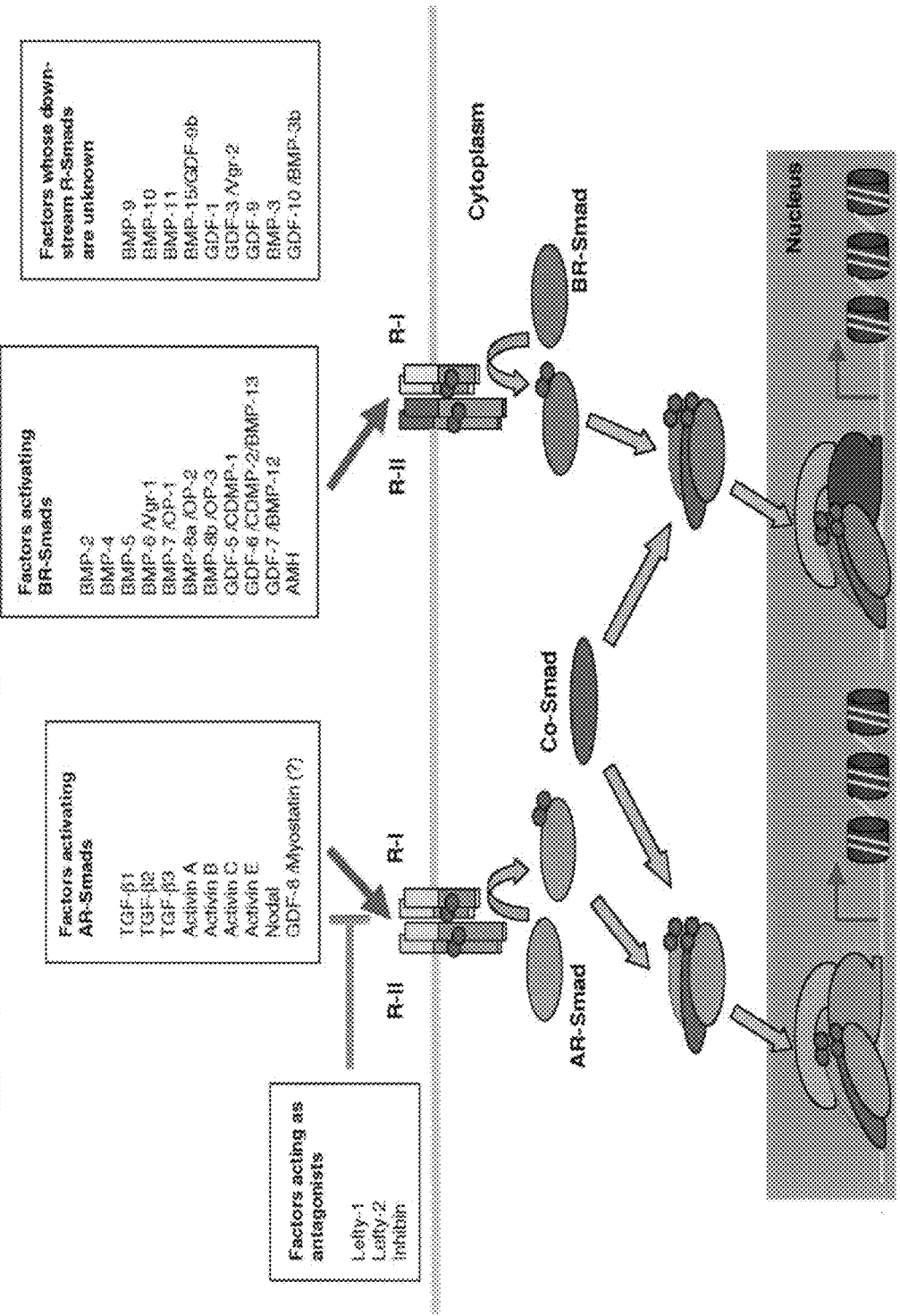
FIG. 18 is a diagram depicting the TGFβ family of ligands and receptors. Factors activating AR Smads and BR Smads are useful in the production of definitive endoderm from human embryonic stem cells (see, *J Cell Physiol.* 187:265-76).

Based on negative correlations of SOX17 and SPARC gene expression levels by Q-PCR, the vast majority of these SOX17 positive, AFP negative cells will be negative for parietal endoderm markers by antibody co-labeling. This was specifically demonstrated for TM-expressing parietal endoderm cells as shown in FIGS. 15A-15B. Exposure to Nodal factors activin A and B resulted in a dramatic decrease in the intensity of TM expression and the number of TM positive cells. By triple labeling using SOX17, AFP and TM antibodies on an activin treated culture, clusters of SOX17 positive cells that were also negative for AFP and TM were observed (FIGS. 16A-16D). These are the first cellular demonstrations of SOX17 positive definitive endoderm cells in differentiating hESC cultures (FIGS. 16A-16D and 17).

With the SOX17 antibody and Q-PCR tools described above we have explored a number of procedures capable of efficiently programming hESCs to become SOX17$^{hi}$/m/AFP$^{lo}$/SPARC/TM$^{lo}$ definitive endoderm cells. We applied a variety of differentiation protocols aimed at increasing the number and proliferative capacity of these cells as measured at the population level by Q-PCR for SOX17 gene expression and at the level of individual cells by antibody labeling of SOX17 protein.

We were the first to analyze and describe the effect of TGFβ family growth factors, such as Nodal/activin/BMP, for use in creating definitive endoderm cells from embryonic stem cells in in vitro cell cultures. In typical experiments, activin A, activin B, BMP or combinations of these growth factors were added to cultures of undifferentiated human stem cell line hESCyt-25 to begin the differentiation process.

Figure 19:
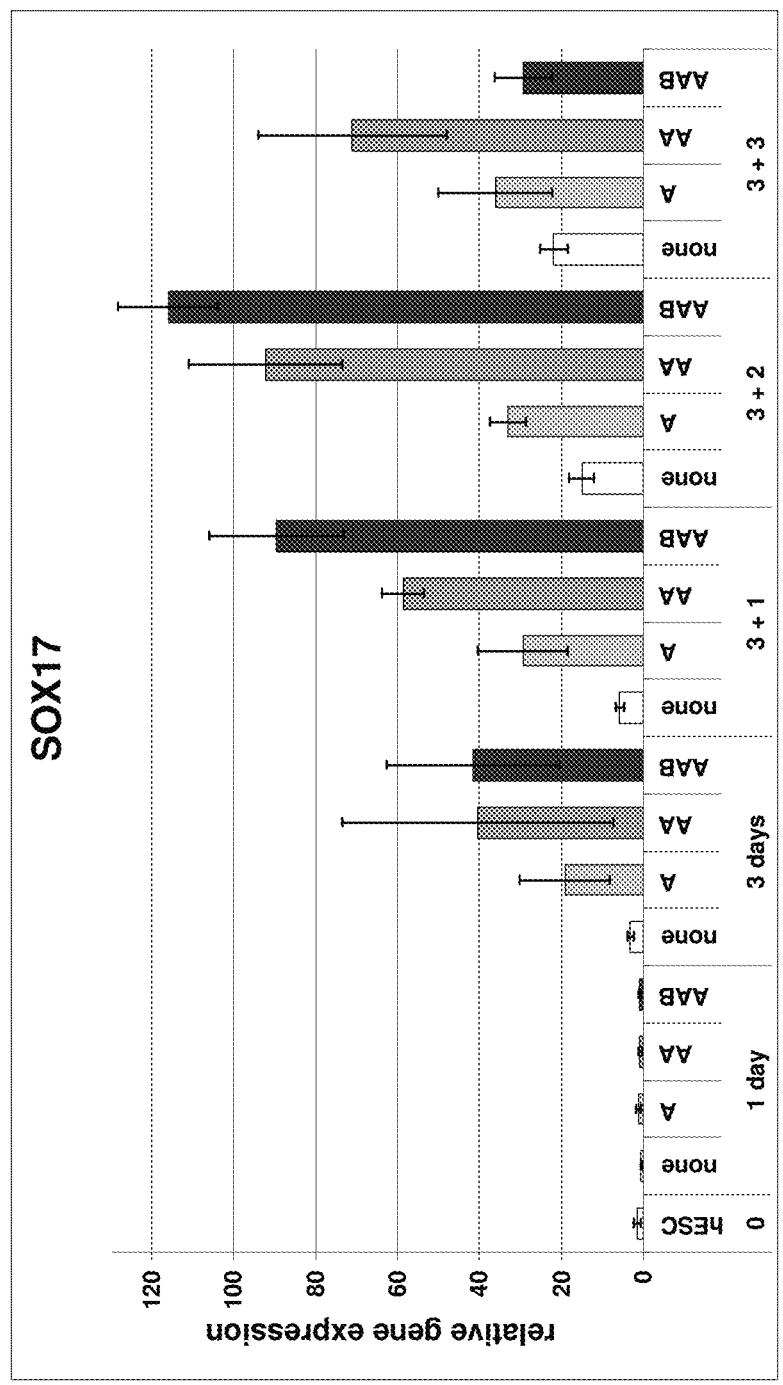
FIG. 19 is a bar chart showing the induction of SOX17 expression over time as a result of treatment with individual and combinations of TGFβ factors.

As shown in FIG. 19, addition of activin A at 100 ng/ml resulted in a 19-fold induction of SOX17 gene expression vs. undifferentiated hESCs by day 4 of differentiation. Adding activin B, a second member of the activin family, together with activin A, resulted in a 37-fold induction over undifferentiated hESCs by day 4 of combined activin treatment. Finally, adding a third member of the TGFβ family from the Nodal/Activin and BMP subgroups, BMP4, together with activin A and activin B, increased the fold induction to 57 times that of undifferentiated hESCs (FIG. 19). When SOX17 induction with activins and BMP was compared to no factor medium controls 5-, 10-, and 15-fold inductions resulted at the 4-day time point. By five days of triple treatment with activins A, B and BMP, SOX17 was induced more than 70 times higher than hESCs. These data indicate that higher doses and longer treatment times of the Nodal/activin TGFβ family members results in increased expression of SOX17.

Nodal and related molecules activin A, B and BMP facilitate the expression of SOX17 and definitive endoderm formation in vivo or in vitro. Furthermore, addition of BMP results in an improved SOX17 induction possibly through the further induction of Cripto, the Nodal co-receptor.

We have demonstrated that the combination of activins A and B together with BMP4 result in additive increases in SOX17 induction and hence definitive endoderm formation. BMP4 addition for prolonged periods (>4 days), in combination with activin A and B may induce SOX17 in parietal and visceral endoderm as well as definitive endoderm. In some embodiments of the present invention, it is therefore valuable to remove BMP4 from the treatment within 4 days of addition.

Figure 20:
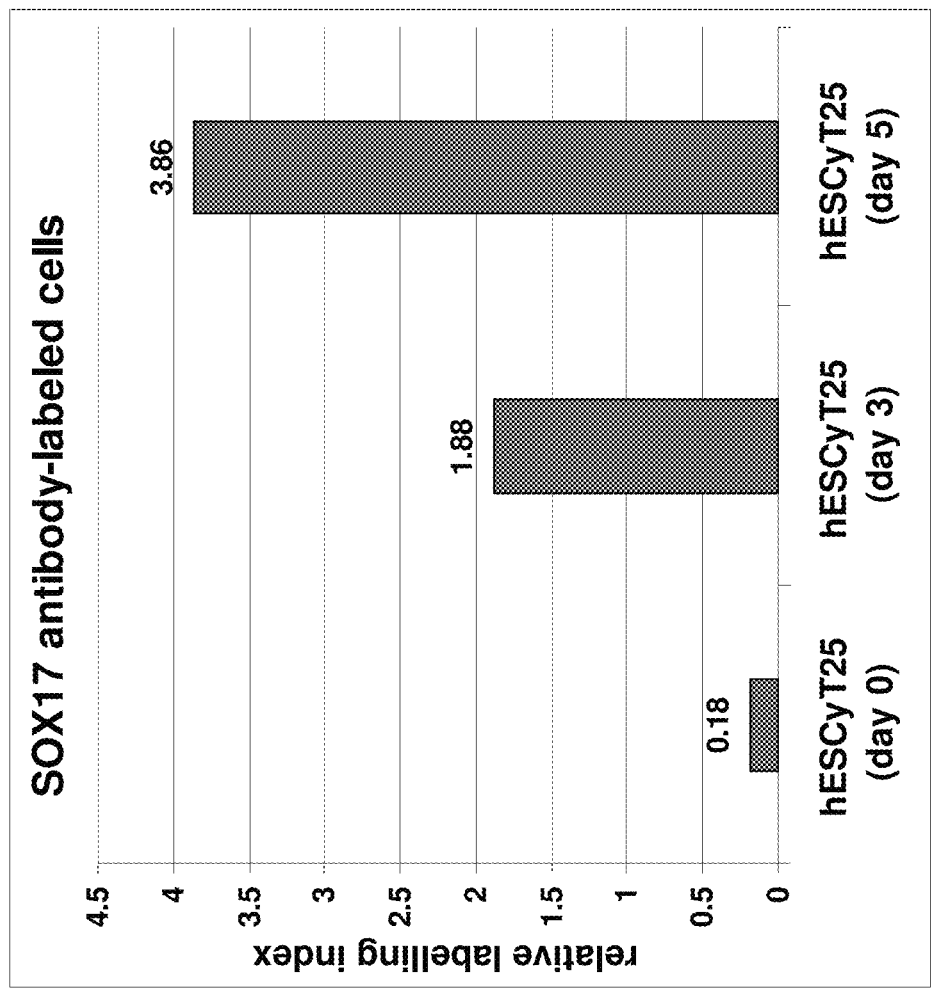
FIG. 20 is a bar chart showing the increase in $SOX17^+$ cell number with time as a result of treatment with combinations of TGFβ factors.
Figure 21:
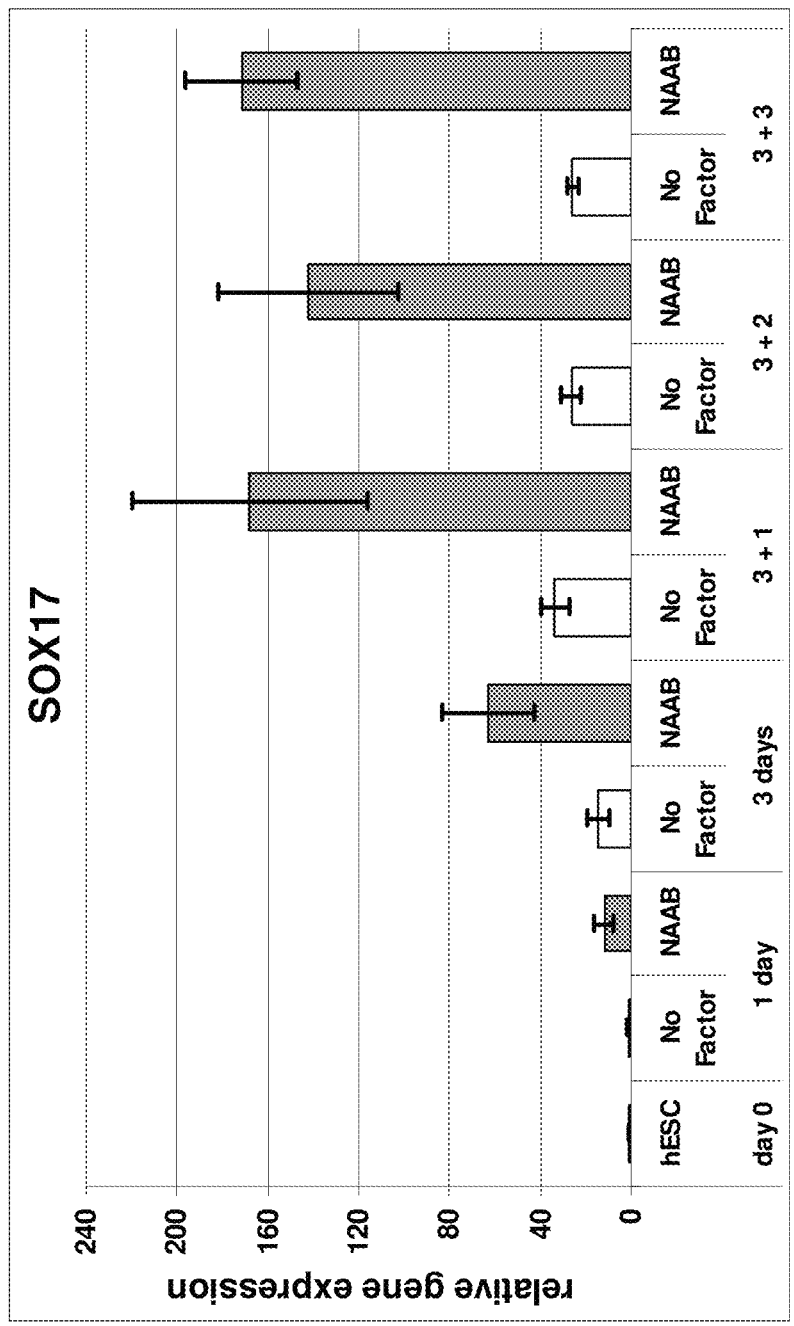
FIG. 21 is a bar chart showing induction of SOX17 expression over time as a result of treatment with combinations of TGFβ factors.
Figure 22:
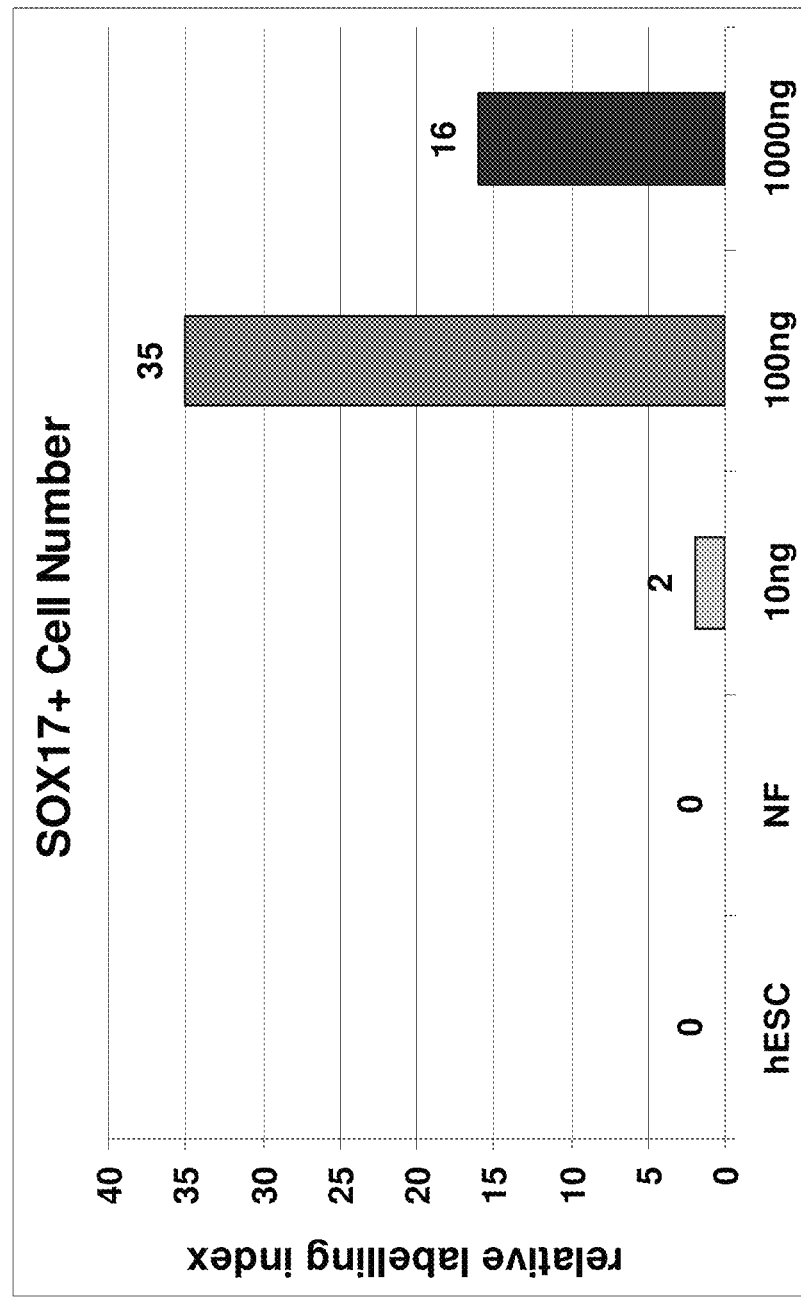
FIG. 22 is a bar chart showing that activin A induces a dose-dependent increase in $SOX17^+$ cell number.

To determine the effect of TGFβ factor treatment at the individual cell level, a time course of TGFβ factor addition was examined using SOX17 antibody labeling. As previously shown in FIGS. 10A-10F, there was a dramatic increase in the relative number of SOX17 labeled cells over time. The relative quantification (FIG. 20) shows more than a 20-fold increase in SOX17-labeled cells. This result indicates that both the numbers of cells as well SOX17 gene expression level are increasing with time of TGFβ factor exposure. As shown in FIG. 21, after four days of exposure to Nodal, activin A, activin B and BMP4, the level of SOX17 induction reached 168-fold over undifferentiated hESCs. FIG. 22 shows that the relative number of SOX17-positive cells was also dose responsive, activin A doses of 100 ng/ml or more were capable of potently inducing SOX17 gene expression and cell number.

Figure 23:
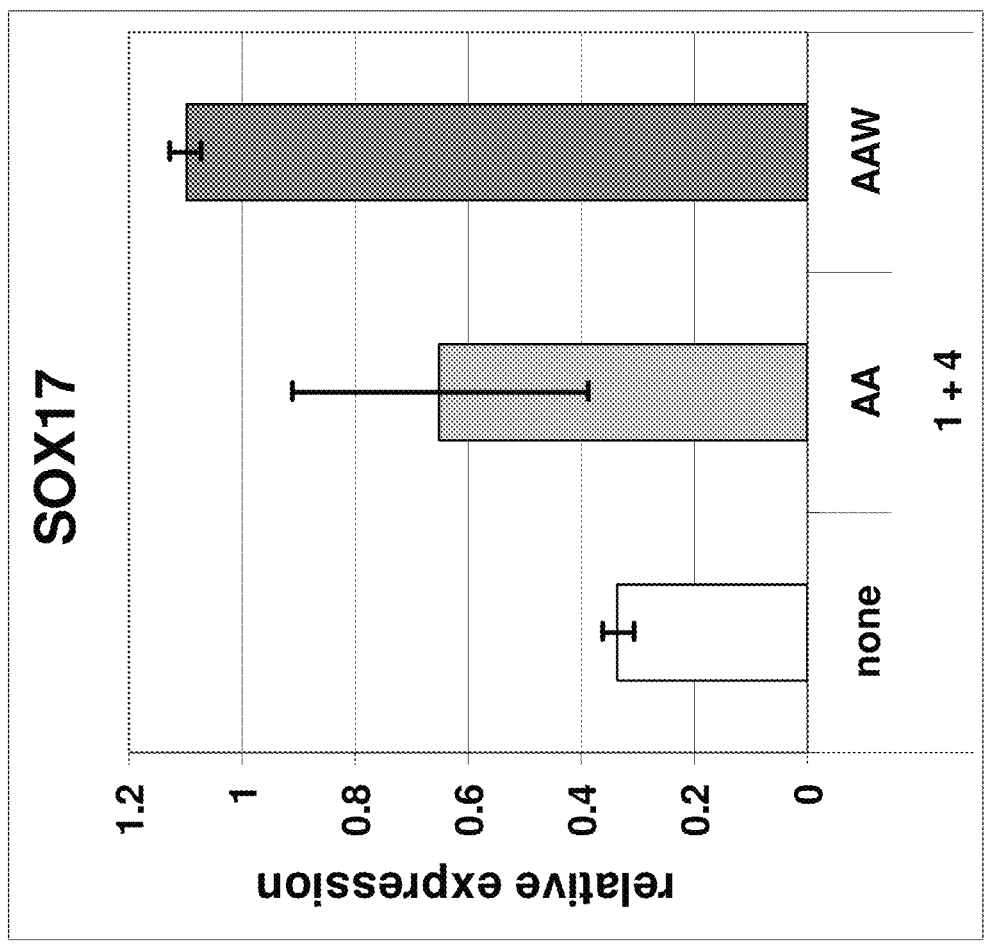
FIG. 23 is a bar chart showing that addition of Wnt3a to activin A and activin B treated cultures increases SOX17 expression above the levels induced by activin A and activin B alone.

In addition to the TGFβ family members, the Wnt family of molecules may play a role in specification and/or maintenance of definitive endoderm. The use of Wnt molecules was also beneficial for the differentiation of hESCs to definitive endoderm as indicated by the increased SOX17 gene expression in samples that were treated with activins plus Wnt3a over that of activins alone (FIG. 23).

Figure 24A:
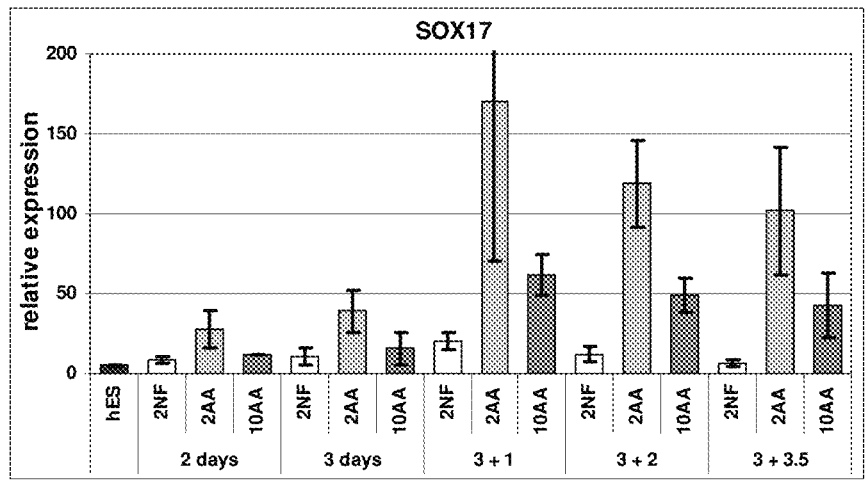
FIGS. 24A-24C are bar charts showing differentiation to definitive endoderm is enhanced in low FBS conditions. Treatment of hESCs with activins A and B in media containing 2% FBS (2AA) yields a 2-3 times greater level of SOX17 expression as compared to the same treatment in 10% FBS media (10AA) (panel A). Induction of the definitive endoderm marker MIXL1 (panel B) is also affected in the same way and the suppression of AFP (visceral endoderm) (panel C) is greater in 2% FBS than in 10% FBS conditions.
Figure 24B:
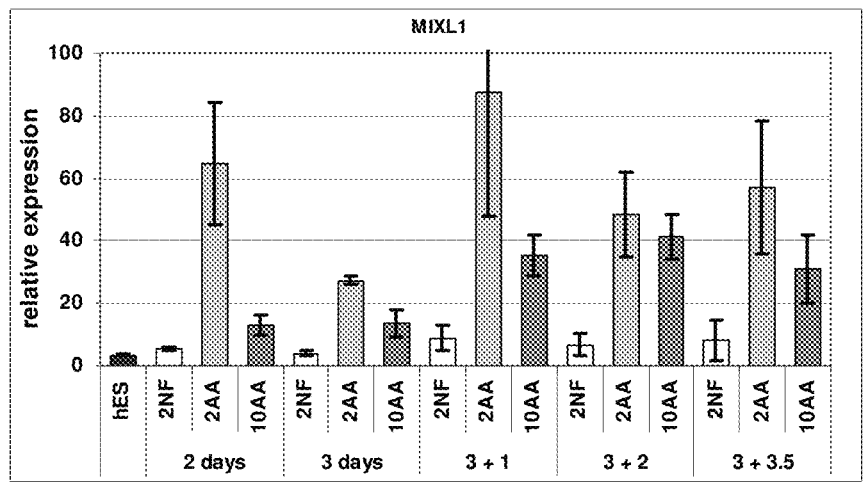
Figure 24C:
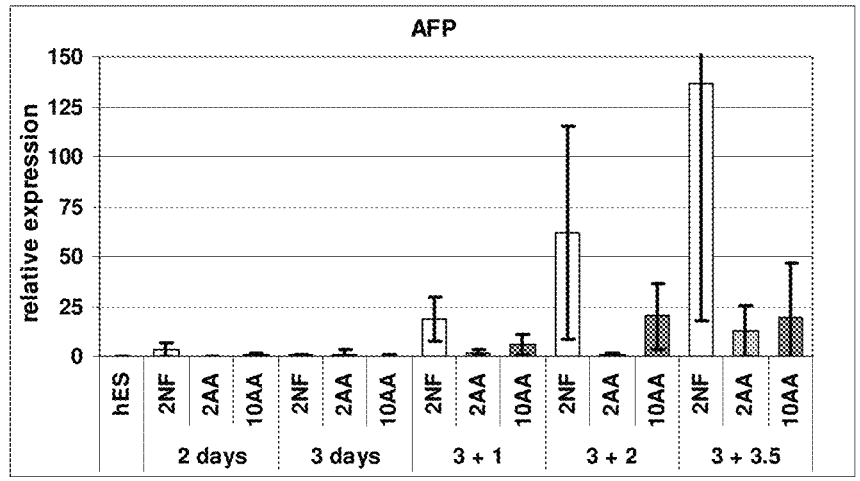

All of the experiments described above were performed using a tissue culture medium containing 10% serum with added factors. Surprisingly, we discovered that the concentration of serum had an effect on the level of SOX17 expression in the presence of added activins as shown in FIGS. 24A-24C. When serum levels were reduced from 10% to 2%, SOX17 expression tripled in the presence of activins A and B.

Finally, we demonstrated that activin induced SOX17$^+$ cells divide in culture as depicted in FIGS. 25A-25D. The arrows show cells labeled with SOX17/PCNA/DAPI that are in mitosis as evidenced by the PCNA/DAPI-labeled mitotic plate pattern and the phase contrast mitotic profile.

Example 7

Chemokine Receptor 4 (CXCR4) Expression Correlates with Markers for Definitive Endoderm and not Markers for Mesoderm, Ectoderm or Visceral Endoderm As described above, hESCs can be induced to differentiate to the definitive endoderm germ layer by the application of cytokines of the TGFβ family and more specifically of the activin/nodal subfamily Additionally, we have shown that the proportion of fetal bovine serum (FBS) in the differentiation culture medium effects the efficiency of definitive endoderm differentiation from hESCs. This effect is such that at a given concentration of activin A in the medium, higher levels of FBS will inhibit maximal differentiation to definitive endoderm. In the absence of exogenous activin A, differentiation of hESCs to the definitive endoderm lineage is very inefficient and the FBS concentration has much milder effects on the differentiation process of hESCs.

In these experiments, hESCs were differentiated by growing in RPMI medium (Invitrogen, Carlsbad, Calif.; cat #61870-036) supplemented with 0.5%, 2.0% or 10% FBS and either with or without 100 ng/ml activin A for 6 days. In addition, a gradient of FBS ranging from 0.5% to 2.0% over the first three days of differentiation was also used in conjunction with 100 ng/ml of activin A. After the 6 days, replicate samples were collected from each culture condition and analyzed for relative gene expression by real-time quantitative PCR. The remaining cells were fixed for immunofluorescent detection of SOX17 protein.

Figure 26:
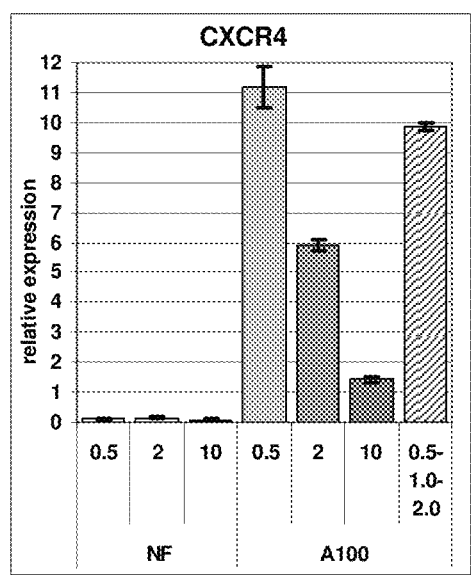
FIG. 26 is a bar chart showing the relative expression level of CXCR4 in differentiating hESCs under various media conditions.
Figure 27A:
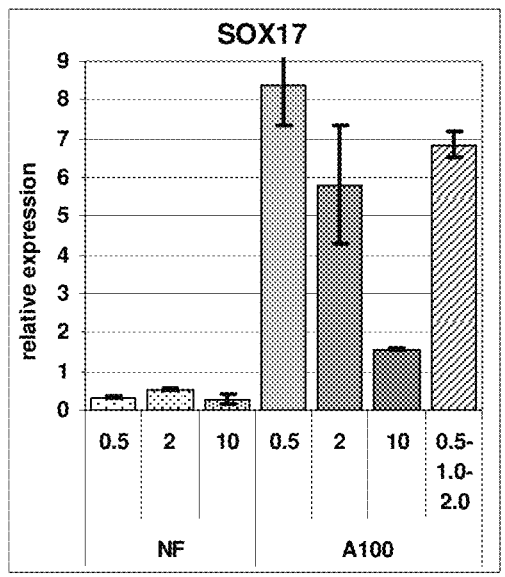
FIGS. 27A-27D are bar charts that show how a panel of definitive endoderm markers share a very similar pattern of expression to CXCR4 across the same differentiation treatments displayed in FIG. 26.
Figure 27B:
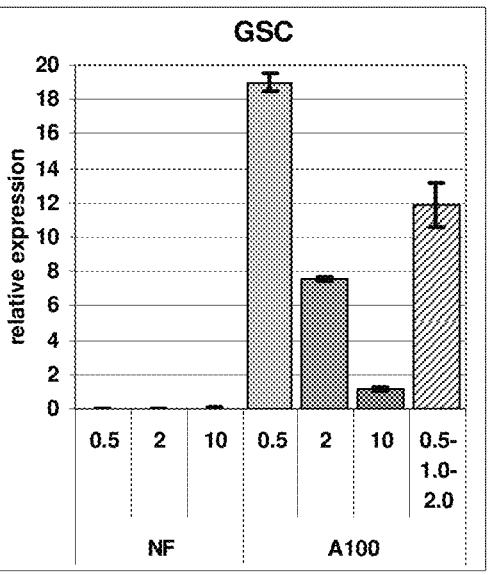
Figure 27C:
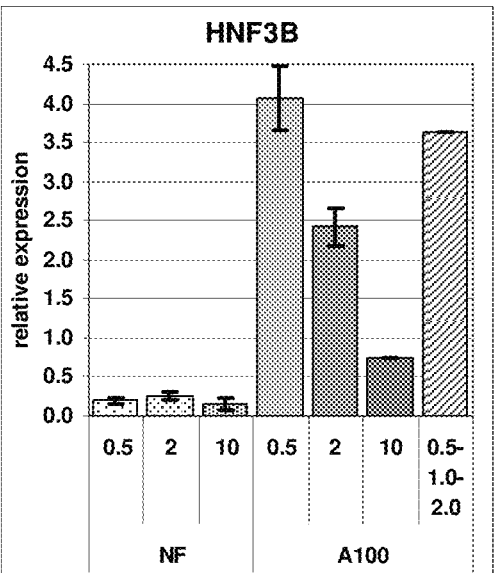
Figure 27D:
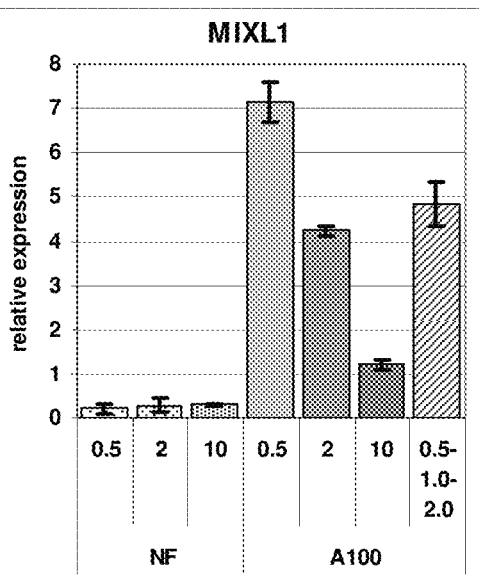

The expression levels of CXCR4 varied dramatically across the 7 culture conditions used (FIG. 26). In general, CXCR4 expression was high in activin A treated cultures (A100) and low in those which did not receive exogenous activin A (NF). In addition, among the A100 treated cultures, CXCR4 expression was highest when FBS concentration was lowest. There was a remarkable decrease in CXCR4 level in the 10% FBS condition such that the relative expression was more in line with the conditions that did not receive activin A (NF).

As described above, expression of the SOX17, GSC, MIXL1, and HNF313 genes is consistent with the characterization of a cell as definitive endoderm. The relative expression of these four genes across the 7 differentiation conditions mirrors that of CXCR4 (FIGS. 27A-27D). This demonstrates that CXCR4 is also a marker of definitive endoderm.

Ectoderm and mesoderm lineages can be distinguished from definitive endoderm by their expression of various markers. Early mesoderm expresses the genes Brachyury and MOX1 while nascent neuro-ectoderm expresses SOX1 and ZIC1. FIGS. 28A-28D demonstrate that the cultures which did not receive exogenous activin A were preferentially enriched for mesoderm and ectoderm gene expression and that among the activin A treated cultures, the 10% FBS condition also had increased levels of mesoderm and ectoderm marker expression. These patterns of expression were inverse to that of CXCR4 and indicated that CXCR4 was not highly expressed in mesoderm or ectoderm derived from hESCs at this developmental time period.

Figure 28A:
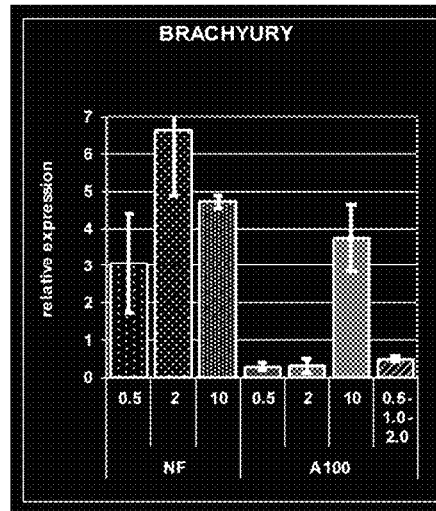
FIGS. 28A-28E are bar charts showing how markers for mesoderm (BRACHYURY, MOX1), ectoderm (SOX1, ZIC1) and visceral endoderm (SOX7) exhibit an inverse relationship to CXCR4 expression across the same treatments displayed in FIG. 26.
Figure 28B:
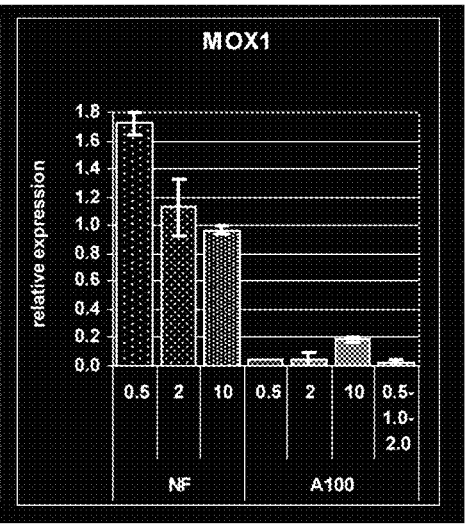
Figure 28C:
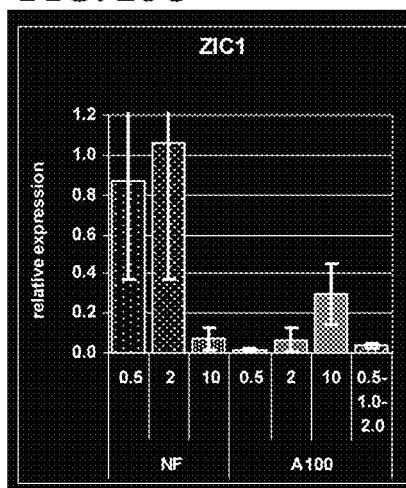
Figure 28D:
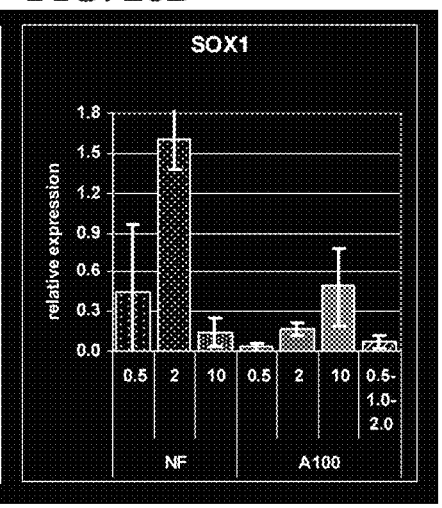
Figure 28E:
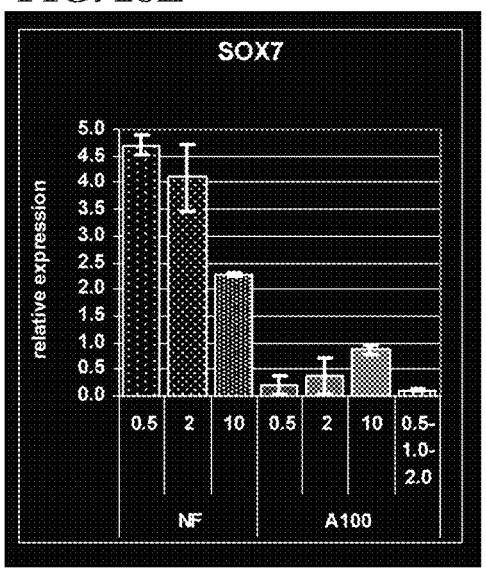

Early during mammalian development, differentiation to extra-embryonic lineages also occurs. Of particular relevance here is the differentiation of visceral endoderm that shares the expression of many genes in common with definitive endoderm, including SOX17. To distinguish definitive endoderm from extra-embryonic visceral endoderm one should examine a marker that is distinct between these two. SOX7 represents a marker that is expressed in the visceral endoderm but not in the definitive endoderm lineage. Thus, culture conditions that exhibit robust SOX17 gene expression in the absence of SOX7 expression are likely to contain definitive and not visceral endoderm. It is shown in FIG. 28E that SOX7 was highly expressed in cultures that did not receive activin A, SOX7 also exhibited increased expression even in the presence of activin A when FBS was included at 10%. This pattern is the inverse of the CXCR4 expression pattern and suggests that CXCR4 is not highly expressed in visceral endoderm.

The relative number of SOX17 immunoreactive (SOX17+) cells present in each of the differentiation conditions mentioned above was also determined. When hESCs were differentiated in the presence of high dose activin A and low FBS concentration (0.5%-2.0%) SOX17+ cells were ubiquitously distributed throughout the culture. When high dose activin A was used but FBS was included at 10% (v/v), the SOX17+ cells appeared at much lower frequency and always appeared in isolated clusters rather than evenly distributed throughout the culture (FIGS. 29A and 29C as well as 29B and 29E). A further decrease in SOX17+ cells was seen when no exogenous activin A was used. Under these conditions the SOX17+ cells also appeared in clusters and these clusters were smaller and much more rare than those found in the high activin A, low FBS treatment (FIGS. 29C and 29F). These results demonstrate that the CXCR4 expression patterns not only correspond to definitive endoderm gene expression but also to the number of definitive endoderm cells in each condition.

Example 8

Differentiation Conditions that Enrich for Definitive Endoderm Increase the Proportion of CXCR4 Positive Cells The dose of activin A also effects the efficiency at which definitive endoderm can be derived from hESCs. This example demonstrates that increasing the dose of activin A increases the proportion of CXCR4+ cells in the culture.

hESCs were differentiated in RPMI media supplemented with 0.5%-2% FBS (increased from 0.5% to 1.0% to 2.0% over the first 3 days of differentiation) and either 0, 10, or 100 ng/ml of activin A. After 7 days of differentiation the cells were dissociated in PBS without $Ca^{2+}/Mg^{2+}$ containing 2% FBS and 2 mM (EDTA) for 5 minutes at room temperature. The cells were filtered through 35 μm nylon filters, counted and pelleted. Pellets were resuspended in a small volume of 50% human serum/50% normal donkey serum and incubated for 2 minutes on ice to block non-specific antibody binding sites. To this, 1 μl of mouse anti-CXCR4 antibody (Abcam, cat #ab10403-100) was added per 50 μl (containing approximately $10^5$ cells) and labeling proceeded for 45 minutes on ice. Cells were washed by adding 5 ml of PBS containing 2% human serum (buffer) and pelleted. A second wash with 5 ml of buffer was completed then cells were resuspended in 50 μl buffer per $10^5$ cells. Secondary antibody (FITC conjugated donkey anti-mouse; Jackson ImmunoResearch, cat #715-096-151) was added at 5 μg/ml final concentration and allowed to label for 30 minutes followed by two washes in buffer as above. Cells were resuspended at $5\times10^6$ cells/ml in buffer and analyzed and sorted using a FACS Vantage (Beckton Dickenson) by the staff at the flow cytometry core facility (The Scripps Research Institute). Cells were collected directly into RLT lysis buffer (Qiagen) for subsequent isolation of total RNA for gene expression analysis by real-time quantitative PCR.

Figure 30A:
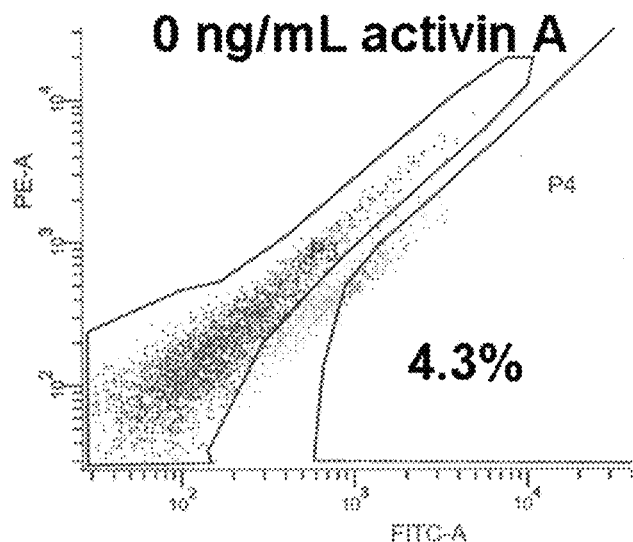
FIGS. 30A-30C are flow cytometry dot plots that demonstrate the increase in $CXCR4^+$ cell number with increasing concentration of activin A added to the differentiation media.
Figure 30B:
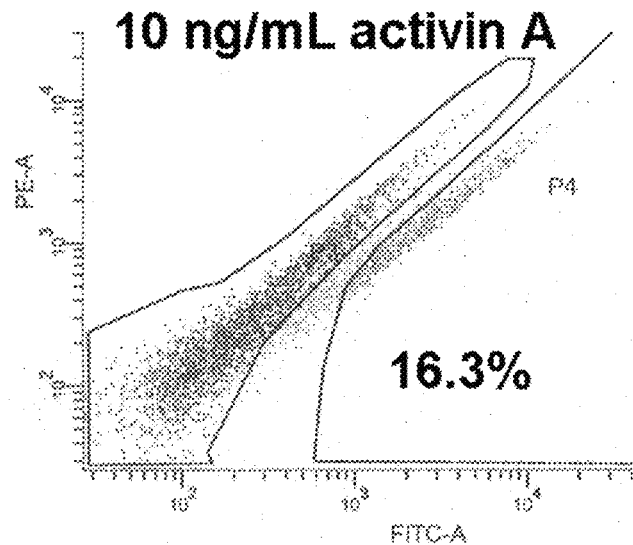
Figure 30C:
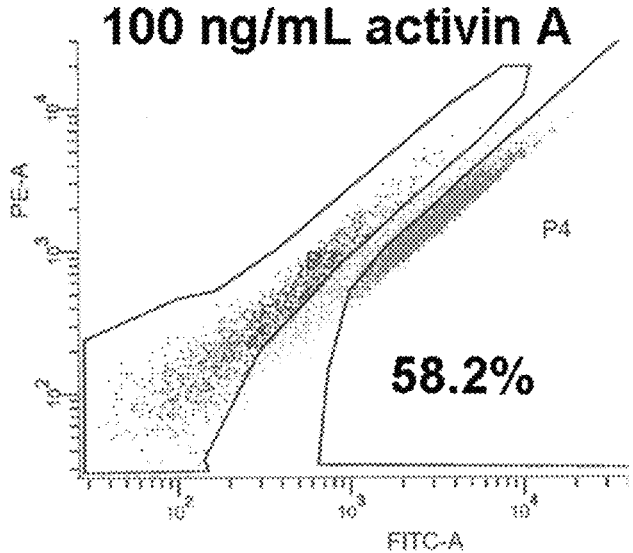
Figure 31A:
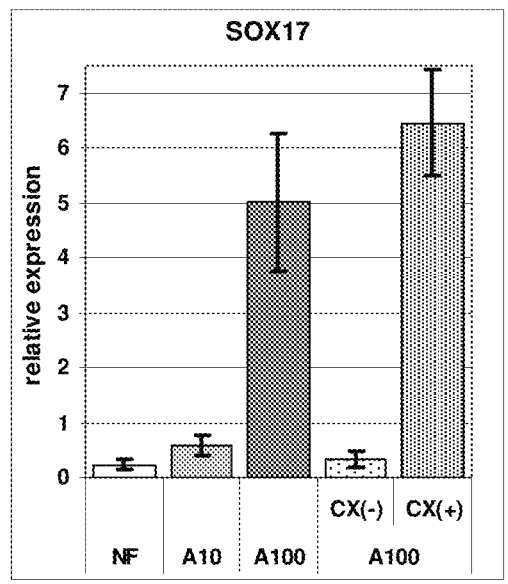
FIGS. 31A-31D are bar charts that show the $CXCR4^+$ cells isolated from the high dose activin A treatment (A100-CX+) are even further enriched for definitive endoderm markers than the parent population (A100).
Figure 31B:
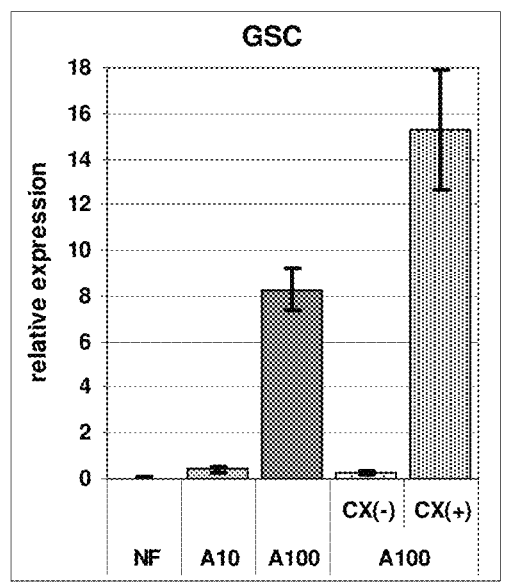
Figure 31C:
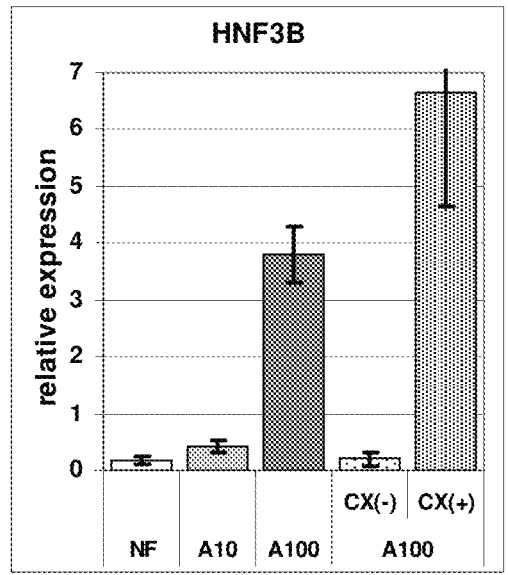
Figure 31D:
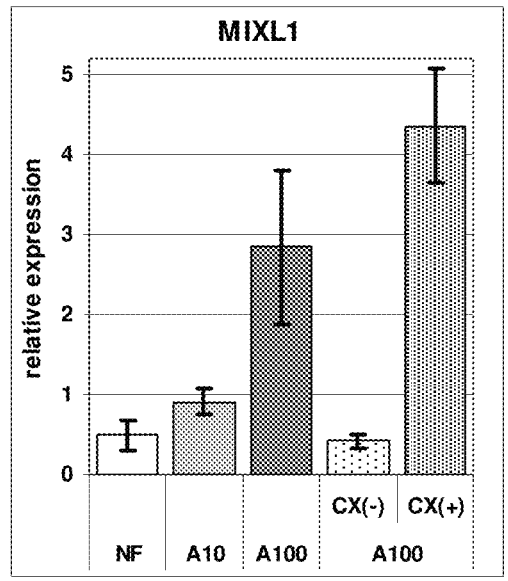

The number of CXCR4+ cells as determined by flow cytometry were observed to increase dramatically as the dose of activin A was increased in the differentiation culture media (FIGS. 30A-30C). The CXCR4+ cells were those falling within the R4 gate and this gate was set using a secondary antibody-only control for which 0.2% of events were located in the R4 gate. The dramatically increased numbers of CXCR4+ cells correlates with a robust increase in definitive endoderm gene expression as activin A dose is increased (FIGS. 31A-31D).

Example 9

Isolation of CXCR4 Positive Cells Enriches for Definitive Endoderm Gene Expression and Depletes Cells Expressing Markers of Mesoderm, Ectoderm and Visceral Endoderm The CXCR4+ and CXCR4− cells identified in Example 8 above were collected and analyzed for relative gene expression and the gene expression of the parent populations was determined simultaneously.

Figure 32:
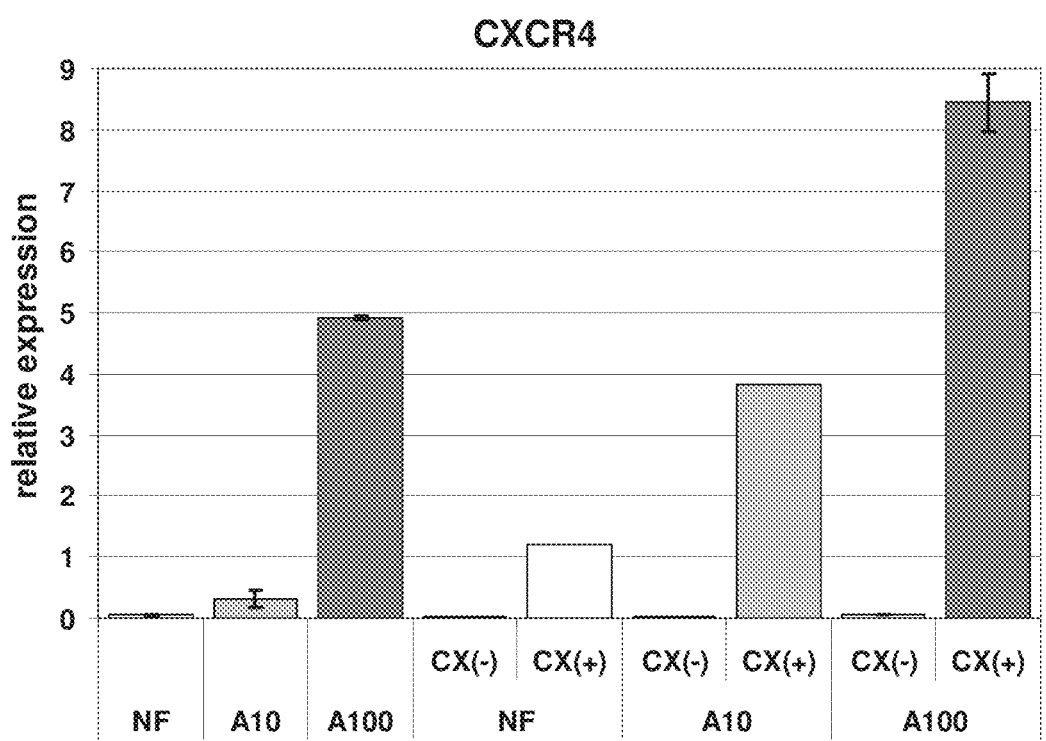
FIG. 32 is a bar chart showing gene expression from $CXCR4^+$ and $CXCR4^-$ cells isolated using fluorescence-activated cell sorting (FACS) as well as gene expression in the parent populations. This demonstrates that the $CXCR4^+$ cells contain essentially all the CXCR4 gene expression present in each parent population and the $CXCR4^-$ populations contain very little or no CXCR4 gene expression.
Figure 33A:
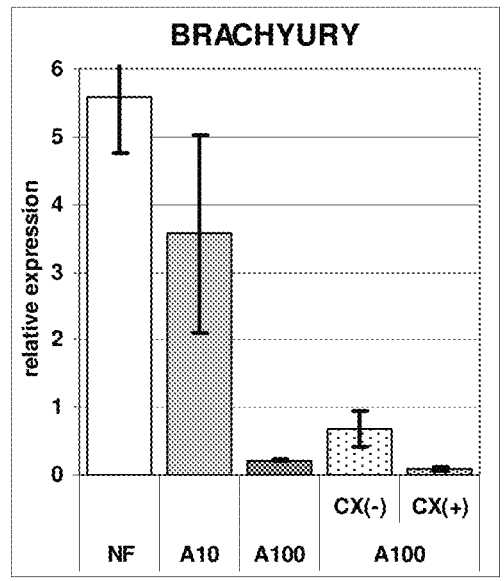
FIGS. 33A-33D are bar charts that demonstrate the depletion of mesoderm (BRACHYURY, MOX1), ectoderm (ZIC1) and visceral endoderm (SOX7) gene expression in the $CXCR4^+$ cells isolated from the high dose activin A treatment which is already suppressed in expression of these non-definitive endoderm markers.
Figure 33B:
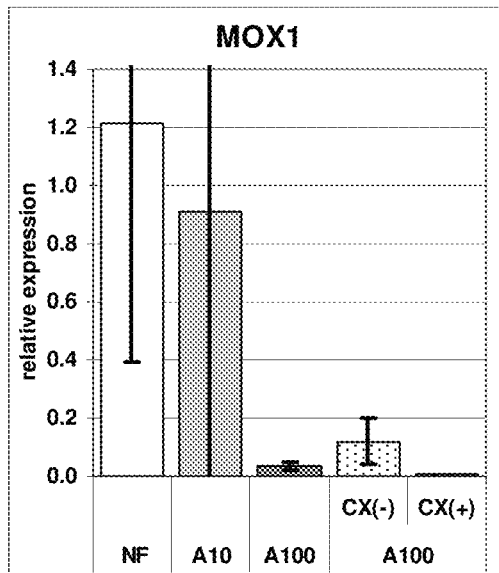
Figure 33C:
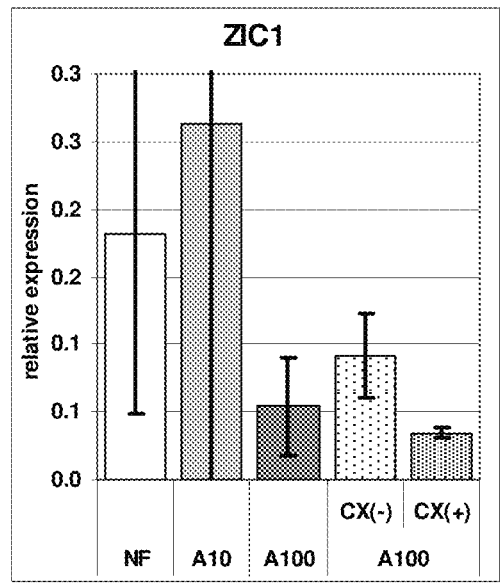
Figure 33D:
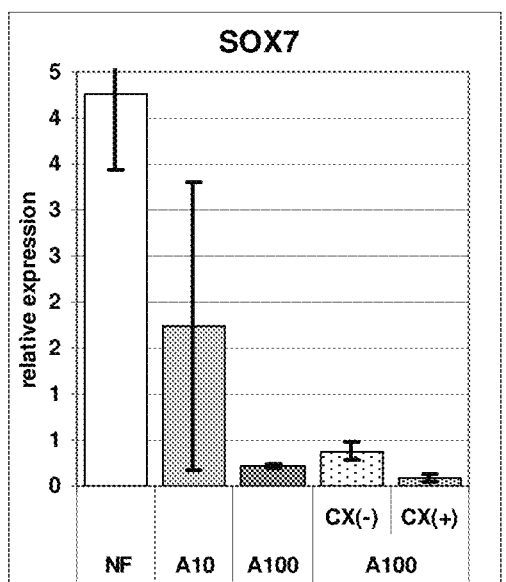
Figure 34A:
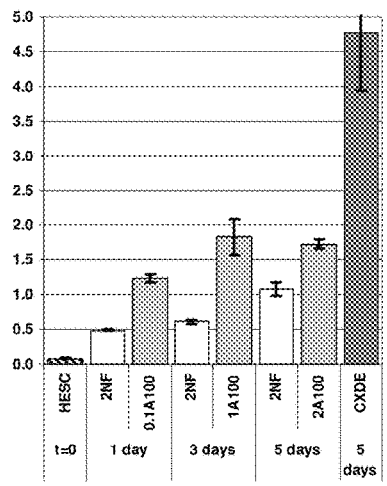
FIGS. 34A-34M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml activin A; 1A100 indicates cells treated with 1% FBS, 100 ng/ml activin A; and 2A100 indicates cells treated with 2% FBS, 100 ng/ml activin A.
Figure 34B:
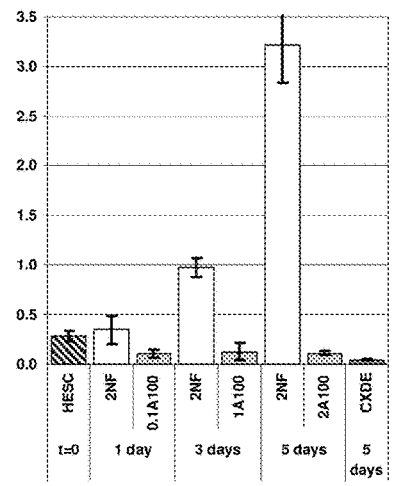
Figure 34C:
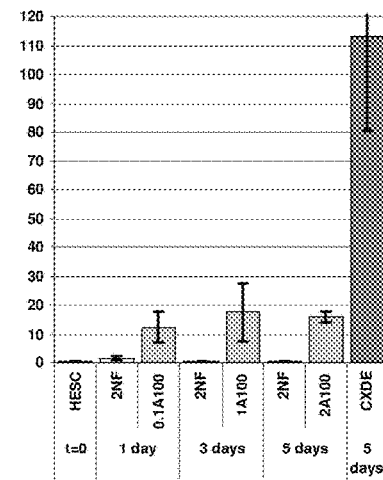
Figure 34D:
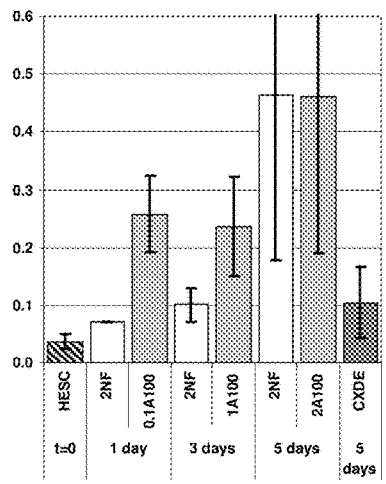
Figure 34E:
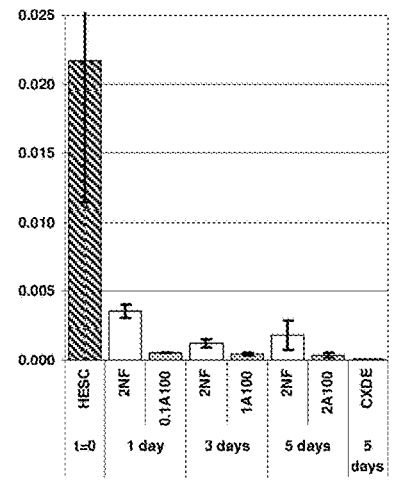
Figure 34F:
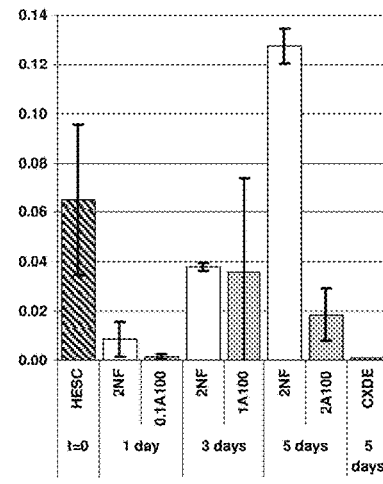
Figure 34G:
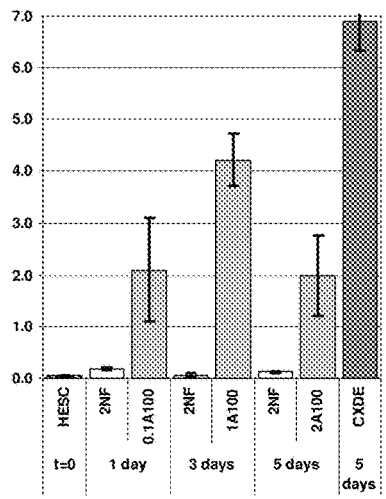
Figure 34H:
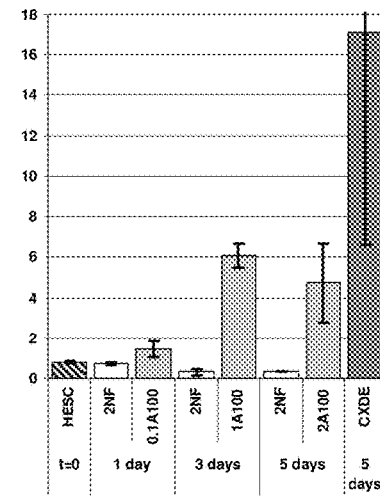
Figure 34I:
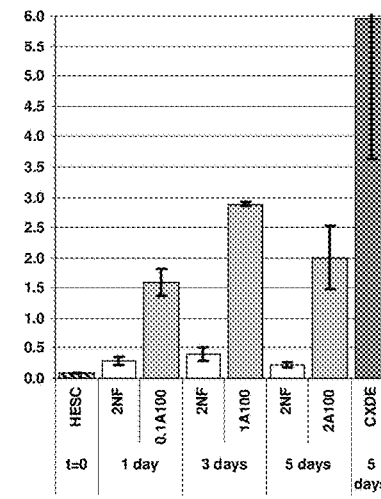
Figure 34J:
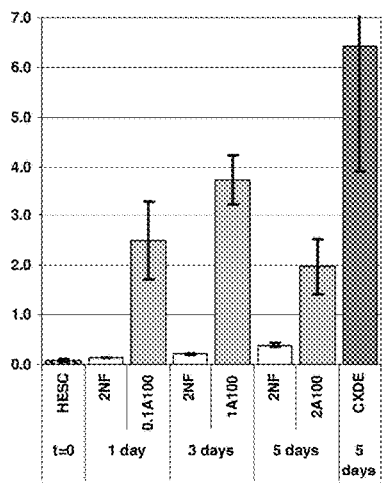
Figure 34K:
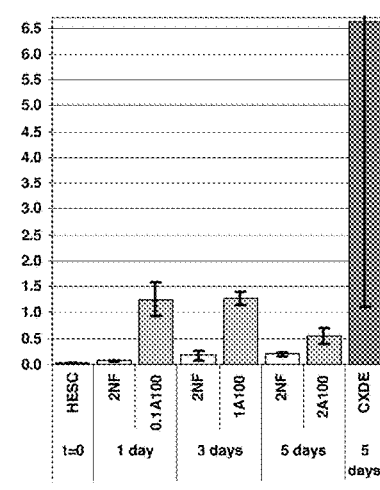
Figure 34L:
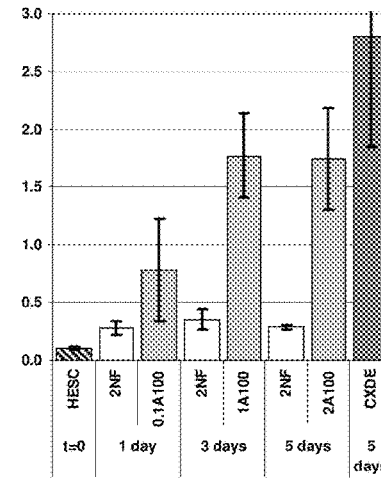
Figure 34M:
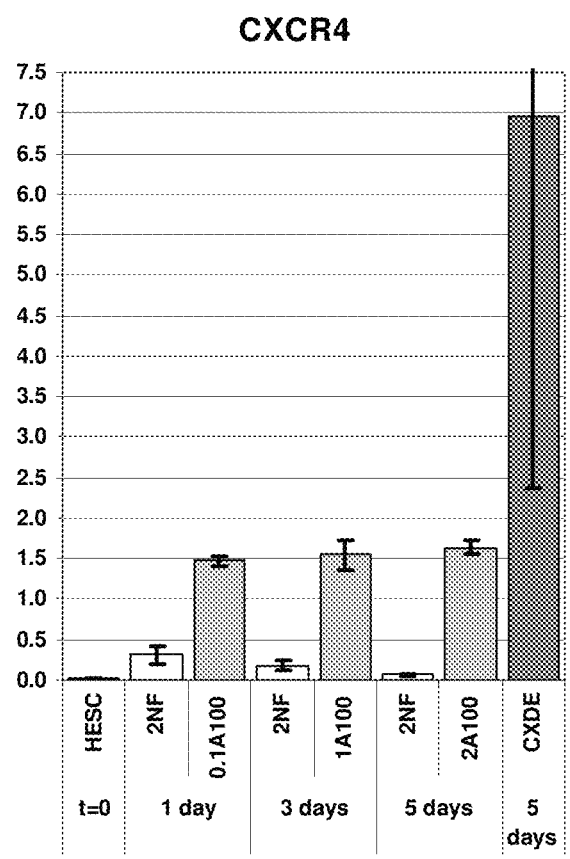

The relative levels of CXCR4 gene expression was dramatically increased with increasing dose of activin A (FIG. 32). This correlated very well with the activin A dose-dependent increase of CXCR4+ cells (FIGS. 30A-30C). It is also clear that isolation of the CXCR4+ cells from each population accounted for nearly all of the CXCR4 gene expression in that population. This demonstrates the efficiency of the FACS method for collecting these cells.

Gene expression analysis revealed that the CXCR4+ cells contain not only the majority of the CXCR4 gene expression, but they also contained gene expression for other markers of definitive endoderm. As shown in FIGS. 31A-31D, the CXCR4+ cells were further enriched over the parent A100 population for SOX17, GSC, HNF3B, and MIXL1. In addition, the CXCR4− fraction contained very little gene expression for these definitive endoderm markers. Moreover, the CXCR4+ and CXCR4− populations displayed the inverse pattern of gene expression for markers of mesoderm, ectoderm and extra-embryonic endoderm. FIGS. 33A-33D shows that the CXCR4+ cells were depleted for gene expression of Brachyury, MOX1, ZIC1, and SOX7 relative to the A100 parent population. This A100 parent population was already low in expression of these markers relative to the low dose or no activin A conditions. These results show that the isolation of CXCR4+ cells from hESCs differentiated in the presence of high activin A yields a population that is highly enriched for and substantially pure definitive endoderm.

Example 10

Quantitation of Definitive Endoderm Cells in a Cell Population Using CXCR4

To confirm the quantitation of the proportion of definitive endoderm cells present in a cell culture or cell population as determined previously herein and as determined in U.S. Provisional Patent Application No. 60/532,004, entitled DEFINITIVE ENDODERM, filed Dec. 23, 2003, the disclosure of which is incorporated herein by reference in its entirety, cells expressing CXCR4 and other markers of definitive endoderm were analyzed by FACS.

Using the methods such as those described in the above Examples, hESCs were differentiated to produce definitive endoderm. In particular, to increase the yield and purity in differentiating cell cultures, the serum concentration of the medium was controlled as follows: 0.2% FBS on day 1, 1.0% FBS on day 2 and 2.0% FBS on days 3-6. Differentiated cultures were sorted by FACS using three cell surface epitopes, E-Cadherin, CXCR4, and Thrombomodulin. Sorted cell populations were then analyzed by Q-PCR to determine relative expression levels of markers for definitive and extraembryonic-endoderm as well as other cell types. CXCR4 sorted cells taken from optimally differentiated cultures resulted in the isolation of definitive endoderm cells that were >98% pure.

Table 2 shows the results of a marker analysis for a definitive endoderm culture that was differentiated from hESCs using the methods described herein.

TABLE 2

Composition of Definitive Endoderm Cultures

| Marker(s) | Percent of culture | Percent Definitive Endoderm | Percent Extraembryonic endoderm | Percent hES cells |
|---|---|---|---|---|
| SOX17 | 70-80 | 100 | | |
| Thrombomodulin | <2 | 0 | 75 | |
| AFP | <1 | 0 | 25 | |
| CXCR4 | 70-80 | 100 | 0 | |
| ECAD | 10 | 0 | | 100 |
| other (ECAD neg.) | 10-20 | | | |
| Total | 100 | 100 | 100 | 100 |

In particular, Table 2 indicates that CXCR4 and SOX17 positive cells (endoderm) comprised from 70%-80% of the cells in the cell culture. Of these SOX17-expressing cells, less than 2% expressed TM (parietal endoderm) and less than 1% expressed AFP (visceral endoderm). After subtracting the proportion of TM-positive and AFP-positive cells (combined parietal and visceral endoderm; 3% total) from the proportion of SOX17/CXCR4 positive cells, it can be seen that about 67% to about 77% of the cell culture was definitive endoderm. Approximately 10% of the cells were positive for E-Cadherin (ECAD), which is a marker for hESCs, and about 10-20% of the cells were of other cell types.

We have discovered that the purity of definitive endoderm in the differentiating cell cultures that are obtained prior to FACS separation can be improved as compared to the above-described low serum procedure by maintaining the FBS concentration at <0.5% throughout the 5-6 day differentiation procedure. However, maintaining the cell culture at <0.5% throughout the 5-6 day differentiation procedure also results in a reduced number of total definitive endoderm cells that are produced.

Definitive endoderm cells produced by methods described herein have been maintained and expanded in culture in the presence of activin for greater than 50 days without appreciable differentiation. In such cases, SOX17, CXCR4, MIXL1, GATA4, HNF3I3 expression is maintained over the culture period. Additionally, TM, SPARC, OCT4, AFP, SOX7, ZIC1 and BRACH were not detected in these cultures. It is likely that such cells can be maintained and expanded in culture for substantially longer than 50 days without appreciable differentiation.

Example 11

Additional Marker of Definitive Endoderm Cells

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/ml recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/ml of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis. Immunopurification was achieved for hESCs using SSEA4 antigen (R&D Systems, cat #FAB1435P) and for definitive endoderm using CXCR4 (R&D Systems, cat #FAB170P). Cells were dissociated using trypsin/EDTA (Invitrogen, cat #25300-054), washed in phosphate buffered saline (PBS) containing 2% human serum and resuspended in 100% human serum on ice for 10 minutes to block non-specific binding. Staining was carried out for 30 minutes on ice by adding 200 µl of phycoerythrin-conjugated antibody to $5 \times 10^6$ cells in 800 µl human serum. Cells were washed twice with 8 ml of PBS buffer and resuspended in 1 ml of the same. FACS isolation was carried out by the core facility of The Scripps Research Institute using a FACS Vantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm. Genes that exhibited a robust upward change in expression level over that found in hESCs were selected as new candidate markers that are highly characteristic of definitive endoderm. Select genes were assayed by Q-PCR, as described above, to verify the gene expression changes found on the gene chip and also to investigate the expression pattern of these genes during a time course of hESC differentiation.

FIGS. 34A-34M show the gene expression results for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified hESCs. A comparison of FIGS. 34C and 34G-34M demonstrates that the six marker genes, FGF17, VWF, CALCR, FOXQ1, CMKOR1 and CRIP1, exhibit an expression pattern that is almost identical to each other and which is also identical to the pattern of expression of CXCR4 and the ratio of SOX17/SOX7. As described previously, SOX17 is expressed in both the definitive endoderm as well as in the SOX7-expressing extra-embryonic endoderm. Since SOX7 is not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are likely markers of definitive endoderm and that they are not significantly expressed in extra-embryonic endoderm cells.

It will be appreciated that the Q-PCR results described herein can be further confirmed by ICC.

Example 12

Retinoic Acid and FGF-10 Induces PDX1 Specifically in Definitive Endoderm Cultures The following experiment demonstrates that RA and FGF-10 induces the expression of PDX1 in definitive endoderm cells.

Human embryonic stem cells were cultured with or without activins for four days. On day four, 1 µM RA and 50 ng/ml FGF-10 were added to the cell culture. Forty-eight hours after the RA/FGF-10 addition, the expression of the PDX1 marker gene and other marker genes not specific to foregut endoderm were quantitated by Q-PCR.

Figure 35:
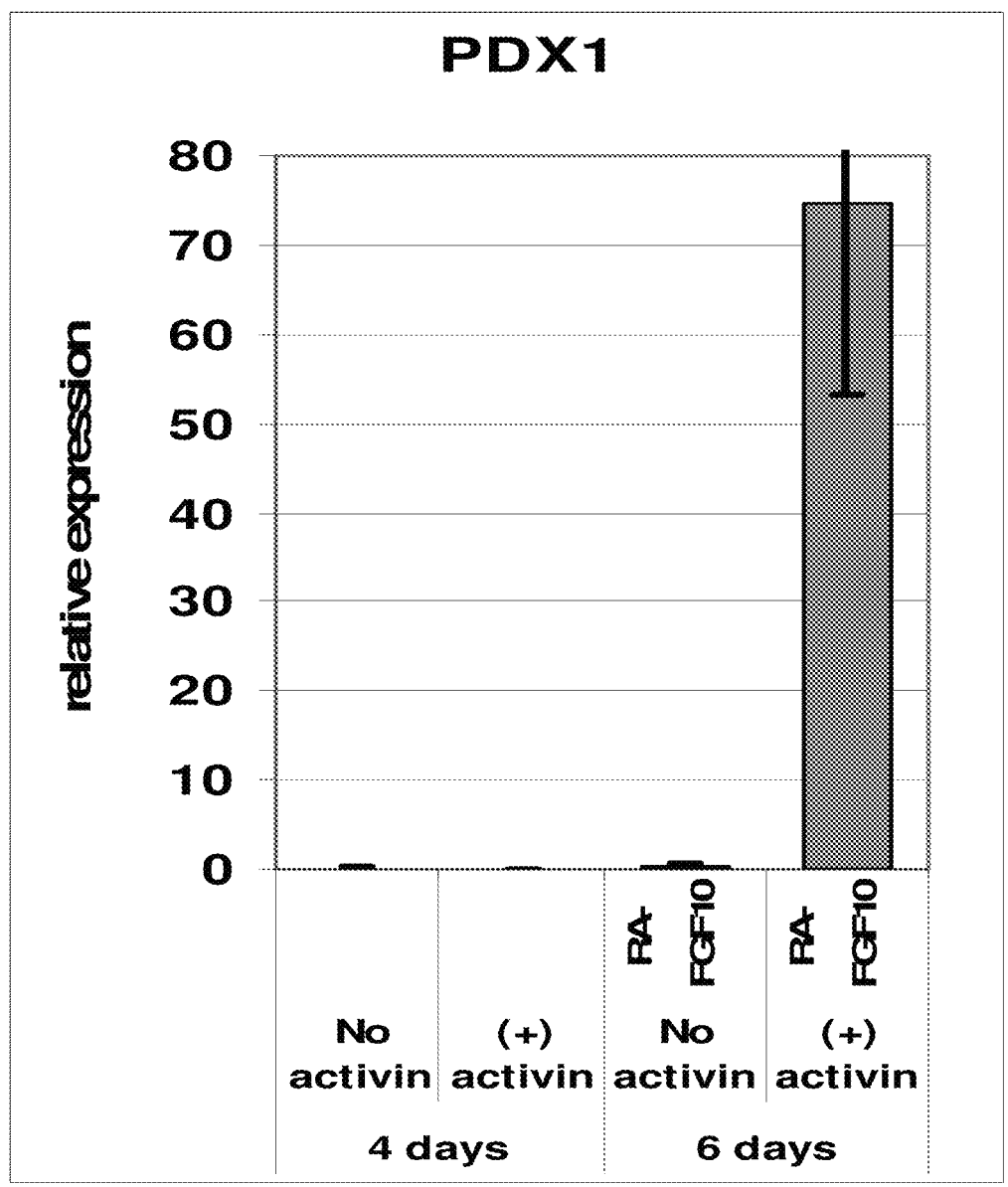
FIG. 35 is a chart which shows the relative expression of the PDX1 gene in a culture of hESCs after 4 days and 6 days with and without activin in the presence of retinoic acid (RA) and fibroblast growth factor (FGF-10) added on day 4.
Figure 36A:
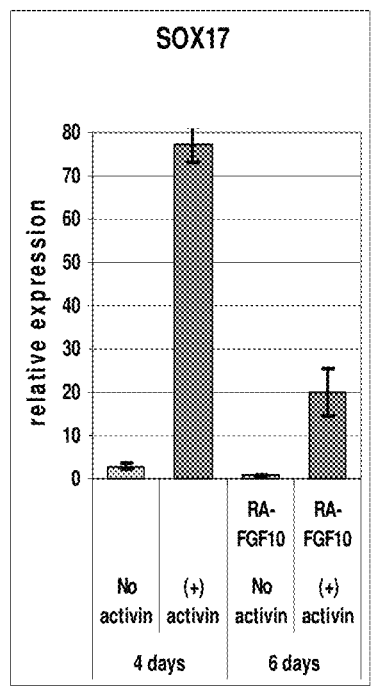
FIGS. 36A-36F are charts which show the relative expression of marker genes in a culture of hESCs after 4 days and 6 days with and without activin in the presence of retinoic acid (RA) and fibroblast growth factor (FGF-10) added on day 4. The panels show the relative levels of expression of the following marker genes: (A) SOX17; (B) SOX7; (C) AFP; (D) SOX1; (E) ZIC1; and (F) NFM.
Figure 36B:
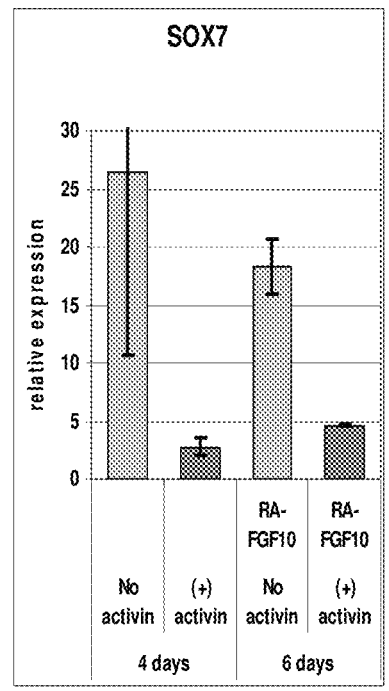
Figure 36C:
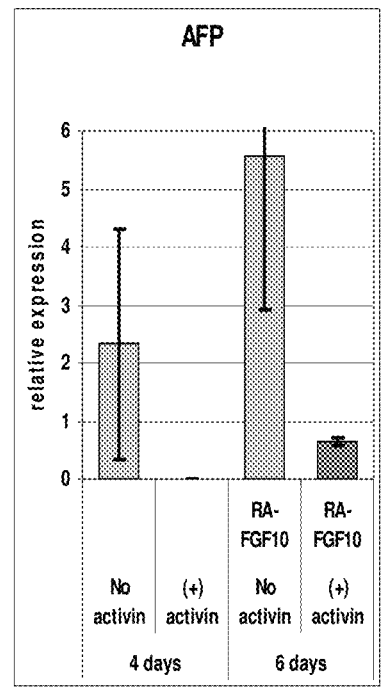
Figure 36D:
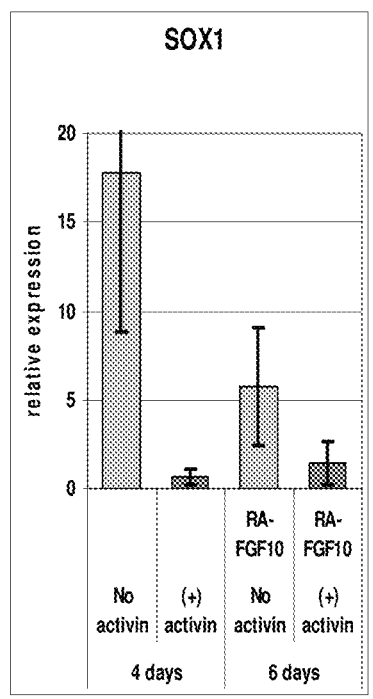
Figure 36E:
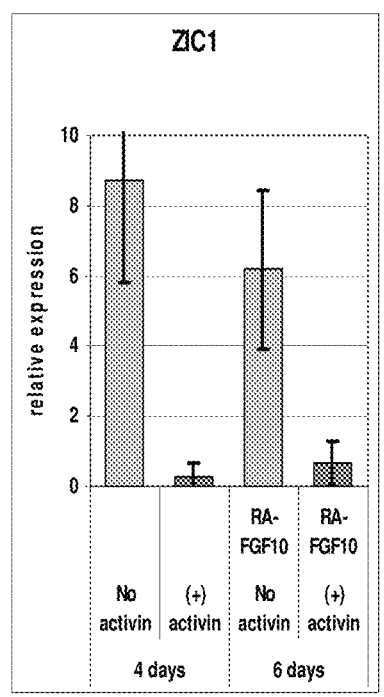
Figure 36F:
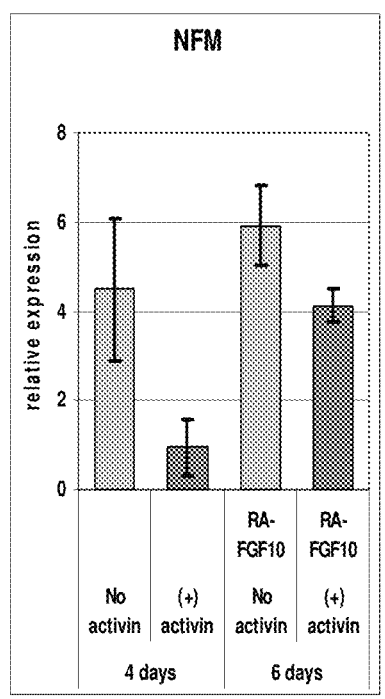

The application of RA to definitive endoderm cells caused a robust increase in PDX1 gene expression (see FIG. 35) without increasing the expression of visceral endoderm (SOX7, AFP), neural (SOX1, ZIC1), or neuronal (NFM) gene expression markers (see FIGS. 36A-36F). PDX1 gene expression was induced to levels approximately 500-fold higher than observed in definitive endoderm after 48 hours exposure to 1 µM RA and 50 ng/ml FGF-10. Furthermore, these results show that substantial PDX1 induction occurred only in cell cultures which had been previously differentiated to definitive endoderm (SOX17) as indicated by the 160-fold higher PDX1 expression found in the activin treated cell cultures relative to those cultures that received no activin prior to RA application.

Example 13

FGF-10 Provides Additional Increase in PDX1 Expression Over RA Alone

This Example shows that the combination of RA and FGF-10 induces PDX1 expression to a greater extent than RA alone.

As in the previous Example, hESCs were cultured with or without activins for four days. On day four, the cells were treated with one of the following: 1 µM RA alone; 1 µM RA in combination with either FGF-4 or FGF-10; or 1 µM RA in combination with both FGF-4 and FGF-10. The expression of PDX1, SOX7 and NFM were quantitated by Q-PCR ninety six hours after RA or RA/FGF.

The treatment of hESC cultures with activin followed by retinoic acid induced a 60-fold increase in PDX1 gene expression. The addition of FGF-4 to the RA treatment induced slightly more PDX1 (approximately 3-fold over RA alone). However, by adding FGF-10 and retinoic acid together, the induction of PDX1 was further enhanced 60-fold over RA alone (see FIG. 37A). This very robust PDX1 induction was greater than 1400-fold higher than with no activin or RA/FGF treatment. Interestingly, addition of FGF-4 and FGF-10 simultaneously abolished the beneficial effect of the FGF-10, producing only the modest PDX1 increase attributed to FGF-4 addition.

Figures 37A, 37B, 37C:
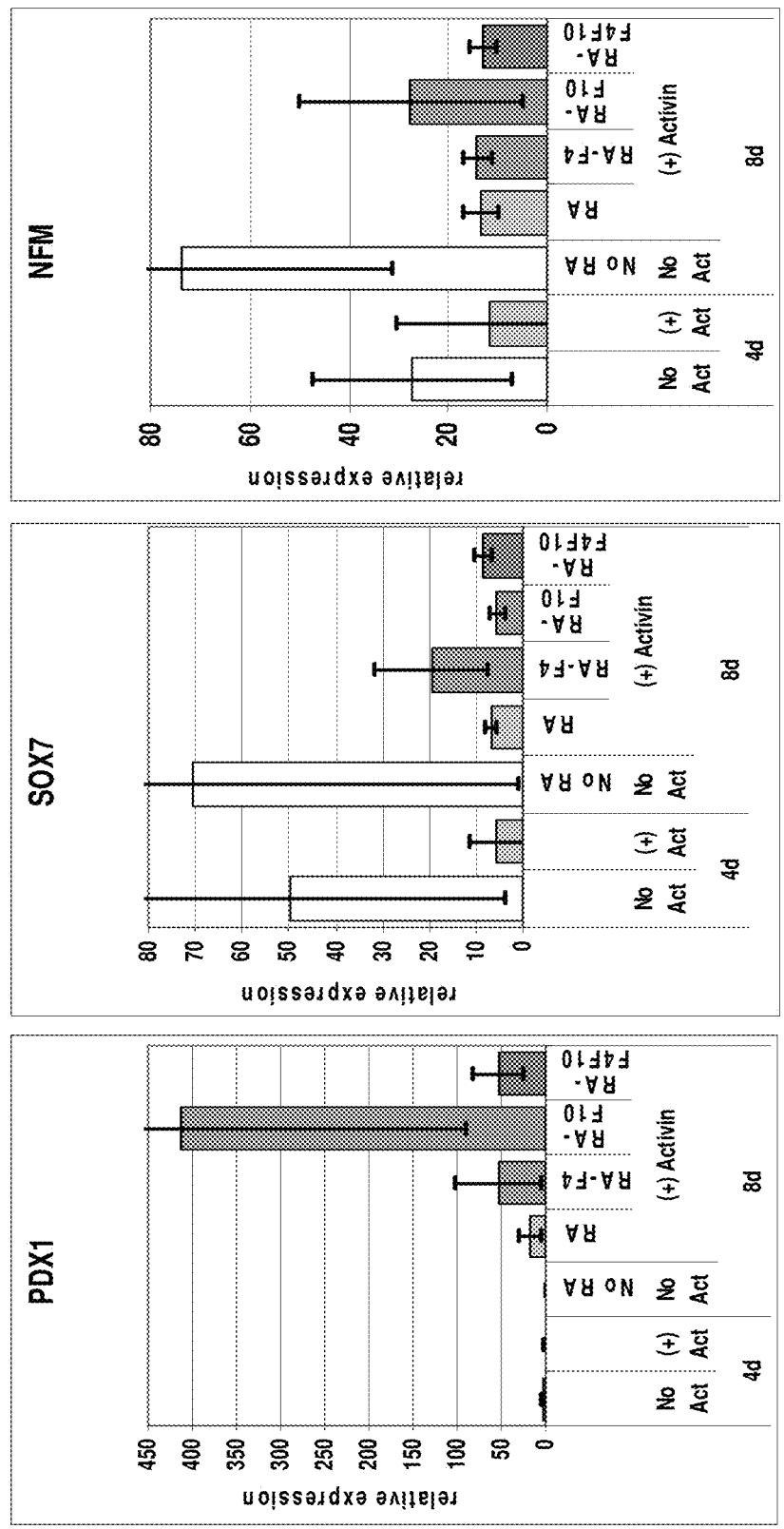
FIGS. 37A-37C are charts which show the relative expression of marker genes in a culture of hESCs after 4 days and 8 days with and without activin in the presence or absence of combinations of retinoic acid (RA), fibroblast growth factor (FGF-10) and fibroblast growth factor (FGF-4) added on day 4. The panels show the relative levels of expression of the following marker genes: (A) PDX1; (B) SOX7; and (C) NFM.

Addition of RA/FGF-4 or RA/FGF-10 combinations did not increase the expression of marker genes not associated with foregut endoderm when compared to cells not exposed to RA/FGF combinations (see FIGS. 37B-37C).

Example 14

Retinoic Acid Dose Affects Anterior-Posterior (A-P) Position In Vitro

To determine whether the dose of RA affects A-P position in in vitro cell cultures, the following experiment was performed.

Human embryonic stem cells were cultured with or without activins for four days. On day four, FGF-10 at 50 ng/ml was added to the culture in combination with RA at 0.04 µM, 0.2 µM or 1.0 µM. The expression of the PDX1 marker gene as well as other markers not specific for foregut endoderm were quantitated by Q-PCR.

Figure 38A:
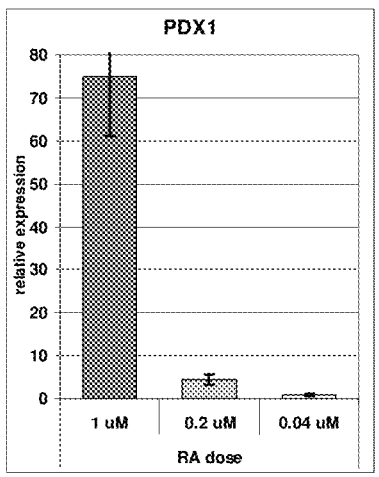
FIGS. 38A-38G are charts which show the relative expression of marker genes in a culture of definitive endoderm cells contacted with 50 ng/ml FGF-10 in combination with either 1 µM, 0.2 µM or 0.04 µM retinoic acid (RA) added on day 4. The panels show the relative levels of expression of the following marker genes: (A) PDX1; (B) HOXA3; (C) HOXC6; (D) HOXA13; (E) CDX1; (F) SOX1; and (G) NFM.
Figure 38B:
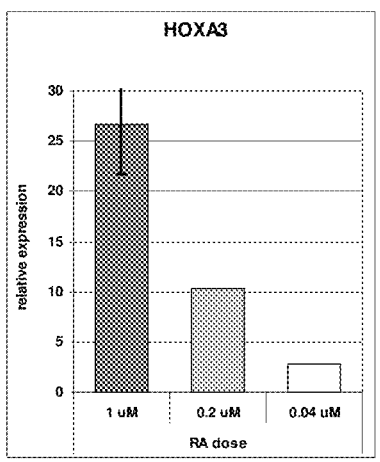
Figure 38C:
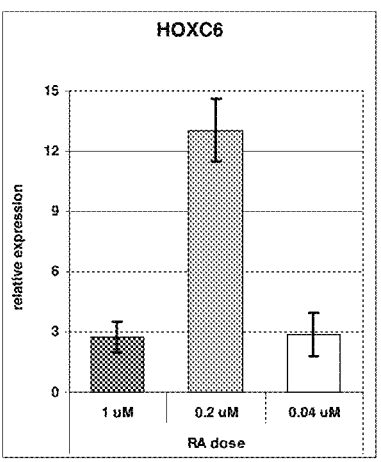
Figure 38D:
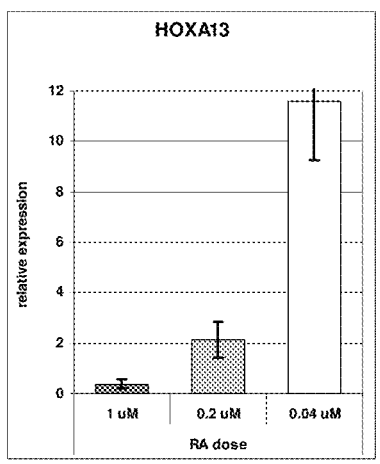
Figure 38E:
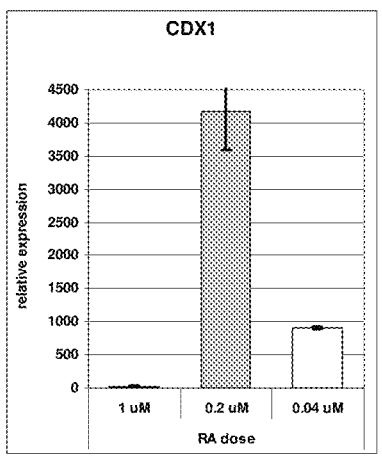
Figure 38F:
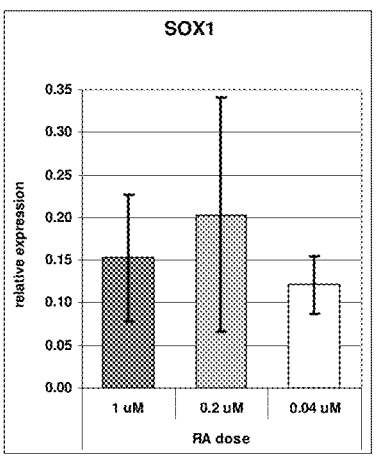
Figure 38G:
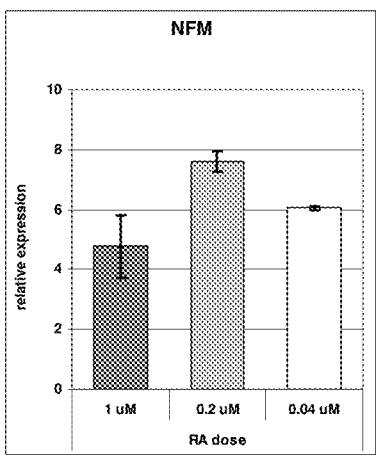
Figure 39A:
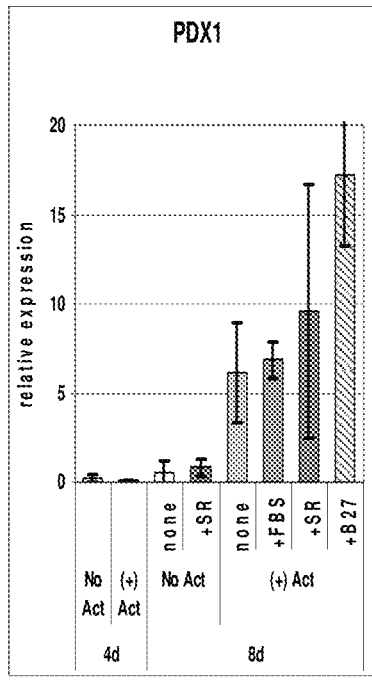
FIGS. 39A-39E are charts which show the relative expression of marker genes in a culture of hESCs after 4 days and 8 days with and without activin in the presence of combinations of retinoic acid (RA), fibroblast growth factor (FGF-10) and one of the following: serum replacement (SR), fetal bovine serum (FBS) or B27. The panels show the relative levels of expression of the following marker genes: (A) PDX1; (B) SOX7; (C) AFP; (D) ZIC1; and (E) NFM.
Figure 39B:
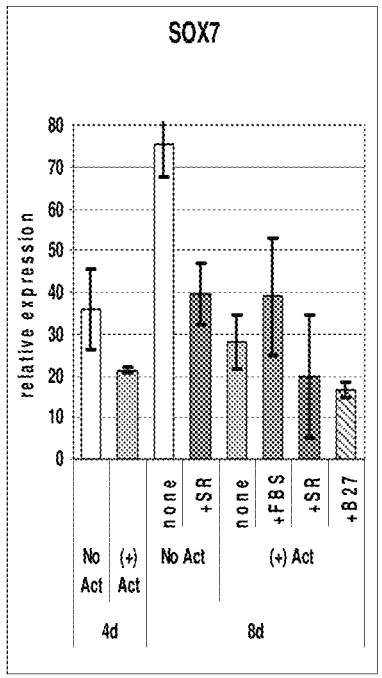
Figure 39C:
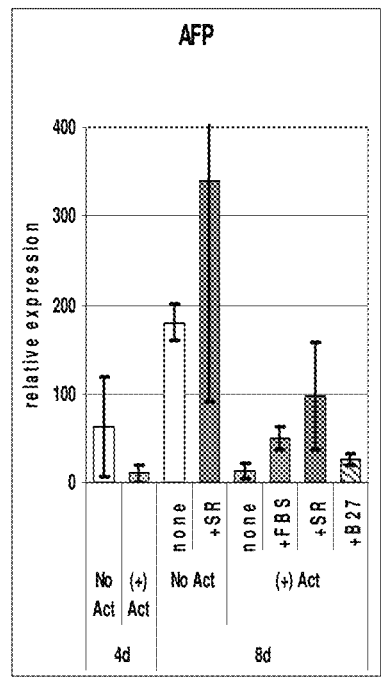
Figure 39D:
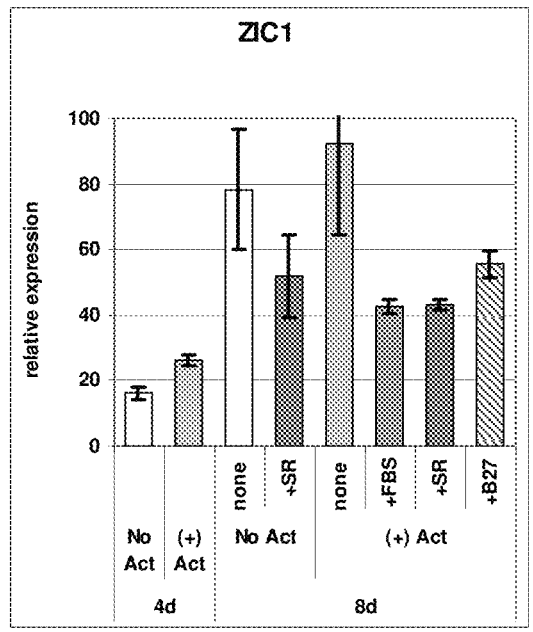
Figure 39E:
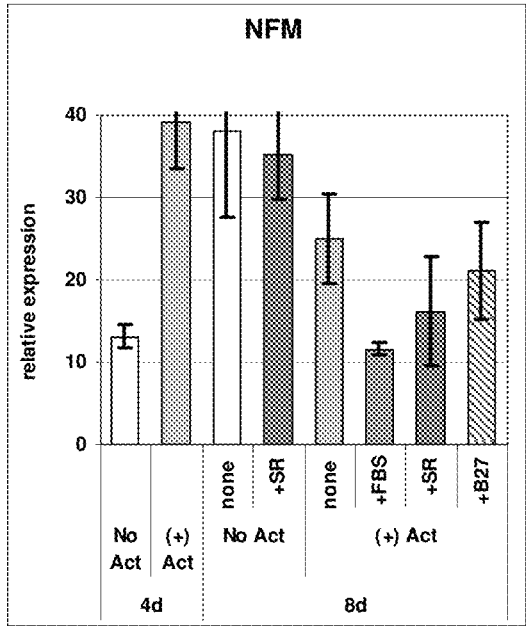

The addition of retinoic acid at various doses, in combination with FGF-10 at 50 ng/ml, induced differential gene expression patterns that correlate with specific anterior-posterior positional patterns. The highest dose of RA (1 µM) preferentially induced expression of anterior endoderm marker (HOXA3) and also produced the most robust increase in PDX1 (FIGS. 38A-38B). The middle dose of RA (0.2 µM) induced midgut endoderm markers (CDX1, HOXC6) (see FIGS. 38C and 41E), while the lowest dose of RA (0.04 µM) preferentially induced a marker of hindgut endoderm (HOXA13) (see FIG. 38D). The RA dose had essentially no effect on the relative expression of either neural (SOX1) or neuronal (NFM) markers (see FIGS. 38F-38G). This example highlights the use of RA as a morphogen in vitro and in particular as a morphogen of endoderm derivatives of differentiating hESCs.

Example 15

Use of B27 Supplement Enhances Expression of PDX1

PDX1 expression in definitive endoderm can be influenced by the use of a number of factors and cell growth/differentiation conditions. In the following experiment, we show that the use of B27 supplement enhances the expression of PDX1 in definitive endoderm cells.

Human embryonic stem cells were induced to differentiate to definitive endoderm by treatment of undifferentiated hES cells grown on mouse embryonic fibroblast feeders with high dose activin A (100-200 ng/ml in 0.5-2% FBS/DMEM/F12) for 4 days. The no activin A control received 0.5-2% FBS/DMEM/F12 with no added activin A. At four days, cultures received either no activin A in 2% FBS (none), and in 2% serum replacement (SR), or 50 ng/ml activin A together with 2 µM RA and 50 ng/ml FGF-10 in 2% FBS/DMEM/F12 (none, +FBS, +B27) and similarly in 2% Serum replacement (SR). B27 supplement, (Gibco/BRL), was added as a 1/50 dilution directly into 2% FBS/DMEM/F12 (+B27). Duplicate cell samples where taken for each point, and total RNA was isolated and subjected to Q-PCR as previously described.

FIGS. 39A-39E shows that serum-free supplement B27 provided an additional benefit for induction of PDX1 gene expression without inducing an increase in the expression of markers genes not specific for foregut endoderm as compared to such marker gene expression in cells grown without serum.

Example 16

Use of Activin B to Enhance Induction of PDX1

This Example shows that the use of activin B enhances the differentiation of PDX1-negative cells to PDX1-positive cells in in vitro cell culture.

Human embryonic stem cells were induced to differentiate to definitive endoderm by treatment of undifferentiated hESCs grown on mouse embryonic fibroblast feeders with high dose activin A (50 ng/ml) in low serum/RPMI for 6 days. The FBS dose was 0% on day one, 0.2% on day two and 2% on days 3-6. The negative control for definitive endoderm production (NF) received 2% FBS/RPMI with no added activin A. In order to induce PDX1 expression, each of the cultures received retinoic acid at 2 µM in 2% FBS/RPMI on day 6. The cultures treated with activin A on days one through five were provided with different dosing combinations of activin A and activin B or remained in activin A alone at 50 ng/ml. The no activin A control culture (NF) was provided neither activin A nor activin B. This RA/activin treatment was carried out for 3 days at which time PDX1 gene expression was measured by Q-PCR from duplicate cell samples.

Figure 40A:
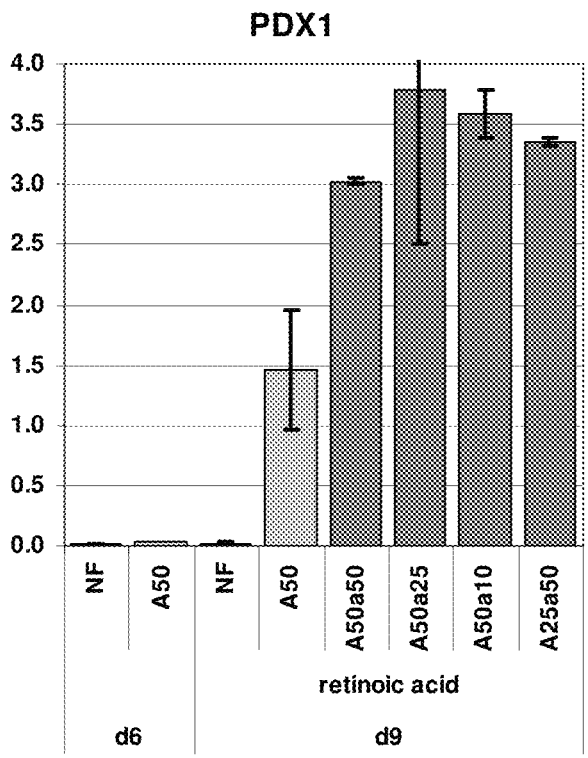
FIGS. 40A-40B are charts which show the relative expression of marker genes for pancreas (PDX1, HNF6) and liver (HNF6) in a culture of hESCs after 6 days (just prior to addition of RA) and at 9 days (three days after exposure to RA). Various conditions were included to compare the addition of activin B at doses of 10 ng/ml (a10), 25 ng/ml (a25) or 50 ng/ml (a50) in the presence of either 25 ng/ml (A25) or 50 ng/ml (A50) activin A. The condition without any activin A or activin B (NF) serves as the negative control for definitive endoderm and PDX1-positive endoderm production. The panels show the relative levels of expression of the following marker genes: (A) PDX1 and (B) HNF6.
Figure 40B:
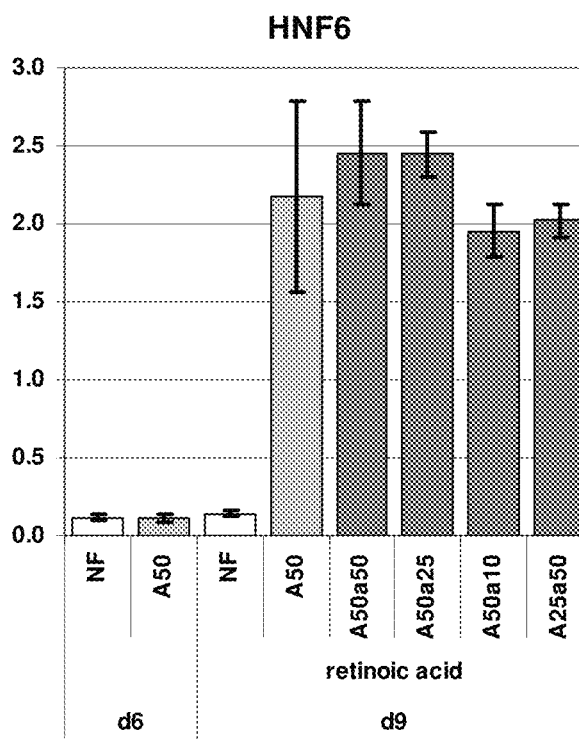

FIG. 40A shows that the addition of activin B at doses ranging from 10-50 ng/ml (a10, a25 and a50) in the presence of 25 ng/ml (A25) or 50 ng/ml (A50) of activin A increased the PDX1 expression at least 2-fold over the culture that received only activin A at 50 ng/ml. The increase in PDX1 as a result of activin B addition was without increase in HNF6 expression (see FIG. 40B), which is a marker for liver as well as pancreas at this time in development. This result suggests that the proportion of cells differentiating to pancreas had been increased relative to liver.

Example 17

Use of Serum Dose to Enhance Induction of PDX1

The expression of PDX1 in definitive endoderm cells is influenced by the amount of serum present in the cell culture throughout the differentiation process. The following experiment shows that the level of serum in a culture during the differentiation of hESCs to PDX1-negative definitive endoderm has an effect on the expression of PDX1 during further differentiation of these cells to PDX1-positive endoderm.

Human embryonic stem cells were induced to differentiate to definitive endoderm by treatment of undifferentiated hESCs grown on mouse embryonic fibroblast feeders with high dose activin A (100 ng/ml) in low serum/RPMI for 5 days. The FBS dose was 0.1% on day one, 0.5% on day two and either 0.5%, 2% or 10% on days 3-5. The no activin A control (NF) received the same daily FBS/RPMI dosing, but with no added activin A. PDX1 expression was induced beginning at day 6 by the addition of RA. During days 6-7, cultures received retinoic acid at 2 µM in 0.5% FBS/RPMI, 1 µM on day 8 and 0.2 µM on day 9-11. The activin A was lowered to 50 ng/ml during retinoic acid treatment and was left absent from the no activin A control (NF).

Figure 41A:
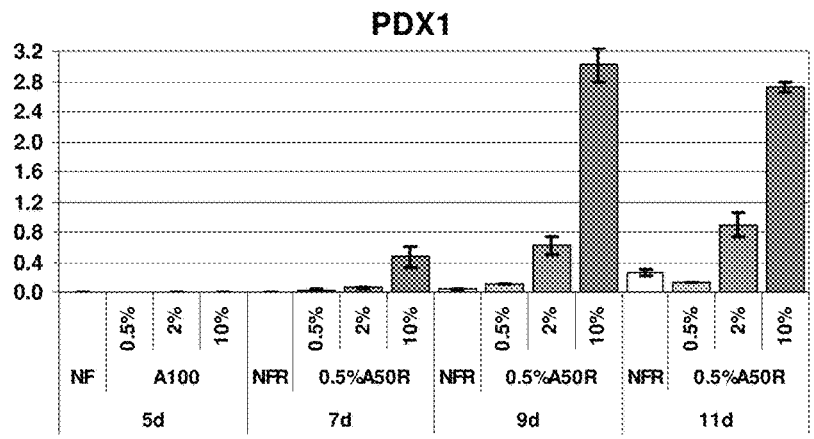
FIGS. 41A-41C are charts which show the relative expression of marker genes in a culture of hESCs with 100 ng/ml (A100), 50 ng/ml (A50) or without (NF) activin A at 5 days (just prior to retinoic acid addition) and at 2, 4, and 6 days after RA exposure (day 7, 9, and 11, respectively). The percentage label directly under each bar indicates the FBS dose during days 3-5 of differentiation. Starting at day 7, cells treated with RA (R) were grown in RPMI medium comprising 0.5% FBS. The RA concentration was 2 µM on day 7, 1 µM on day 9 and 0.2 µM on day 11. The panels show the relative levels of expression of the following marker genes: (A) PDX1; (B) ZIC1; (C) SOX7.
Figure 41B:
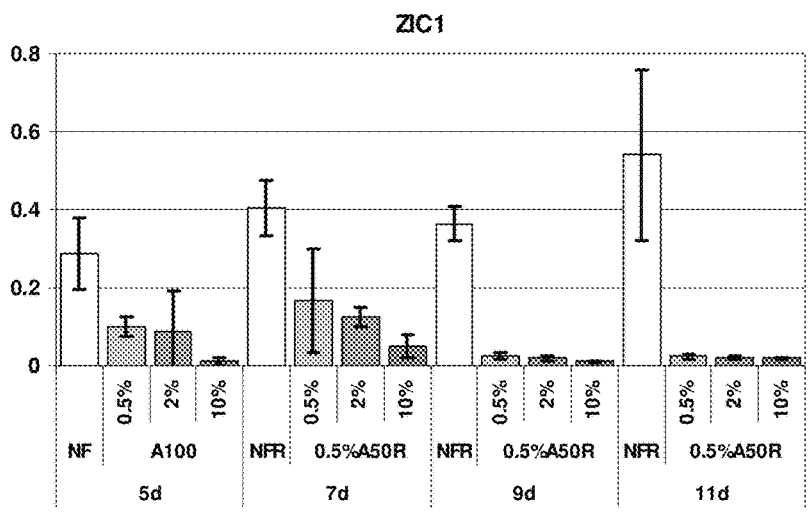
Figure 41C:
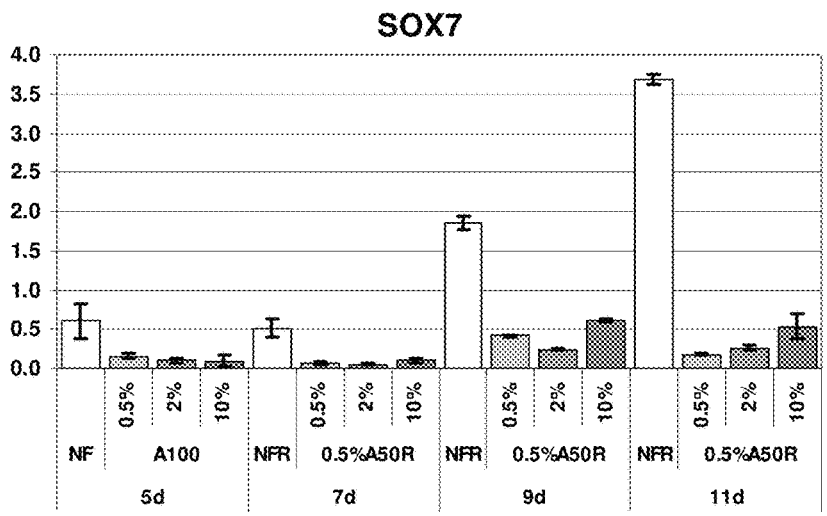

FIG. 41A shows that the FBS dosing during the 3 day period of definitive endoderm induction (days 3, 4 and 5) had a lasting ability to change the induction of PDX1 gene expression during the retinoic acid treatment. This was without significant alteration in the expression pattern of ZIC1 (FIG. 41B) or SOX7 (FIG. 41C) gene expression.

Example 18

Use of Conditioned Medium to Enhance Induction of PDX1

Other factors and growth conditions which influence the expression of PDX1 in definitive endoderm cells were also studied. The following experiment shows the effect of conditioned media on the differentiation of PDX1-negative definitive endoderm cells to PDX1-positive endoderm cells.

Human embryonic stem cells were induced to differentiate to definitive endoderm by treatment of undifferentiated hESCs grown on mouse embryonic fibroblast feeders with high dose activin A (100 ng/ml) in low serum/RPMI for 5 days. The FBS dose was 0.2% on day one, 0.5% on day two and 2% on days 3-5.

The definitive endoderm cultures generated by 5 days of activin A treatment were then induced to differentiate to PDX1 expressing endoderm by the addition of RA in 2% FBS/RPMI containing activin A at 25 ng/ml for four days. The RA was 2 µM for the first two days of addition, 1 µM on the third day and 0.5 µM on the fourth day. This base medium for PDX1 induction was provided fresh (2A25R) or after conditioning for 24 hours by one of four different cell populations. Conditioned media (CM) were generated from either mouse embryonic fibroblasts (MEFCM) or from hESCs that were first differentiated for 5 days by one of three conditions; i) 3% FBS/RPMI (CM2), or ii) activin A (CM3) or iii) bone morphogenic protein 4 (BMP4) (CM4). Activin A or BMP4 factors were provided at 100 ng/ml under the same FBS dosing regimen described above (0.2%, 0.5%, 2%). These three different differentiation paradigms yield three very different populations of human cells by which the PDX1 induction media can be conditioned. The 3% FBS without added growth factor (NF) yields a heterogeneous population composed in large part of extraembryonic endoderm, ectoderm and mesoderm cells. The activin A treated culture (A100) yields a large proportion of definitive endoderm and the BMP4 treated culture (B100) yields primarily trophectoderm and some extraembryonic endoderm.

Figure 42A:
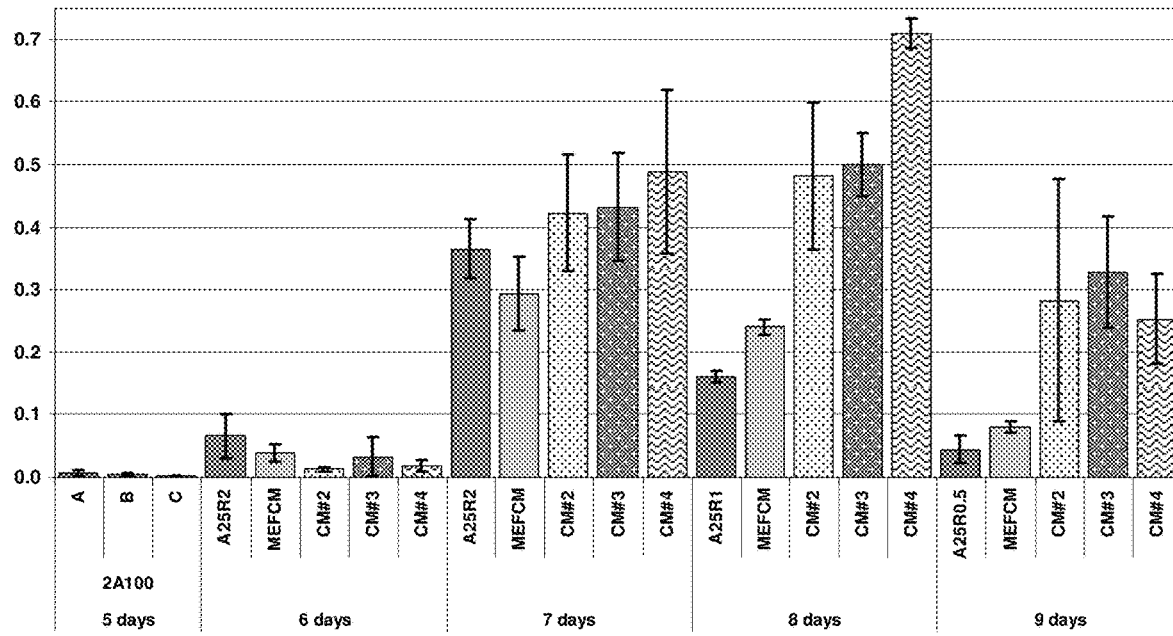
FIGS. 42A-42B are charts which show the relative expression of marker genes in a culture of hESCs treated first with activin A in low FBS to induce definitive endoderm (day 5) and then with fresh (A25R) medium comprising 25 ng/ml activin A and RA or various conditioned media (MEFCM, CM #2, CM #3 and CM #4) and RA to induce PDX1-expressing endoderm. Marker expression was determined on days 5, 6, 7, 8 and 9. The panels show the relative levels of expression of the following marker genes: (A) PDX1; (B) CDX1.
Figure 42B:
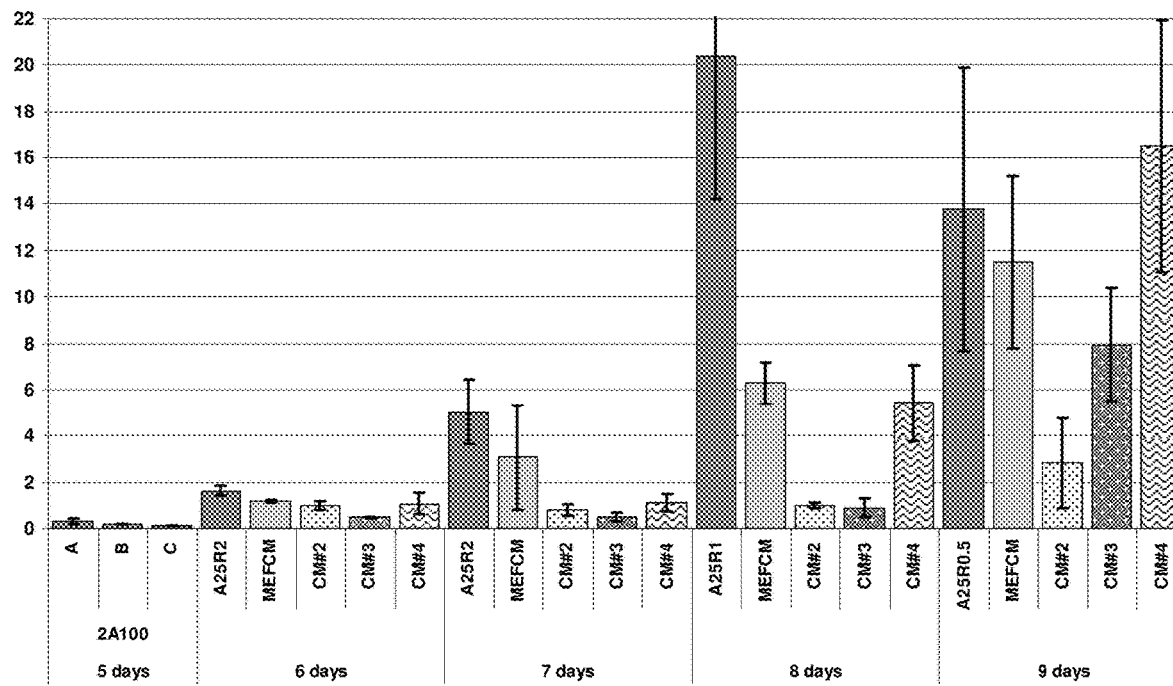

FIG. 42A shows that PDX1 was induced equivalently in fresh and conditioned media over the first two days of RA treatment. However, by the third day PDX1 expression had started to decrease in fresh media and MEF conditioned media treatments. The differentiated hESCs produced conditioned media that resulted in maintenance or further increases in the PDX1 gene expression at levels 3 to 4-fold greater than fresh media. The effect of maintaining high PDX1 expression in hESC-conditioned media was further amplified on day four of RA treatment achieving levels 6 to 7-fold higher than in fresh media. FIG. 42B shows that the conditioned media treatments resulted in much lower levels of CDX1 gene expression, a gene not expressed in the region of PDX1 expressing endoderm. This indicates that the overall purity of PDX1-expressing endoderm was much enhanced by treating definitive endoderm with conditioned media generated from differentiated hESC cultures.

Figure 43:
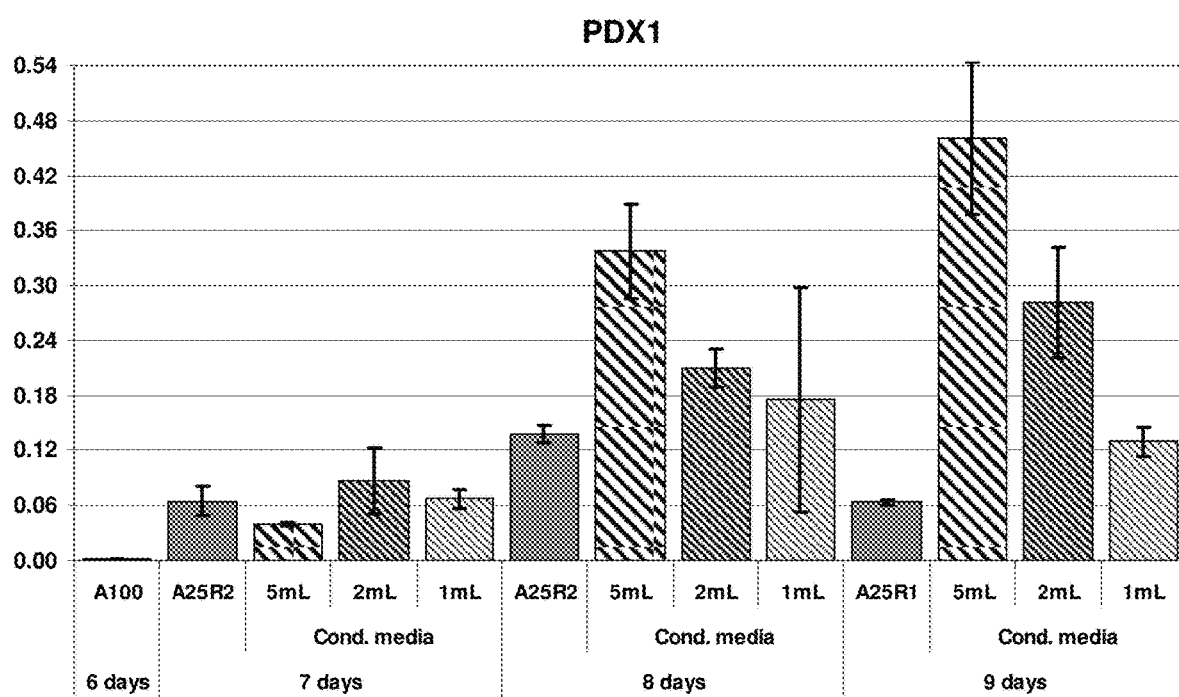
FIG. 43 is a chart which shows the relative expression of PDX1 in a culture of hESCs treated first with activin A in low FBS to induce definitive endoderm and followed by fresh media comprising activin A and retinoic acid (A25R) or varying amounts of RA in conditioned media diluted into fresh media. Total volume of media is 5 ml in all cases.

FIG. 43 shows that PDX1 gene expression exhibited a positive dose response to the amount of conditioned media applied to the definitive endoderm cells. Total volume of media added to each plate was 5 ml and the indicated volume (see FIG. 43) of conditioned media was diluted into fresh media (A25R). It is of note that just 1 ml of conditioned media added into 4 ml of fresh media was still able to induce and maintain higher PDX1 expression levels than 5 ml of fresh media alone. This suggests that the beneficial effect of conditioned media for induction of PDX1 expressing endoderm is dependent on the release of some substance or substances from the cells into the conditioned media and that this substance(s) dose dependently enhances production of PDX1-expressing endoderm.

Example 19

Validation of Antibodies which Bind to PDX1

Antibodies that bind to PDX1 are useful tools for monitoring the induction of PDX1 expression in a cell population. This Example shows that rabbit polyclonal and IgY antibodies to PDX1 can be used to detect the presence of this protein.

In a first experiment, IgY anti-PDX1 (IgY α-PDX1) antibody binding to PDX1 in cell lysates was validated by Western blot analysis. In this analysis, the binding of IgY α-PDX1 antibody to 50 µg of total cell lysate from MDX12 human fibroblasts or MDX12 cells transfected 24 hrs previously with a PDX1 expression vector was compared. The cell lysates separated by SDS-PAGE, transferred to a membrane by electroblotting, and then probed with the IgY α-PDX1 primary antiserum followed by alkaline phosphatase conjugated rabbit anti-IgY (Rb α-IgY) secondary antibodies. Different dilutions of primary and secondary antibodies were applied to separate strips of the membrane in the following combinations: A (500× dilution of primary, 10,000× dilution of secondary), B (2,000×, 10,000×), C (500×, 40,000×), D (2,000×, 40,000), E (8,000×, 40,000×).

Binding was detected in cells transfected with the PDX1 expression vector (PDX1-positive) at all of the tested antibody combinations. Binding was only observed in untransfected (PDX1-negative) fibroblasts when using the highest concentrations of both primary and secondary antibody together (combination A). Such non-specific binding was characterized by the detection of an additional band at a molecular weight slightly higher than PDX1 in both the transfected and untransfected fibroblasts.

In a second experiment, the binding of polyclonal rabbit anti-PDX1 (Rb α-PDX1) antibody to PDX1 was tested by immunocytochemistry. To produce a PDX1 expressing cell for such experiments, MS1-V cells (ATCC # CRL-2460) were transiently transfected with an expression vector of PDX1-EGFP (constructed using pEGFP-N1, Clontech). Transfected cells were then labeled with Rb α-PDX1 and α-EGFP antisera. Transfected cells were visualized by both EGFP fluorescence as well as α-EGFP immunocytochemistry through the use of a Cy5 conjugated secondary antibody. PDX1 immunofluorescence was visualized through the use of an α-Rb Cy3-conjugated secondary antibody.

Binding of the Rb α-PDX1 and the α-EGPF antibodies co-localized with GPF expression.

Example 20

Immunocytochemistry of Human Pancreatic Tissue

This Example shows that antibodies having specificity for PDX1 can be used to identify human PDX1-positive cells by immunocytochemistry.

In a first experiment, paraffin embedded sections of human pancreas were stained for insulin with guinea pig anti-insulin (Gp α-Ins) primary antibody at a 1/200 dilution followed by dog anti-guinea pig (D α-Gp) secondary antibody conjugated to Cy2 at a 1/100 dilution. In a second experiment, the same paraffin embedded sections of human pancreas were stained for PDX1 with IgY α-PDX1 primary antibody at a 1/4000 dilution followed Rb α-IgY secondary antibody conjugated to AF555 at a 1/300 dilution. The images collected from the first and second experiments where then merged. In a third experiment, cells that were stained with IgY α-PDX1 antibodies were also stained with DAPI.

Analysis of the human pancreatic sections revealed the presence of strong staining of islets of Langerhans. Although the strongest PDX1 signal appeared in islets (insulin-positive), weak staining was also seen in acinar tissue (insulin-negative). DAPI and PDX1 co-staining shows that PDX1 was mostly but not exclusively localized to the nucleus.

Example 21

Immunoprecipitation of PDX1 from Retinoic Acid Treated Cells

To further confirm PDX1 expression in definitive endoderm cells that have been differentiated in the presence of RA and the lack of PDX1 in definitive endoderm cells that have not been differentiated with RA, a rabbit anti-PDX1 (Rb α-PDX1) antibody was used to immunoprecipitate PDX1 from both RA differentiated and undifferentiated definitive endoderm cells Immunoprecipitated RA was detected by Western blot analysis using IgY α-PDX1 antibody.

To obtain undifferentiated and differentiated definitive endoderm cell lysates for immunoprecipitation, hESCs were treated for 5 days with activin A at 100 ng/ml in low serum (definitive endoderm) followed by treatment with activin A at 50 ng/ml and 2 µM all-trans RA for two days, 1 µM for one day and 0.2 µM for one day (PDX1-positive foregut endoderm). As a positive control cell lysates were also prepared from MS1-V cells (ATCC #CRL-2460) transfected with a PDX1 expression vector. PDX1 was immunoprecipitated by adding Rb α-PDX1 and rabbit-specific secondary antibodies to each lysate. The precipitate was harvested by centrifugation Immunoprecipitates were dissolved in SDS-containing buffer then loaded onto a polyacrylamide gel. After separation, the proteins were transferred to a membrane by electroblotting, and then probed with the IgY α-PDX1 primary antibody followed by labeled Rb α-IgY secondary antibodies.

Figure 44:
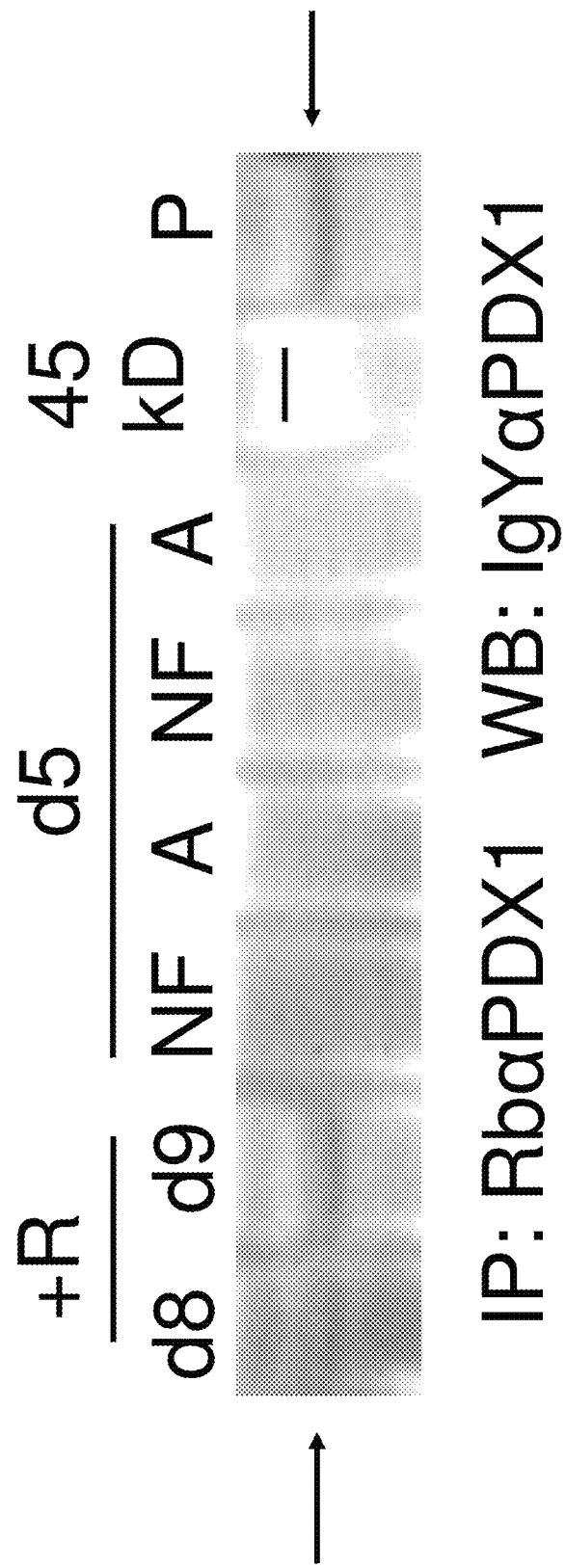
FIG. 44 is a Western blot showing PDX1 immunoprecipitated from RA-treated definitive endoderm cells 3 days (d8) and 4 days (d9) after the addition of RA and 50 ng/ml activin A.

Immunoprecipitates collected from the MS1-V positive control cells as well as those from day 8 (lane d8, three days after the start of RA treatment) and day 9 (lane d9, four days after the start of RA) cells were positive for PDX1 protein (FIG. 44). Precipitates obtained from undifferentiated definitive endoderm cells (that is, day 5 cells treated with activin A—designated (A) in FIG. 44) and undifferentiated hESCs (that is, untreated day 5 cells—designated as (NF) in FIG. 44) were negative for PDX1.

Example 22

Generation of PDX1 Promoter-EGFP Transgenic hESC Lines

In order to use the PDX1 marker for cell isolation, we genetically tagged PDX1-positive foregut endoderm cells with an expressible reporter gene. This Example describes the construction of a vector comprising a reporter cassette which comprises a reporter gene under the control of the PDX1 regulatory region. This Example also describes the preparation of a cell, such as a human embryonic stem cell, transfected with this vector as well as a cell having this reporter cassette integrated into its genome.

PDX1-expressing definitive endoderm cell lines genetically tagged with a reporter gene were constructed by placing a GFP reporter gene under the control of the regulatory region (promoter) of the PDX1 gene. First, a plasmid construct in which EGFP expression is driven by the human PDX1 gene promoter was generated by replacing the CMV promoter of vector pEGFP-N1 (Clontech) with the human PDX1 control region (Genbank Accession No. AF192496, the disclosure of which is incorporated herein by reference in its entirety), which comprises a nucleotide sequence ranging from about 4.4 kilobase pairs (kb) upstream to about 85 base pairs (bp) downstream of the PDX1 transcription start site. This region contains the characterized regulatory elements of the PDX1 gene, and it is sufficient to confer the normal PDX1 expression pattern in transgenic mice. In the resulting vector, expression of EFGP is driven by the PDX1 promoter. In some experiments, this vector can be transfected into hESCs.

The PDX1 promoter/EGFP cassette was excised from the above vector, and then subcloned into a selection vector containing the neomycin phosphotransferase gene under control of the phosphoglycerate kinase-1 promoter. The selection cassette was flanked by flp recombinase recognition sites to allow removal of the cassette. This selection vector was linearized, and then introduced into hESCs using standard lipofection methods. Following 10-14 days of selection in G418, undifferentiated transgenic hESC clones were isolated and expanded.

Example 23

Isolation of PDX1-Positive Foregut Endoderm

The following Example demonstrates that hESCs comprising the PDX1 promoter/EGFP cassette can be differentiated into PDX1-positive endoderm cells and then subsequently isolated by fluorescence-activated cell sorting (FACS).

PDX1 promoter/EGFP transgenic hESCs were differentiated for 5 days in activin A-containing media followed by two days in media comprising activin A and RA. The differentiated cells were then harvested by trypsin digestion and sorted on a Becton Dickinson FACS Diva directly into RNA lysis buffer or PBS. A sample of single live cells was taken without gating for EGFP (Live) and single live cells were gated into EGFP positive (GFP) and GFP negative (Neg) populations. In one experiment, the EGFP positive fraction was separated into two equally sized populations according to fluorescence intensity (Hi and Lo).

Following sorting, cell populations were analyzed by both Q-PCR and immunocytochemistry. For Q-PCR analysis, RNA was prepared using Qiagen RNeasy columns and then converted to cDNA. Q-PCR was conducted as described previously. For immunocytochemistry analysis, cells were sorted into PBS, fixed for 10 minutes in 4% paraformaldehyde, and adhered to glass slides using a Cytospin centrifuge. Primary antibodies to Cytokeratin19 (KRT19) were from Chemicon; to Hepatocyte nuclear factor 3 beta (HNF3β) from Santa Cruz; to Glucose Transporter 2 (GLUT2) from R&D systems. Appropriate secondary antibodies conjugated to FITC (green) or Rhodamine (Red) were used to detect binding of the primary antibodies.

Figure 45:
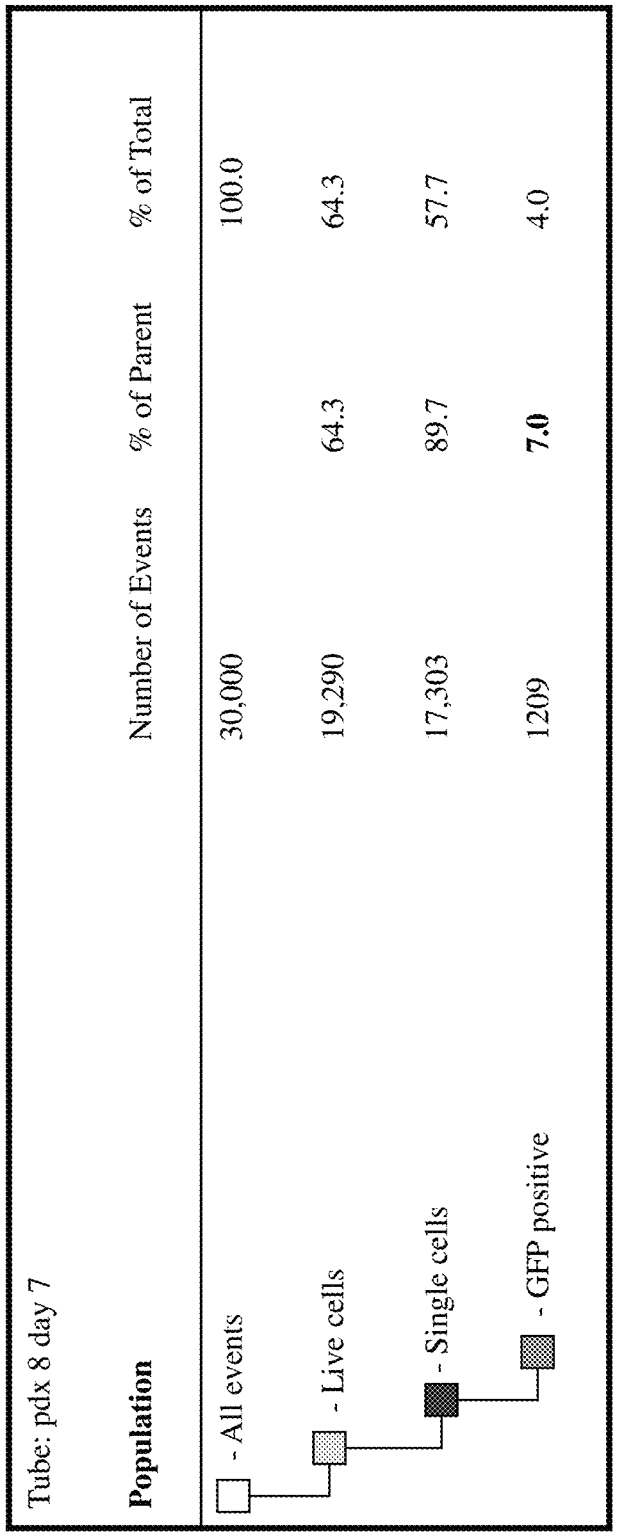
FIG. 45 is a summary chart displaying the results of a fluorescence-activated cell sort (FACs) of PDX1-positive foregut endoderm cells genetically tagged with a EGFP reporter under control of the PDX1 promoter.

A typical FACS sort of differentiated cells is shown in FIG. 45. The percent isolated PDX1-positive cells in this example was approximately 7%, which varied depending on the differentiation efficiency from about 1% to about 20%.

Figure 46:
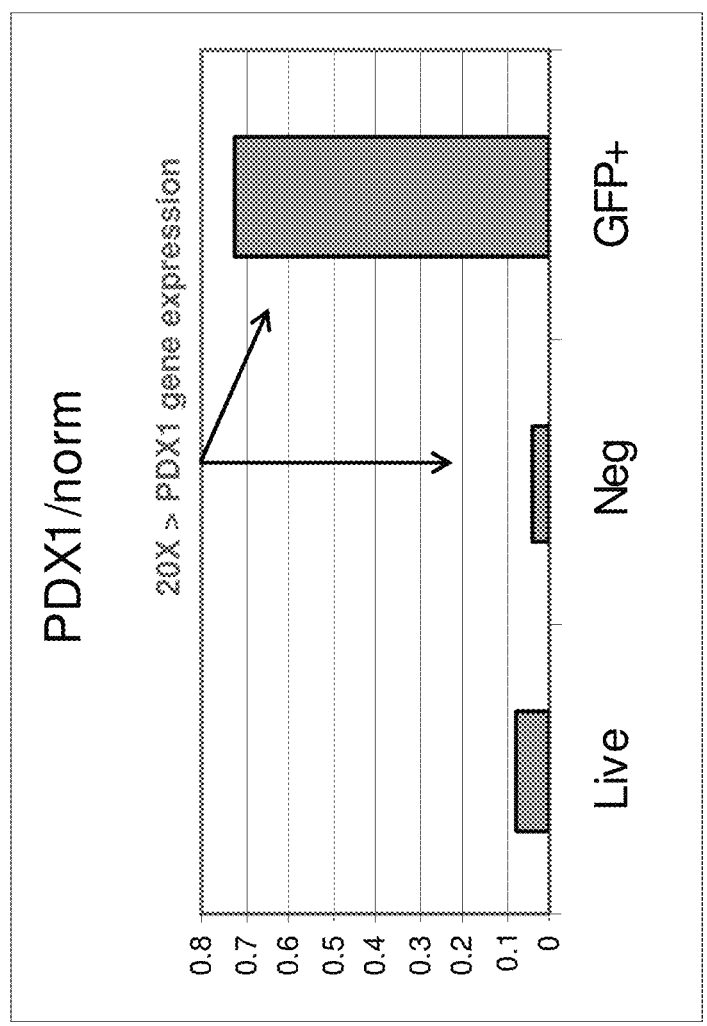
FIG. 46 is a chart showing relative PDX1 expression levels normalized to housekeeping genes for sorted populations of live cells (Live), EGFP-negative cells (Neg) and EGFP-positive cells (GFP+).
Figure 47:
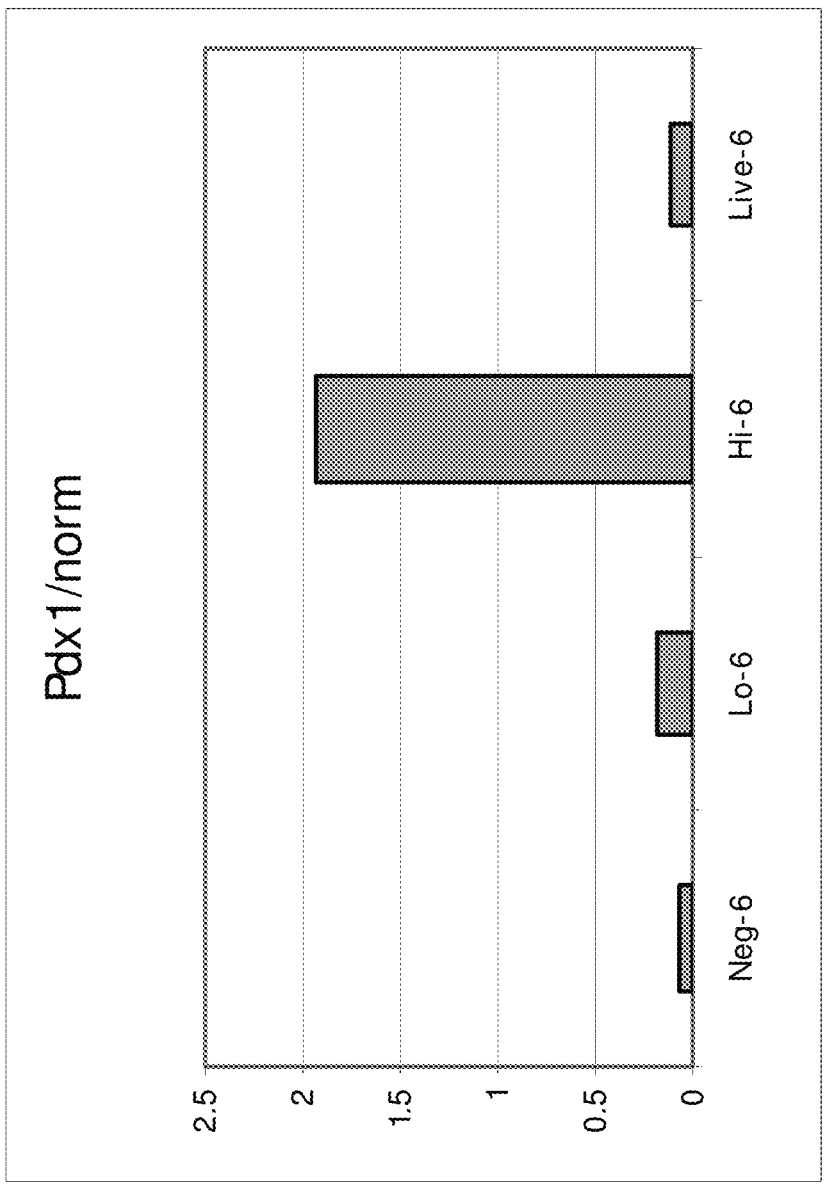
FIG. 47 is a chart showing relative PDX1 expression levels normalized to housekeeping genes for sorted populations of live cells (Live), EGFP-negative cells (Neg), the half of the EGFP-positive cell population that has the lowest EGFP signal intensity (Lo) and the half of the EGFP-positive cell population that has the highest EGFP signal intensity (Hi).
Figures 49A, 49B:
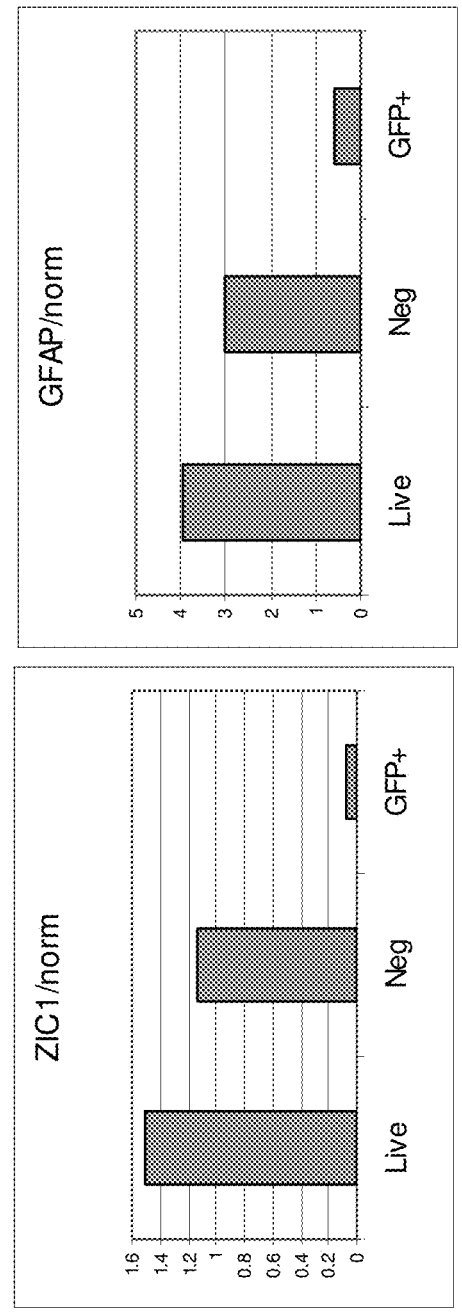
FIGS. 49A-49B are charts showing the relative expression levels normalized to housekeeping genes of two non-pancreatic endoderm markers in sorted populations of live cells (Live), EGFP-negative cells (Neg) and EGFP-positive cells (GFP+). Panels: A—ZIC1 and B—GFAP.

Sorted cells were further subjected to Q-PCR analysis. Differentiated cells showed a correlation of EGFP fluorescence with endogenous PDX1 gene expression. Compared to non-fluorescing cells, the EGFP positive cells showed a greater than 20-fold increase in PDX1 expression levels (FIG. 46). The separation of high and low EGFP intensity cells indicated that EGFP expression level correlated with PDX1 expression level (FIG. 47). In addition to PDX1 marker analysis, sorted cells were subjected to Q-PCR analysis of several genes that are expressed in pancreatic endoderm. Products of each of these marker genes (NKX2.2, GLUT2, KRT19, HNF4c and HNF3β) were all enriched in the EGFP positive fraction (FIGS. 48A-48E). In contrast, the neural markers ZIC1 and GFAP were not enriched in sorted EGFP expressing cells (FIGS. 49A and 49B).

By immunocytochemistry, virtually all the isolated PDX1-positive cells were seen to express KRT19 and GLUT2. This result is expected for cells of the pancreatic endoderm lineage. Many of these cells were also HNF3l3 positive by antibody staining.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Beck, S., Le Good, J. A., Guzman, M., Ben Haim, N., Roy, K., Beermann, F., and Constam, D. B. (2002). Extraembryonic proteases regulate Nodal signalling during gastrulation. Nat Cell Biol 4, 981-985.

Beddington, R. S., Rashbass, P., and Wilson, V. (1992). Brachyury—a gene affecting mouse gastrulation and early organogenesis. Dev Suppl, 157-165.

Bongso, A., Fong, C. Y., Ng, S. C., and Ratnam, S. (1994). Isolation and culture of inner cell mass cells from human blastocysts. Hum Reprod 9, 2110-2117.

Chang, H., Brown, C. W., and Matzuk, M. M. (2002). Genetic analysis of the mammalian transforming growth factor-beta superfamily Endocr Rev 23, 787-823.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Harris, T. M., and Childs, G. (2002). Global gene expression patterns during differentiation of F9 embryonal carcinoma cells into parietal endoderm. Funct Integr Genomics 2, 105-119.

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in *Xenopus*. Cell 91, 397-405.

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C. H., and Broxmeyer, H. E. (1999). Chemokines: signal lamps for trafficking of T and B cells for development and effector function. J Leukoc Biol 65, 6-15.

Kimelman, D., and Griffin, K. J. (2000). Vertebrate mesendoderm induction and patterning. Curr Opin Genet Dev 10, 350-356.

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlow, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cella, 171-181.

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H. (2001). Divergence and convergence of TGF-beta/BMP signaling. J Cell Physiol 187, 265-276.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm. an ancient germ layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zicl expression in brain and somites is affected by BMP and hedgehog signalling. Mech Dev 85, 147-159.

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of *Xenopus laevis* xSox7 cDNA. Biochim Biophys Acta 1309, 73-76.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003). Cell fate decisions within the mouse organizer are governed by graded Nodal signals. Genes Dev 17, 1646-1662.

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993). Nodal is a novel TGF-beta-like gene expressed in the mouse node during gastrulation. Nature 361, 543-547.

What is claimed is:

1. An in vitro cell culture comprising:
   human pancreatic and duodenal homeobox 1 (PDX1)-negative definitive endoderm cells;
   a medium comprising an effective amount of B27, a retinoid and a fibroblast growth factor (FGF), to differentiate the PDX1-negative definitive endoderm cells to PDX1-positive foregut endoderm cells; and
   PDX1-positive foregut endoderm cells,
   such that the amount of PDX1 expressed by the PDX1-positive foregut endoderm cells is increased in the in vitro cell culture as compared to a second in vitro cell culture comprising human PDX1-negative definitive endoderm cells, PDX1-positive foregut endoderm cells, and the medium without B27.

2. The in vitro cell culture of claim 1, wherein B27 is present in the in vitro cell culture at a concentration of about 0.1% v/v to about 20% v/v.

3. The in vitro cell culture of claim 1, wherein the retinoid is retinoic acid (RA).

4. The in vitro cell culture of claim 3, wherein RA is present in the in vitro cell culture and the second in vitro cell culture at a concentration of about 0.01 µM to about 50 µM.

5. The in vitro cell culture of claim 1, wherein the FGF is FGF-10 or FGF-4.

6. The in vitro cell culture of claim 1, wherein the in vitro cell culture and the second in vitro cell culture further comprise a transforming growth factor beta (TGFβ) family member.

7. The in vitro cell culture of claim 6, wherein the TGFβ family member is Activin A.

8. An in vitro method of producing human PDX1-positive foregut endoderm cells, comprising:
   (a) culturing a population of human pluripotent stem cells in vitro,
   (b) differentiating the human pluripotent stem cells in vitro in the presence of an exogenous transforming growth factor beta (TGFβ) superfamily growth factor to obtain a population comprising at least 15% definitive endoderm cells, and
   (c) differentiating the definitive endoderm cells of step (b) in the presence of a retinoid in vitro to obtain PDX1-positive foregut endoderm cells, wherein the PDX1-positive foregut endoderm cells are multipotent and can differentiate into cells, tissues or organs from the posterior portion of the gut tube.

* * * * *

SEQUENCE LISTING

```
<160> NUMBER OF SEQ ID NOS: 2

<210> SEQ ID NO 1
<211> LENGTH: 1245
<212> TYPE: DNA
<213> ORGANISM: Homo sapiens

<400> SEQUENCE: 1
atgagcagcc cggatgcggg atacgccagt gacgaccaga gccagaccca gagcgcgctg      60
cccgcggtga tggccgggct gggcccctgc ccctgggccg agtcgctgag ccccatcggg     120
gacatgaagg tgaagggcga ggcgccggcg aacagcggag caccggccgg ggccgcgggc     180
cgagccaagg gcgagtcccg tatccggcgg ccgatgaacg ctttcatggt gtgggctaag     240
gacgagcgca agcggctggc gcagcagaat ccagacctgc acaacgccga gttgagcaag     300
atgctgggca agtcgtggaa ggcgctgacg ctggcggaga agcggccctt cgtggaggag     360
```

```
gcagagcggc tgcgcgtgca gcacatgcag gaccacccca actacaagta ccggccgcgg    420
cggcgcaagc aggtgaagcg gctgaagcgg gtggagggcg gcttcctgca cggcctggct    480
gagccgcagg cggccgcgct gggccccgag gcggccgcg tggccatgga cggcctgggc     540
ctccagttcc ccgagcaggg cttccccgcc ggccgccgc tgctgcctcc gcacatgggc     600
ggccactacc gcgactgcca gagtctgggc gcgcctccgc tcgacggcta cccgttgccc    660
acgcccgaca cgtccccgct ggacggcgtg gaccccgacc cggctttctt cgccgccccg    720
atgcccgggg actgcccggc ggccggcacc tacagctacg cgcaggtctc ggactacgct    780
ggccccccgg agcctcccgc cggtcccatg caccccccgac tcggcccaga gcccgcgggt    840
ccctcgattc cgggcctcct ggcgccaccc agcgcccttc acgtgtacta cggcgcgatg    900
ggctcgcccg gggcgggcgg cgggcgcggc ttccagatgc agccgcaaca ccagcaccag    960
caccagcacc agcaccaccc ccggggcccc ggacagccgt cgcccccctcc ggaggcactg   1020 ccctgccggg acggcacgga ccccagtcag ccgccgagc tcctcgggga ggtggaccgc    1080
acggaatttg aacagtatct gcacttcgtg tgcaagcctg agatgggcct ccctaccag    1140 gggcatgact ccggtgtgaa tctccccgac agccacgggg ccatttcctc ggtggtgtcc    1200
gacgccagct ccgcggtata ttactgcaac tatcctgacg tgtga                   1245
```

<210> SEQ ID NO 2
<211> LENGTH: 414
<212> TYPE: PRT
<213> ORGANISM: Homo sapiens

<400> SEQUENCE: 2

Met Ser Ser Pro Asp Ala Gly Tyr Ala Ser Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Glu Ala Glu Arg Leu Arg Val Gln His
        115                 120                 125

Met Gln Asp His Pro Asn Tyr Lys Tyr Arg Pro Arg Arg Arg Lys Gln
    130                 135                 140

Val Lys Arg Leu Lys Arg Val Glu Gly Gly Phe Leu His Gly Leu Ala
145                 150                 155                 160

Glu Pro Gln Ala Ala Ala Leu Gly Pro Glu Gly Gly Arg Val Ala Met
                165                 170                 175

Asp Gly Leu Gly Leu Gln Phe Pro Glu Gln Gly Phe Pro Ala Gly Pro
            180                 185                 190

Pro Leu Leu Pro Pro His Met Gly Gly His Tyr Arg Asp Cys Gln Ser
        195                 200                 205

Leu Gly Ala Pro Pro Leu Asp Gly Tyr Pro Leu Pro Thr Pro Asp Thr
    210                 215                 220

-continued

```
Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
        275                 280                 285

Pro Pro Ser Ala Leu His Val Tyr Tyr Gly Ala Met Gly Ser Pro Gly
    290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
            340                 345                 350

Glu Leu Leu Gly Glu Val Asp Arg Thr Glu Phe Glu Gln Tyr Leu His
        355                 360                 365

Phe Val Cys Lys Pro Glu Met Gly Leu Pro Tyr Gln Gly His Asp Ser
        370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410
```